US012788761B2

(12) United States Patent
Gummadi et al.

(10) Patent No.: US 12,788,761 B2
(45) Date of Patent: Nov. 10, 2026

(54) COMPOUNDS AND COMPOSITIONS FOR TREATING HEMATOLOGICAL DISORDERS

(71) Applicant: Aurigene Oncology Limited, Bangalore (IN)

(72) Inventors: Venkateshwar Rao Gummadi, Bangalore (IN); Susanta Samajdar, Bangalore (IN); Kavitha Nellore, Bangalore (IN); Girish Daginakatte, Bangalore (IN); Wesley Roy Balasubramanian, Hosur (IN)

(73) Assignee: Aurigene Oncology Limited, Bangalore (IN)

( * ) Notice: Subject to any disclaimer, the term of this patent is extended or adjusted under 35 U.S.C. 154(b) by 1131 days.

(21) Appl. No.: 17/853,299

(22) Filed: Jun. 29, 2022

(65) Prior Publication Data

US 2022/0339161 A1 Oct. 27, 2022

Related U.S. Application Data

(63) Continuation of application No. 16/498,866, filed as application No. PCT/IB2018/052232 on Mar. 30, 2018, now Pat. No. 11,419,875.

(30) Foreign Application Priority Data

Mar. 31, 2017 (IN) ............................ 201741011785

(51) Int. Cl.

*A61K 31/5377* (2006.01)
*A61K 31/416* (2006.01)
(Continued)

(52) U.S. Cl.

CPC ...... *A61K 31/5377* (2013.01); *A61K 31/4439* (2013.01); *A61K 31/4545* (2013.01); *A61P 35/02* (2018.01)

(58) Field of Classification Search

CPC ........... A61K 31/5377; A61K 31/4439; A61K 31/4545; A61P 35/02

See application file for complete search history.

(56) References Cited

U.S. PATENT DOCUMENTS 5,494,911 A 2/1996 Bartlett et al.
7,338,950 B2 3/2008 Kelly et al.
(Continued)

FOREIGN PATENT DOCUMENTS

CN 103608017 A 2/2014
EP 1627869 A1 2/2006
(Continued)

OTHER PUBLICATIONS https://www.cancer.org/cancer/types/myelodysplastic-syndrome/about/what-is-mds.html#:~:text=Myelodysplastic%20syndromes%20(MDS)%2C%20also,more%20types%20of%20blood%20cells (Year: 2025).*

(Continued)

*Primary Examiner* — Clinton A Brooks
*Assistant Examiner* — Kendall Nicole Heitmeier
(74) *Attorney, Agent, or Firm* — Foley Hoag LLP; David P. Halstead; Alexander J. Chatterley

(57) ABSTRACT

The present invention provides methods of treating hematological disorders, such as acute myeloid leukemia and myelodysplastic syndrome, using substituted heterocyclic compounds and pharmaceutically acceptable salts thereof. The substituted heterocyclic compounds inhibit IRAK4 and FLT-3 kinases. In some aspects, the present invention provides methods of treating myelodysplastic syndrome in a subject, comprising administering a compound represented by Formula II or a pharmaceutically acceptable salt thereof.

(Continued)

| Kinase | Kd (nM) |
|---|---|
| IRAK4 | 23 |
| IRAK1 | 100-1,000 |
| FLT3 | 31 |
| FLT3 (D835H) | 4.6 |
| FLT3 (D835V) | 44 |
| FLT3 (D835Y) | 2.5 |
| FLT3 (ITD) | 7.8 |
| FLT3 (ITD, D835V) | 31 |
| FLT3 (ITD, F691L) | 20 |
| FLT3 (K663Q) | 47 |
| FLT3 (N841I) | 16 |

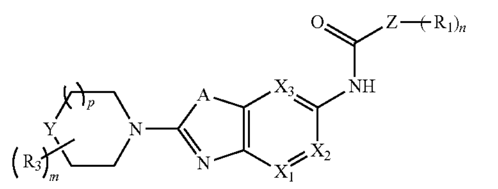

(II)

54 Claims, 6 Drawing Sheets

(51) Int. Cl.

| | |
|---|---|
| ***A61K 31/422*** | (2006.01) |
| ***A61K 31/437*** | (2006.01) |
| ***A61K 31/4439*** | (2006.01) |
| ***A61K 31/444*** | (2006.01) |
| ***A61K 31/4545*** | (2006.01) |
| ***A61K 31/5355*** | (2006.01) |
| ***A61K 45/06*** | (2006.01) |
| ***A61P 35/02*** | (2006.01) |

(56) References Cited

U.S. PATENT DOCUMENTS

| | | | |
|---|---|---|---|
| 9,732,095 | B2 | 8/2017 | Gummadi et al. |
| 9,855,273 | B2 | 1/2018 | Starczynowski et al. |
| 10,047,104 | B2 | 8/2018 | Gummadi et al. |
| 10,160,753 | B2 | 12/2018 | Gummadi et al. |
| 10,640,517 | B2 | 5/2020 | Gummadi et al. |
| 10,758,518 | B2 | 9/2020 | Booher |
| 10,995,100 | B2 | 5/2021 | Gummadi et al. |
| 11,419,875 | B2 | 8/2022 | Gummadi et al. |
| 11,691,987 | B2 | 7/2023 | Gummadi et al. |
| 11,981,685 | B2 | 5/2024 | Gummadi et al. |
| 12,178,821 | B2 | 12/2024 | von Roemeling et al. |
| 12,410,193 | B2 | 9/2025 | Gummadi et al. |
| 2005/0192293 | A1 | 9/2005 | Kelly et al. |
| 2006/0014747 | A1 | 1/2006 | Krueger et al. |
| 2006/0160861 | A1 | 7/2006 | Bohlmann et al. |
| 2009/0069288 | A1 | 3/2009 | Breinlinger et al. |
| 2010/0160388 | A1 | 6/2010 | Brotherton-Pleiss et al. |
| 2010/0210619 | A1 | 8/2010 | Bombrun et al. |
| 2011/0224137 | A1 | 9/2011 | Ting et al. |
| 2012/0015962 | A1 | 1/2012 | Arora et al. |
| 2012/0053345 | A1 | 3/2012 | Ericson et al. |
| 2013/0035326 | A1 | 2/2013 | Abraham et al. |
| 2015/0094315 | A1 | 4/2015 | Choi et al. |
| 2016/0326151 | A1 | 11/2016 | Gummadi et al. |
| 2017/0035881 | A1 | 2/2017 | Lannutti et al. |
| 2017/0152263 | A1 | 6/2017 | Gummadi et al. |
| 2018/0022758 | A1 | 1/2018 | Gummadi et al. |
| 2018/0201609 | A1 | 7/2018 | Gummadi et al. |
| 2018/0208605 | A1 | 7/2018 | Gummadi et al. |
| 2018/0289685 | A1 | 10/2018 | Bothe et al. |
| 2020/0069668 | A1 | 3/2020 | Lannutti et al. |
| 2020/0190112 | A1 | 6/2020 | Gummadi et al. |
| 2021/0290628 | A1 | 9/2021 | Gummadi et al. |
| 2022/0056046 | A1 | 2/2022 | Gummadi et al. |
| 2022/0331330 | A1 | 10/2022 | von Roemeling |
| 2022/0339161 | A1 | 10/2022 | Gummadi et al. |
| 2023/0310444 | A1 | 10/2023 | von Roemeling et al. |
| 2023/0331740 | A1 | 10/2023 | Gummadi et al. |
| 2023/0414582 | A1 | 12/2023 | von Roemeling et al. |
| 2024/0294547 | A1 | 9/2024 | Gummadi et al. |
| 2025/0082644 | A1 | 3/2025 | von Roemeling et al. |

FOREIGN PATENT DOCUMENTS

| | | | | | |
|---|---|---|---|---|---|
| GB | 2406856 | A | | 4/2005 | |
| JP | 2008-239617 | A | | 10/2008 | |
| KR | 20130128693 | A | | 11/2013 | |
| WO | WO-2004/007457 | A2 | | 1/2004 | |
| WO | WO-2004/007458 | A1 | | 1/2004 | |
| WO | WO-2004/098518 | A2 | | 11/2004 | |
| WO | WO-2004/103954 | A1 | | 12/2004 | |
| WO | WO-2004/108133 | A2 | | 12/2004 | |
| WO | WO-05032493 | A2 | | 4/2005 | |
| WO | WO-2005/0107460 | A1 | | 11/2005 | |
| WO | WO-2006/048249 | A1 | | 5/2006 | |
| WO | WO-2006/053227 | A2 | | 5/2006 | |
| WO | WO-2006/066173 | A2 | | 6/2006 | |
| WO | WO-2006/066174 | A1 | | 6/2006 | |
| WO | WO-2006/066795 | A1 | | 6/2006 | |
| WO | WO-2007/058626 | A1 | | 5/2007 | |
| WO | WO-2007/095124 | A2 | | 8/2007 | |
| WO | WO-2007/112914 | A2 | | 10/2007 | |
| WO | WO-2007/117465 | A2 | | 10/2007 | |
| WO | WO-2007/121154 | A2 | | 10/2007 | |
| WO | WO-2008/030579 | A2 | | 3/2008 | |
| WO | WO-2008/030584 | A2 | | 3/2008 | |
| WO | WO-2008/061109 | A2 | | 5/2008 | |
| WO | WO-2008073825 | A1 | | 6/2008 | |
| WO | WO-2008/156614 | A2 | | 12/2008 | |
| WO | WO-2009/012312 | A1 | | 1/2009 | |
| WO | WO-2009/019167 | A1 | | 2/2009 | |
| WO | WO-2009/102468 | A1 | | 8/2009 | |
| WO | WO-2010/008847 | A2 | | 1/2010 | |
| WO | WO-2010/071819 | A1 | | 6/2010 | |
| WO | WO-2011/046954 | A1 | | 4/2011 | |
| WO | WO-2011/133750 | A1 | | 10/2011 | |
| WO | WO-2011/137219 | A1 | | 11/2011 | |
| WO | WO-2011/163640 | A1 | | 12/2011 | |
| WO | WO-2012007375 | A1 | | 1/2012 | |
| WO | WO-2012/068546 | A1 | | 5/2012 | |
| WO | WO-2012/084704 | A1 | | 6/2012 | |
| WO | WO-2012/142125 | A2 | | 10/2012 | |
| WO | WO-2013/042137 | A1 | | 3/2013 | |
| WO | WO-2013/056070 | A2 | | 4/2013 | |
| WO | WO-2013/059587 | A1 | | 4/2013 | |
| WO | WO-2013/068458 | A1 | | 5/2013 | |
| WO | WO-2014/003483 | A1 | | 1/2014 | |
| WO | WO-2014/011902 | A1 | | 1/2014 | |
| WO | WO-2014/070979 | A1 | | 5/2014 | |
| WO | WO-2014/190163 | A2 | | 11/2014 | |
| WO | WO-2015/038503 | A1 | | 3/2015 | |
| WO | WO-2015/091426 | A1 | | 6/2015 | |
| WO | WO-2015/104662 | A1 | | 7/2015 | |
| WO | WO-2015104688 | A1 | * | 7/2015 | ................ A61P 3/06 |
| WO | WO-2015/119998 | A1 | | 8/2015 | |
| WO | WO-2015/193846 | A1 | | 12/2015 | |
| WO | WO-2016/083433 | A1 | | 6/2016 | |
| WO | WO-2016/174183 | A1 | | 11/2016 | |
| WO | WO-2017/009798 | A1 | | 1/2017 | |
| WO | WO-2017/009806 | A1 | | 1/2017 | |
| WO | WO-2017023941 | A1 | * | 2/2017 | ................ A61P 7/02 |
| WO | WO-2018/081738 | A1 | | 5/2018 | |
| WO | WO-2018/178947 | A2 | | 10/2018 | |
| WO | WO-2019/089580 | A1 | | 5/2019 | |
| WO | WO-2020/113233 | A1 | | 6/2020 | |
| WO | WO-2020/264499 | A1 | | 12/2020 | |
| WO | WO-2022/031330 | A1 | | 2/2022 | |
| WO | WO-2022/108996 | A1 | | 5/2022 | |
| WO | WO-2022/216379 | A1 | | 10/2022 | |
| WO | WO-2023/220227 | A1 | | 11/2023 | |
| WO | WO-2024/249837 | A1 | | 12/2024 | |
| WO | WO-2024/249839 | A1 | | 12/2024 | |
| WO | WO-2025/090844 | | | 5/2025 | |
| WO | WO-2025/174879 | A1 | | 8/2025 | |
| WO | WO-2025/208000 | A1 | | 10/2025 | |

OTHER PUBLICATIONS

Pemmaraju, N. et. al. Blood, 2009, 114(22), 1026 (Year: 2009).*

Rhyasen, G. W. âIRAK family kinases as therapeutic targets for Myelodysplastic Syndrome and Acute Myeloid Leukemiaâ University of Cincinnati, 2014, 132 pages (Year: 2014).*

International Preliminary Report on Patentability for Application No. PCT/US2021/059668 dated Feb. 24, 2022.

(56) References Cited

OTHER PUBLICATIONS

Iqbal et al., "Preliminary safety and efficacy data on two patients with relapsed/refractory CNS lymphoma treated with emavusertib (CA-4948) and ibrutinib combination: a subset analysis of TakeAim Lymphoma trial," CURIS Presentation: 1 pg (Nov. 17, 2022).
Lange et al., "Preclinical evaluation of a novel interleukin-I receptor-associated kinase 4 (IRAK.4) inhibitor in combination with PBK inhibitor copanlisib or BTK inhibitors in ABC-DLBCL" [abstract]. In: Proceedings of the American Association for Cancer Research Annual Meeting 2018; Apr. 14-18, 2018; Chicago, IL. Philadelphia (PA): AACR; Cancer Res 2018; 78(13 Suppl):Abstract nr 1887.
Martell., "Discovery and Development of IRAK4 Inhibitor Emavusertib", Curis Presentation: 36 pages (Sep. 29, 2022).
Martell., "Emavusertib," Curis Presentation: 15 pages (Oct. 7, 2022).
Metzeler et al., "ASH Poster #4077: Molecular characterization of clinical response in relapsed/refractory acute myeloid leukemia and high-risk myelodysplastic syndrome patients treated with single agent emavusertib," Pre-ASH Meeting Slideshow, 12 pages (Dec. 1, 2022).
Metzeler et al., "Molecular characterization of clinical response in relapsed/refractory acute myeloid leukemia and high-risk myelodysplastic syndrome patients treated with single agent emavusertib," American Society of Hematology poster, published Nov. 16, 2022 (1 page).
Metzeler et al., "Molecular characterization of clinical response in relapsed/refractory acute myeloid leukemia and high-risk myelodysplastic syndrome patients treated with single agent emavusertib," Curis Inc. Presentation published Nov. 16, 2022 (9 pages).
Von Roemeling et al., "Clinical Activity of IRAK4 Inhibitor, Emavusertib (CA-4948)," Curis Presentation published Oct. 29, 2022 (15 pages).
Zhang, Z. et al. Targeting NF-KB pathway for the therapy of diseases: mechanism and clinical study. Sig Transduct Target Ther 5, 209 (2020).
Issue Notice for U.S. Appl. No. 17/245,611 dated Jun. 14, 2023.
Abe-Suzuki et al., CXCL12+ stromal cells as bone marrow niche for CD34+ hematopoietic cells and their association with disease progression in myelodysplastic syndromes, Laboratory Investigation, 94, 1212-1223, 2014 (published online: Sep. 8, 2014); DOI:10.1038/labinvest.2014.110.
Clinical Trial NCT05187182, "CA-4948 in Combination With FOLFOX/PD-1 Inhibitor +/− Trastuzumab for Untreated Unresectable Gastric and Esophageal Cancer," last update posted Jan. 15, 2025. Available at: https://clinicaltrials.gov/study/NCT05187182.
Clinical Trial NCT05669352, "A Study of Oral IRAK-4 Inhibitor CA-4948 in Combination With Pembrolizumab and Stereotactic Radiosurgery in Patients With Melanoma Brain Metastases," last update posted Apr. 4, 2025. Available at: https://clinicaltrials.gov/study/NCT05669352.
Clinical Trial NCT06439836, "Pembrolizumab Plus CA-4948 for the Treatment of Patients With Progressive Metastatic Urothelial Cancer Despite Prior Immunotherapy," last update posted Mar. 10, 2025. Available at: https://clinicaltrials.gov/study/NCT06439836.
Doonan, "Novel oral IRAK-4 inhibition plus checkpoint inhibition in metastatic melanoma," Hematology and Oncology 2022. Available at https://web.archive.org/web/20220703052454/https://discovery.education.med.ufl.edu/hematology-and-oncology-2022/.
Garcia-Manero et al., "Research and Clinical Updates on IRAK4 and Its Roles in Inflammation and Malignancy: Themes and Highlights from the 1st Symposium on IRAK4 in Cancer." Frontiers in Hematology 3 (2024): 1339870.
Gorecki et al., "Strategies for the treatment of acute myeloid leukemia with FLT3 mutations: a patent review," Expert Opinion on Therapeutic Patents 35.2 (2025): 137-164.
International Search Report and Written Opinion for International Application No. PCT/US25/15585 dated Jun. 12, 2025.
International Search Report and Written Opinion for International Application No. PCT/US25/21962 dated Jul. 10, 2025.
Shi et al., The Role of the CXCL12/CXCR4/CXCR7 Chemokine Axis in Cancer, Frontiers in Pharmacology, 11, 574667, Dec. 8, 2020; DOI: 10.3389/fphar.2020.574667.
Xiong et al., Reduced miR-16 levels are associated with VEGF upregulation in high-risk myelodysplastic syndromes, Journal of Cancer, 12(7), 1967-1977, 2021 (published: Jan. 30, 2021); DOI: 10.7150/jca.52455.
Zhang et al., CircRNA-miRNA-VEGFA: an important pathway to regulate cancer pathogenesis, Frontiers in Pharmacology, 14, 1049742, May 10, 2023; DOI: 10.3389/fphar.2023.1049742.
Zhao et al., Vascular endothelial growth factor-A is expressed both on lymphoma cells and endothelial cells in angioimmunoblastic T-cell lymphoma and related to lymphoma progression, Laboratory Investigation, 84, 1512-1519, 2004 (published: Aug. 16, 2004); DOI: 10.1038/labinvest.3700145.
Bennett et al., "IRAK1 and IRAK4 as emerging therapeutic targets in hematologic malignancies." Current Opinion in Hematology, vol. 29, No. 1, p. 8 (2022).
Booher et al., "Preclinical activity of IRAK4 kinase inhibitor CA-4948 alone or in combination with targeted therapies and preliminary phase 1 clinical results in non-Hodgkin lymphoma." Blood, vol. 132, No. 4168 (2018).
Gao et al., "Inhibition of IL-1 Receptor-Associated Kinase 1 Decreases Murine Acute Graft-versus-Host Disease While Preserving the Graft-versus-Lymphoma Effect." Transplantation and Cellular Therapy, vol. 28, No. 3, pp. 134-e1.(2022).
Gupta et al., "Interleukin-1-receptor kinase 4 inhibition: achieving immunomodulatory synergy to mitigate the impact of COVID-19." Frontiers in Immunology, vol. 12, No. 693085. (2021).
International Search Report and Written Opinion for Application No. PCT/US2023/021812 dated Aug. 6, 2023.
McElroy, "Interleukin-1 receptor-associated kinase 4 (IRAK4) inhibitors: an updated patent review (2016-2018)." Expert opinion on therapeutic patents, vol. 29, No. 4, pp. 243-259.(2019).
Von Roemeling, "IRAK-4 as a therapeutic target in primary CNS lymphoma", University of Florida, Curis, Presentation 28 slides (2022).
Zhang et al "Canonical NF-KB Signalling Is a Potential Target in FLT3/ITD AML." Blood, vol. 120, No. 21, p. 2447 (2012).
Booher et al., "Combination of IRAK4 Inhibitor CA-4948 with BCL2 Inhibitor Venetoclax Induces Tumor Regression in an ABC-DLBCL Xenograft Model", Blood, 130(1): 1534, (2017).
International Search Report and Written Opinion for Application No. PCT/US2022/017902 dated Aug. 3, 2022.
Issue Notification for U.S. Appl. No. 16/498,866 dated Aug. 3, 2022.
Rhyasen., "IRAK family kinases as therapeutic targets for Myelodysplastic Syndrome and Acute Myeloid Leukemia" University of Cincinnati: 132 pages (2014).
Blackmon et al., "Test then erase? Current status and future opportunities for Measurable Residual Disease testing in Acute Myeloid Leukemia", Acta Haematologica, pp. 1-14, (2023).
Burguera et al., "Trial in Progress: A Phase 1b Single-Arm, Open-Label Study of Emavusertib (CA-4948) in Combination with Azacitidine and Venetoclax in Acute Myeloid Leukemia Patients in Complete Response with Measurable Residual Disease." Blood 142 (2023): 5975.
D'Angelo, "Targeting IRAK4 as Novel Therapy in Primary CNS Lymphoma," University of Nebraska Medical Center, Published Aug. 7, 2024: 13 slides.
De la Fuente et al. "A phase 1 single-arm, open-label study of emavusertib (CA-4948) in combination with azacitidine and venetoclax in patients (pts) with acute myeloid leukemia (AML) in complete response (CR) with measurable residual disease (MRD)." Poster at 2024 American Society of Clinical Oncology Meeting. Published Jun. 3, 2024.
Extended European Search Report for EP Application No. 21852519.4 dated Aug. 1, 2024.
Extended European Search Report for EP Application No. 21895491.5 dated Aug. 27, 2024.
Extended European Search Report for EP Application No. 23214923.7 dated Jun. 5, 2024.

(56) References Cited

OTHER PUBLICATIONS

Giménez et al., "Targeting IRAK4 disrupts inflammatory pathways and delays tumor development in chronic lymphocytic leukemia." Leukemia 34.1 (2020): 100-114.
Grommes et al., "Emavusertib (CA-4948) in Combination with Ibrutinib in Relapsed/Refractory Primary Central Nervous System Lymphoma (R/R PCNSL) patients." American Society of Clinical Oncology. (2024).
International Search Report and Written Opinion for Application No. PCT/US24/31970 dated Jul. 18, 2024.
International Search Report and Written Opinion for International Application No. PCT/US24/31972 dated Aug. 26, 2024.
Metzeler et al., "Predictive biomarkers of response to the IRAK4/FLT3 inhibitor emavusertib in hematological malignancies." American Society of Clinical Oncology. (2024).
Wiese et al., "Investigational IRAK-4 inhibitors for the treatment of rheumatoid arthritis." Expert opinion on investigational drugs 29.5 (2020): 475-482.
Winer et al., "Preliminary Safety, Efficacy and Molecular Characterization of Emavusertib (CA-4948) in Relapsed/Refractory (R/R) Acute Myeloid Leukemia (AML) Patients with FLT3 Mutation (FLT3m)" American Society of Clinical Oncology. (2024).
Abu-Duhier et al., "FLT3 internal tandem duplication mutations in adult acute myeloid leukemia define a high-risk group," British Journal of Haematology, 111: 190-195 (2000).
Alder, C. M. et al., "Identification of a Novel and Selective Series of Itk Inhibitors via a Template-Hopping Strategy", *Med. Chem. Lett.*, 4:948-952 (American Chemical Society, 2013).
Bains et al., "FLT3 and NPM1 Mutations in Myelodysplastic Syndromes: Frequency and Potential Value for Predicting Progression to Acute Myeloid Leukemia," American Journal of Clinical Pathology, 135(1): 62-69 (2011).
Balasubramanian et al., "Abstract 3646: Novel IRAK-4 inhibitors exhibit highly potent anti-proliferative activity in DLBCL cell lines with activating MYD88 L265P mutation," Cancer Research, 75(15 Suppl):Abstract 3646 (2015).
Bhagat et al., "Abstract 2570: IMO-8400, a selective antagonist of TLRs 7, 8 and 9, inhibits MYD88 L265P mutation-driven signaling and cell survival: A potential novel approach for treatment of B-cell lymphomas harboring MYD88 L265P mutation," Cancer Res, 74(19): 2570 (3 pages) (2014).
Booher et al., "Combination of IRAK4 (CA-4948) and BTK (Vecabrutinib) Inhibitors Show Superior Efficacy in Preclinical Models of ABC DLBCL Tumors Containing MYD88-L265P Mutations," Hematological Oncology, 37(S2): 512-512 (2019).
Chen et al., "Design and Synthesis of a Series of Non-Peptide High-Affinity Human Corticotropin-Releasing Factor1 Receptor Antagonists," J Med Chem, 39:4358-4360 (1996).
Chen et al., "Design and synthesis of lmidazo[1,2-b]pyridazine IRAK4 inhibitors for the treatment of mutant MYD88 L265P diffuse large B-cell lymphoma," Eur J Med Chem, 190: 11209 (33 pages) (2020).
Choudhary et al., "Abstract 127: Efficacy of novel IRAK4 inhibitor CA4948 in AML and MDS," Proceedings of the American Association for Cancer Research Annual Meeting 2017; Apr. 1-5, 2017; Washington, DC. Philadelphia (PA): AACR; Cancer Res 2017;77(13 Suppl):Abstract 127 (2017).
Choudhary et al., "SF3B1 Mutations Induce Oncogenetic IRAK4 Isoforms and Activate Targetable Innate Immune Pathways in MDS and AML," Blood, 134(Supplement 1): 4224 (5 pages) (2019).
Clinical study NCT04278768 (V3), "An Open Label Dose Escalation Trial of CA-4948 in Patients With Acute Myelogenous Leukemia or Myelodysplastic Syndrome," Clinical Trials (6 pages) (2020).
Curis Corporate Presentation, NASDAQ:CRIS, Jul. 1, 2020.
Curis Inc. First Quarter 2020 Financial Results, May 12, 2020.
Curis, "Dec 2020 Key Opinion Leader Event," (22 pages) (2020).
Dadabayev, "DAKA nVision+ System, Peroxidase," Biocompare, (7 pages) (2004).
Das et al., "Effects of Positional and Geometrical isomerism on the Biological Activity of Some Novel Oxazolidinones," Bioorg Med Chem Lett, 15:337-343 (2005).
Das et al., "Impact Analysis of SARS-CoV2 on Signaling Pathways During COVID19 Pathogenesis Using Codon Usage Assisted Host-Viral Protein Interactions," BioRxiv, (27 pages) (2020).
Davids et al., "Phase I First-in-Human Study of Venetoclax in Patients With Relapsed or Refractory Non-Hodgkin Lymphoma," J Clin Oncol, 35(8): 826-833 (2015).
Doonan et al., "CA-4948 for the treatment of melanoma brain metastasis," Central Nervous System Tumors: 1 page (Published Apr. 16, 2022).
Ex Parte Cao, Decision rendered by the Board of Patent Appeals and Interferences in U.S. Appl. No. 10/696,862 on Sep. 21, 2011.
Extended European Search Report for EP Application No. 18777745.3 mailed Jul. 27, 2020.
Extended European Search Report for EP Application No. 18873778.7 dated Jul. 23, 2021.
Extended European Search Report for EP Application No. 20211096.1 dated Feb. 12, 2021.
Extended European Search Report issued by the European Patent Office in corresponding Application No. EP 16823970 issued Jun. 25, 2019.
Extended European Search Report issued by the European Patent Office in corresponding Application No. EP 18190333 issued Mar. 13, 2019.
Extended European Search Report issued by the European Patent Office in corresponding Application No. PCT/IB2015054620 dated Jan. 16, 2018.
Extended European Search Report issued by the European Patent Office in corresponding International Application No. PCT/IB2015/050217, dated May 2, 2017.
Extended European Search Report received for EP Patent Application No. 16823968, mailed Dec. 10, 2018.
Faison, "Curis: Differentiated IRAK4 Inhinitor To Drive Value Creation in the Near Term," Seeking Alpha, Mar. 1, 2021.
Fathi et al., "Treatment of FLT3-ITD acute myeloid leukemia," Am. J. Blood. Res., 1(2): 175-189 (2011).
Garcia-Manero et al., "2863 A Phase 1, Open Label Dose Escalation Trial Evaluating the Safety, Pharmacokinetics, Pharmacodynamics, and Clinical Activity of Orally Administered CA-4948 in Patients with Acute Myelogenous Leukemia or Myelodysplastic Syndrome," Abstract, ASH Annual Meeting (4 pages)(2020).
Garcia-Manero et al., "A Phase 1, Dose Escalation Trial With Novel Oral IRAK4 Inhibitor CA-4948 In Patients With Acute Myelogenous Leukemia or Myelodysplastic Syndrome—Interim Report," Curis Inc. Presentation published Jun. 11, 2021 (22 pages).
Garcia-Manero., "Spliceosome Mutations, IRAK4 and CA-4948 in MDS and AML," Curis Inc. Presentation published Apr. 24, 2021 (22 pages).
Genung et al., "Chapter Four—Small Molecule Inhibition of Interleukin-1 Receptor-Associated Kinase 4 (IRAK4)," Progress in Medicinal Chemistry, 56: 117-163 (2017).
Gerecitano et al., "A Phase 1 Study of Venetoclax (ABT-199/GDC-0199) Monotherapy in Patients with Relapsed/Refractory Non-Hodgkin Lymphoma," Blood, 126(23):254 (2015).
Golub et al., "Molecular classification of cancer: Class discovery and class prediction by gene expression monitoring," Science, 286: 531-537 (1999).
Huang et al., "Posttranslational modifications of NF-kappaB: another layer of regulation for NF-kappaB signaling pathway," Cell Signalling, 22(9): 1282-90 (2010).
International Search Report and Written Opinion for International Application No. PCT/IB2016/054203 mailed Sep. 23, 2016.
International Search Report and Written Opinion for International Application No. PCT/IB2016/054229 mailed Nov. 15, 2016.
International Search Report and Written Opinion for International Application No. PCT/US/2018/058194 mailed Feb. 3, 2019.
International Search Report and Written Opinion for International Application No. PCT/US2021/030192 mailed Jun. 25, 2021.
International Search Report and Written Opinion for International Application No. PCT/US2021/059668 mailed Feb. 24, 2022.

(56) References Cited

OTHER PUBLICATIONS

International Search Report from parent PCT application PCT/IB2015/050217 dated Apr. 29, 2015.
International Search Report from parent PCT application PCT/IB2015/054620 dated Oct. 19, 2015.
International Search Report from published parent PCT application PCT/IB2015/050119 dated Mar. 19, 2015.
Kelly et al., "Selective interleukin-1 receptor-associated kinase 4 inhibitors for the treatment of autoimmune disorders and lymphoid malignancy," J Exp Med, 212(13): 2189-2201 (2015).
Knapper et al., "An evaluation of the tyrosine kinase inhibitor pacritinib in patients with relapsed FLT3-mutated acute myeloid leukaemia (the UK NCRI AML17 study)," Haematologica, 101(1): 40 (2016).
Lala at al., "Role of nitric oxide in tumor progression: Lessons from experimental tumors," Cancer and Metastasis Reviews, 17(1):91-106 (1998).
Landgren et al., "MYD88 and beyond: novel opportunities for diagnosis, prognosis and treatment in Waldenström's Macroglobulinemia," Leukemia, 28(9): 1799-1803 (2014).
Lane, "IRAK4 inhibition in AML, MDS and B cell Cancers," Curis Presentation Published Sep. 29, 2021.
Lange et al., "Preclinical evaluation of a novel interleukin-1 receptor-associated kinase 4 (IRAK4) inhibitor in combination with PI3K inhibitor copanlisib or BTK inhibitors in ABC-DLBCL," Abstract, Cancer Res, 78(13) (5 pages) (2018).
Li et al., "Inhibition of IRAK1/4 sensitizes T cell acute lymphoblastic leukemia to chemotherapies," Journal of Clinical Investigation, 125(3): 1081-1097 (2015).
Li et al., "Synergistic induction of apoptosis in high-risk DLBCL by BCL2 inhibition with ABT-199 combined with pharmacologic loss of MCL1," Leukemia, 29:1702-1712 (2015).
Nowakowski et al., "# 2945: A Multi-Center, Dose-Finding Study to Assess Safety, Tolerability, Pharmacokinetics and Preliminary Efficacy of a novel IRAK4 inhibitor CA-4948 in combination with ibrutinib, in Patients with Relapsed or Refractory Hematologic Malignancies," American Society of Hematology, Presentation by Curis Inc. published on Nov. 19, 2020 (12 pages).
Nowakowski et al., "703 Safety, Pharmacokinetics and Activity of CA-4948, an IRAK4 Inhibitor, for Treatment of Patients with Relapsed or Refractory Hematologic Malignancies: Results from the Phase 1 Study," Abstract, ASH Annual Meeting (6 pages) (2020).
Partial Search Report and Written Opinion for EP Patent Application No. EP16823970, mailed Mar. 19, 2019.
Rao et al., "Abstract C191: Efficacy of novel IRAK4 inhibitors in ABC-DLBCL and AML models," Proceedings of the AACR-NCI-EORTC International Conference: Molecular Targets and Cancer Therapeutics; Nov. 5-9, 2015; Boston, MA. Philadelphia (PA): AACR; Mol Cancer Ther,14(12 Suppl 2):Abstract C191 (2015).
Rao Gummadi et al., "Discovery of CA-4948, an Orally Bioavailable IRAK4 Inhibitor for Treatment of Hematologic Malignancies," ACS Medicinal Chemistry Letters: 8 pages (2020).
Santa Cruz Biotechnology, "p-NFkB p50 (A-8): sc-271908," (1 page) (2012).
STN Registry database entry: [online] 2011, CAS RN 1301085-08-4 (Search date: Feb. 9, 2019).
STN Registry database entry: [online] 2011, CAS RN 1421459-19-9 (Search date: Feb. 9, 2019).
STN Registry database entry: [online] 2011, CAS RN 1421491-68-0 (Search date: Feb. 9, 2019).
STN Registry database entry: [online] 2011, CAS RN 1421497-05-3 (Search date: Feb. 9, 2019).
STN Registry database entry: [online] 2014, CAS RN 1178067-91-8 (Search date: Feb. 9, 2019).
STN Registry database entry: [online] 2014, CAS RN 1184469-61-1 (Search date: Feb. 9, 2019).
STN Registry database entry: [online] 2014, CAS RN 1223638-97-8 (Search date: Feb. 9, 2019).
STN Registry database entry: [online] 2014, CAS RN 1252319-44-0 (Search date: Feb. 9, 2019).
STN Registry database entry: [online] 2014, CAS RN 1274105-18-8 (Search date: Feb. 9, 2019).
STN Registry database entry: [online] 2014, CAS RN 1282974-67-7 (Search date: Feb. 9, 2019).
STN Registry database entry: [online] 2014, CAS RN 1333957-90-6 (Search date: Feb. 9, 2019).
STN Registry database entry: [online] 2014, CAS RN 1346410-97-6 (Search date: Feb. 9, 2019).
STN Registry database entry: [online] 2014, CAS RN 1367793-38-1 (Search date: Feb. 9, 2019).
STN Registry database entry: [online] 2014, CAS RN 1368333-88-3 (Search date: Feb. 9, 2019).
STN Registry database entry: [online] 2014, CAS RN 1369195-81-2 (Search date: Feb. 9, 2019).
STN Registry database entry: [online] 2014, CAS RN 1381262-66-3 (Search date: Feb. 9, 2019).
STN Registry database entry: [online] 2014, CAS RN 1381667-74-0 (Search date: Feb. 9, 2019).
STN Registry database entry: [online] 2014, CAS RN 1396710-33-0 (Search date: Feb. 9, 2019).
STN Registry database entry: [online] 2014, CAS RN 1405289-53-3 (Search date: Feb. 9, 2019).
STN Registry database entry: [online] 2014, CAS RN 1414842-47-9 (Search date: Feb. 9, 2019).
STN Registry database entry: [online] 2014, CAS RN 1414842-48-0 (Search date: Feb. 9, 2019).
STN Registry database entry: [online] 2014, CAS RN 1421504-43-9 (Search date: Feb. 9, 2019).
STN Registry database entry: [online] 2014, CAS RN 1421508-39-5 (Search date: Feb. 9, 2019).
STN Registry database entry: [online] 2014, CAS RN 1423498-44-5 (Search date: Feb. 9, 2019).
STN Registry database entry: [online] 2014, CAS RN 1522249-43-9 (Search date: Feb. 9, 2019).
STN Registry database entry: [online] 2014, CAS RN 1548563-20-7 (Search date: Feb. 9, 2019).
STN Registry database entry: [online] 2014, CAS RN 1570255-99-0 (Search date: Feb. 9, 2019).
STN Registry database entry: [online] 2014, CAS RN 1575185-05-5 (Search date: Feb. 9, 2019).
STN Registry database entry: CAS RN 1181327-83-2 (Entered STN: Sep. 8, 2009). (Year: 2009).
STN Registry database entry: CAS RN 1301085-08-4 (Entered STN: May 26, 2011). (Year: 2011).
Sun et al., "Synthesis, in Vitro Evaluation and Cocrystal Structure of 4-Oxo-[1]benzopyrano[4,3-c]pyrazole Cryptosporidium parvum Inosine 5'-Monophosphate Dehydrogenase (CpIMPDH) Inhibitors," J Med Chem, 57:10544-10550 (2014).
Takami et al., "Design and synthesis of Rho kinase inhibitors (I)," Bioorg Med Chem, 12:2115-2137 (2004).
Ugolkov et al., "Identification of NF-kappaB phospho-p50 as a predictive biomarker for IRAK4 inhibitor CA-4948 in patients with Non-Hodgkin's lymphoma," American Associates for Cancer Research, published on Nov. 19, 2020 (1 page).
Ugolkov et al., "Identification of NF-kB phospho-p50 as a potential predictive biomarker for IRAK4 inhibitor CA-4948 in patients with Non-Hodgkin's lymphoma," AACR Annual Meeting 2021, Poster No. 385.
Viatour et al., "Phosphorylation of NF-kappaB and IkappaB proteins: implications in cancer and inflammation," Trends Biochem Sci, 30(1): 43-52 (2005).
Von Roemeling et al., "The IRAK4 inhibitor CA-4948 demonstrates antitumor activity in a preclinical model of CNS lymphoma," Molecular Targets and Cancer Therapeutics, Curis Presentation published Oct. 7, 2021 (9 pages).
Wang et al., "Crystal Structures of IRAK-4 Kinase in Complex with Inhibitors: A Serine/Threonine Kinase with Tyrosine as a Gatekeeper," Structure 14, 1835-1844 (2006).

(56) References Cited

OTHER PUBLICATIONS

Younes et al., "Phase 1 Dose-Finding Study Investigating CA-4948, an IRAK4 Kinase Inhibitor, in Patients with R/R NHL: Report of Initial Efficacy and Updated Safety Information," Blood, 134(1): 5327 (3 pages) (2019).
Yu et al., "Targeting NF-kB pathway for the therapy of diseases: mechanism and clinical study," Sig Transduct Target Ther, 5(209) (23 pages) (2020).
Zhang et al., "Design, synthesis and evaluation of bicyclic benzamides as novel 5-HT1F receptor agonists," Bioorg Med Chem Lett, 14(24):6011-6016 (2004).
Zhang et al., "Innate immune mediator, Interleukin-1 receptor accessory protein (IL1RAP), is expressed and pro-tumorigenic in pancreatic cancer," Journal of Hematology & Oncology, 15: Article 70 pp. 1-5 (2022).
Anonymous, "Chronic myelomonocytic leukaemia", Leukaemia Foundation, Retrieved from the Internet: https://www.leukaemia.org.au/blood-cancer/myelodysplastic-syndromes/chronic-myelomonocytic-leukaemia/, pp. 1-2 (2019).
Extended European Search Report for EP Application No. 23173240.5 dated Nov. 11, 2023.
Arranz et al., "Interleukin-1 [beta] as emerging therapeutic target in hematological malignancies and potentially in their complications." Blood Reviews 31(5) (2017): 306-317.
Bai et al., "The recent advance of Interleukin-1 receptor associated kinase 4 inhibitors for the treatment of inflammation and related diseases," European Journal of Medicinal Chemistry 258 (2023): 15606.
Blood Cancer UK, "Relapse and refractory AML treatments," Retrieved on Nov. 15, 24 from: https://bloodcancer.org.uk/understanding-blood-cancer/leukaemia/acute-myeloid-leukaemia/aml-treatment/relapse-refractory/.
Chen et al., "Immediate early response 3 gene promotes aggressive progression and autophagy of AML by negatively regulating AKT/mTOR." Translational Oncology 35 (2023): 101711.
Day et al., "Interleukin-1 blockade with anakinra in acute leukaemia patients with severe COVID-19 pneumonia appears safe and may result in clinical improvement." British Journal of Haematology 190(2) (2020): e80.
Extended European Search Report for EP Application No. 24168755.7 dated Oct. 10, 2024.
Grommes et al., "Analysis of genetic mutation profile and CNS pharmacokinetics in relapsed/refractory primary CNS lymphoma patients responding to novel emavusertib (IRAK4i) and BTKi combination ," Abstract. Jan. 27, 2025.
Guidetti et al., "Targeting IRAK4 with emavusertib in lymphoma models with secondary resistance to PI3K and BTK inhibitors." Journal of Clinical Medicine 12 (2023): 399.
International Search Report and Written Opinion for International Application No. PCT/US24/52925 dated Feb. 6, 2025.
Parrondo et al., "IRAK-4 inhibition: emavusertib for the treatment of lymphoid and myeloid malignancies." Frontiers in Immunology 14 (2023): 1239082.
Pleyer et al., "Azacitidine for Front-Line Therapy of Patients with AML," International Journal of Molecular Sciences 18 (2017): 415 (18 pages).
Smith et al., "Alternative Splice Variants of IRAK4 That Activate Innate Immune Signaling Are Associated with U2AF1 Mutations in Myelodysplastic Syndrome and Acute Myeloid Leukemia," Blood 128.22 (2016): 1531. Abstract.
Supplementary European Search Report for EP Application No. 22785128.4 dated Jan. 27, 2025.
Ugolkov et al., "IRAK4 inhibitor CA-4948 potentiates antitumor effects of azacitidine and venetoclax in human acute myeloid leukemia", Curis. EHA 2021, Jun. 9-17, 2021.
Ugolkov et al., "IRAK4 inhibitor CA-4948 potentiates antitumor effects of azacitidine and venetoclax in human acute myeloid leukemia", HemaSphere, vol. 5, Suppl. 2, 26th Congress of the European Hematology Association, EHA 2021 Jun. 9, 2021 to Jun. 17, 2021, Jul. 1, 2021.
Zhang et al.,. "Constitutive IRAK4 activation underlies poor prognosis and chemoresistance in pancreatic ductal adenocarcinoma." Clinical Cancer Research 23(7) (2017): 1748-1759.
Ambady et al., "Relapsed and refractory primary CNS lymphoma: treatment approaches in routine practice." Annals of Lymphoma 5 (2021): 23.
Ambinder et al., "Navigating the contested borders between myelodysplastic syndrome and acute myeloid leukemia." Frontiers in Oncology 12 (2022): 1033534.
Garattini et al., "Drug holidays and overall survival of patients with metastatic colorectal cancer." Cancers 13 (2021): 3504.
Garcia et al., "Safety and efficacy of decitabine plus ipilimumab in relapsed or refractory MDS/AML in the post-BMT or transplant naïve settings." Blood (2020) 136 (Supplement 1) : 15.
Garcia-Manero et al., "S129: Takeaim LEUKEMIA-a phase 1/2A study of the IRAK4 inhibitor emavusertib (CA-4948) as monotherapy or in combination with azacitidine or venetoclax in relapsed/refractory AML or MDS." HemaSphere 6 (2022): 30-31.
Lee et al., "A molecular dynamics simulation study for variant drug responses due to FMS-like tyrosine kinase 3 G697R mutation." RSC Advances 7 (2017): 29871-29881.
Pubchem, CID 5329102 "Sunitinib", Jan. 30, 2006.
Supplementary European Search Report for EP Application No. 15809538.0 dated Jan. 16, 2018.
Supplementary European Search Report for EP Application No. 16823968.9 dated Dec. 10, 2018.
Thol et al., "How I treat refractory and relapsed acute myeloid leukemia." Blood 143 (2024): 11-20.

* cited by examiner

FIG. 1

| Kinase | $K_d$ (nM) |
|---|---|
| IRAK4 | 23 |
| IRAK1 | 100-1,000 |
| FLT3 | 31 |
| FLT3 (D835H) | 4.6 |
| FLT3 (D835V) | 44 |
| FLT3 (D835Y) | 2.5 |
| FLT3 (ITD) | 7.8 |
| FLT3 (ITD, D835V) | 31 |
| FLT3 (ITD, F691L) | 20 |
| FLT3 (K663Q) | 47 |
| FLT3 (N841I) | 16 |

COMPOUNDS AND COMPOSITIONS FOR TREATING HEMATOLOGICAL DISORDERS

CROSS-REFERENCE TO RELATED APPLICATIONS

This application is a continuation of U.S. application Ser. No. 16/498,866, filed Sep. 27, 2019, which is the 371 U.S. National-Stage application of PCT/IB2018/052232, filed Mar. 30, 2018, which claims the benefit of priority to Indian Provisional Patent Application serial number 201741011785, filed Mar. 31, 2017, the contents of each of which are hereby incorporated by reference herein in their entirety.

BACKGROUND

Acute myeloid leukemia (hereafter also referred to as "AML") is a hematological malignancy with a poor prognosis that often occurs in adults, and the 5-year survival rate thereof is predicted to be 20%. At present, it is possible to temporarily reduce the number of AML cells to a level below the detection limit through AML treatment. This condition is referred to as "complete remission." However, AML often recurs after achieving complete remission, and for many patients, recurrent AML results in death. In particular, a very low survival rate in cases of recurrence has been a serious issue of concern. Accordingly, there is a need for new treatments for AML.

SUMMARY

Provided herein is a method of treating or preventing acute myeloid leukemia in a subject, comprising administering a compound of Formula (I):

(I)

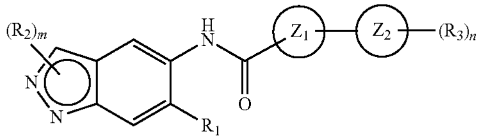

or a pharmaceutically acceptable salt thereof;

wherein,

- Ring $Z_1$ is an optionally substituted heteroaryl;
- Ring $Z_2$ is a optionally substituted heterocycloalkyl, optionally substituted heteroaryl or a direct bond;
- $R_1$ is alkyl, cyano, —$NR_aR_b$, or optionally substituted groups selected from cycloalkyl, aryl or heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, —OCO—$CH_2$—O-alkyl, —OP(O)(O-alkyl)$_2$ or —$CH_2$—OP(O)(O-alkyl)$_2$;
- $R_2$, at each occurrence, independently is an optionally substituted group selected from alkyl or cycloalkyl; wherein the substituent, at each occurrence, is independently halogen, alkoxy, hydroxyl, hydroxyalkyl, haloalkyl or haloalkoxy;
- $R_3$, at each occurrence, independently is hydrogen, halogen, alkyl, haloalkyl, haloalkoxy, alkoxy, —$NR_aR_b$, hydroxyl or hydroxyalkyl;
- $R_a$ is hydrogen or alkyl;
- $R_b$ is hydrogen, alkyl, acyl, hydroxyalkyl, —$SO_2$-alkyl or optionally substituted cycloalkyl;
- 'm' and 'n' are independently 1 or 2.

Provided herein is a method of treating or preventing acute myeloid leukemia in a subject, comprising administering a compound of Formula (II):

(II)

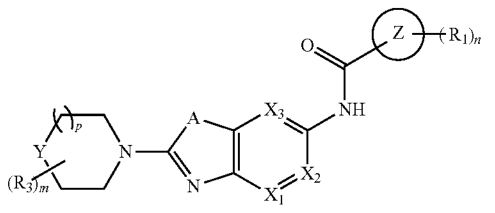

or a pharmaceutically acceptable salt thereof;

wherein,

- $X_1$ and $X_3$ independently are CH or N; $X_2$ is $CR_2$ or N; provided one and not more than one of $X_1$, $X_2$ or $X_1$ is N;
- A is O or S;
- Y is —$CH_2$— or O;
- Ring Z is aryl or heterocyclyl;
- $R_1$, at each occurrence, is independently halo or optionally substituted heterocyclyl; wherein the substituent is alkyl, alkoxy, aminoalkyl, halo, hydroxyl, hydroxyalkyl or —$NR_aR_b$;
- $R_2$ is hydrogen, optionally substituted cycloalkyl, optionally substituted aryl, optionally substituted heterocyclyl or —$NR_aR_b$; wherein the substituent is alkyl, amino, halo or hydroxyl;
- $R_3$, at each occurrence, is alkyl or hydroxyl;
- $R_a$ and $R_b$ are independently hydrogen, alkyl, acyl or heterocyclyl;
- 'm' and 'n' are independently 0, 1 or 2;
- 'p' is 0 or 1.

Provided herein is a method of treating or preventing acute myeloid leukemia in a subject, comprising administering a compound of Formula (III):

(III)

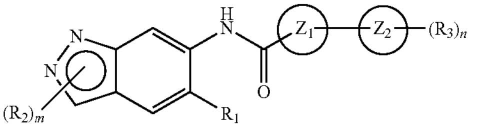

or a pharmaceutically acceptable salt thereof;

wherein,

- $Z_1$ is optionally substituted cycloalkyl, optionally substituted aryl, optionally substituted heterocyclyl or is absent;
- $Z_2$ is optionally substituted cycloalkyl, optionally substituted aryl or optionally substituted heterocyclyl;
- $R_1$ is hydrogen, optionally substituted alkyl, amino, halo, cyano, optionally substituted cycloalkyl, optionally substituted aryl, optionally substituted heterocyclyl, optionally substituted arylalkyl or optionally substituted heterocyclylalkyl;
- $R_2$ at each occurrence is amino, optionally substituted alkyl, optionally substituted cycloalkyl, optionally substituted aryl, optionally substituted heterocyclyl, optionally substituted arylalkyl or optionally substituted heterocyclylalkyl;

$R_3$ at each occurrence is hydroxy, halo, optionally substituted alkyl, optionally substituted alkoxy, optionally substituted cycloalkyl or —$NR_aR_b$;

$R_a$ and $R_b$, independently for each occurrence, are hydrogen, optionally substituted alkyl, optionally substituted acyl, optionally substituted cycloalkyl, optionally substituted aryl, optionally substituted heterocyclyl, optionally substituted arylalkyl or optionally substituted heterocyclylalkyl;

m, at each occurrence, is 0, 1 or 2; and n, at each occurrence, is 0, 1, or 2.

In some embodiments, disclosed herein is a use of a compound disclosed herein or a pharmaceutically acceptable salt or a stereoisomer thereof for the treatment and prevention of AML.

In some embodiments, disclosed herein is a use of compound disclosed herein or a pharmaceutically acceptable salt or a stereoisomer thereof, including mixtures thereof in all ratios, as a medicament for treating AML.

BRIEF DESCRIPTION OF THE FIGURES

FIG. 1 depicts the binding $K_d$ of Compound A to various kinases, including FLT-3 wild-type and mutations thereof.

DETAILED DESCRIPTION

Figure 2A:
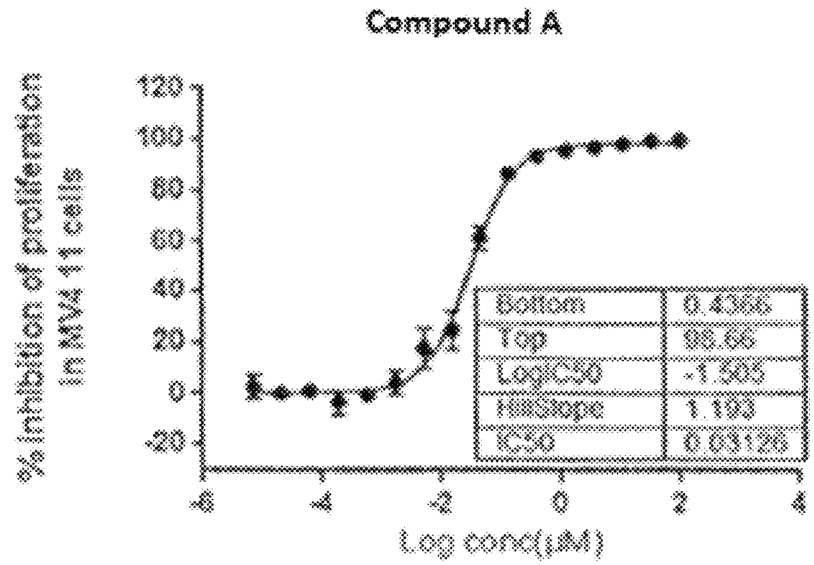
FIG. 2A depicts the % inhibition of proliferation in MV4-11 cells by Compound A.

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

The singular forms "a", "an" and "the" encompass plural references unless the context clearly indicates otherwise.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, alkoxyalkyl, halogen, alkyl, aryl, aryloxy, aralkyl, heteroaryl, heteroaryloxy, heteroaralkyl, cycloalkyl, cycloalkoxy, (cycloalkyl)alkyl, heterocyclyl, (heterocyclyl) alkyl, amino, aminoalkyl, alkylamino, dialkylamino, acyl, —$C(O)_2H$, —O(acyl), —NH(acyl), —N(alkyl)(acyl), cyano, phosphinate, phosphate, phosphonate, sulfonate, sulonamido, sulfate, haloalkyl or haloalkoxy. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

The term "substituted" refers to moieties having substituents replacing hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and un substituted variants.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" refers to a group R—CO— wherein R is an optionally substituted alkyl group defined above. Examples of 'acyl' groups are, but not limited to, $CH_3CO$—, $CH_3CH_2CO$—, $CH_3CH_2CH_2CO$— or $(CH_3)_2CHCO$—.

As used herein, the term "alkoxy" refers to a straight or branched, saturated aliphatic $C_1$-$C_{10}$ hydrocarbon radical bonded to an oxygen atom that is attached to a core structure. Preferably, alkoxy groups have one to six carbon atoms. Examples of alkoxy groups include but are not limited to methoxy, ethoxy, propoxy, isopropoxy, butoxy, isobutoxy, tert-butoxy, pentoxy, 3-methyl butoxy and the like.

As used herein, the term "haloalkyl" refers to alkyl group (as defined above) is substituted with one or more halogens. A monohaloalkyl radical, for example, may have a chlorine, bromine, iodine or fluorine atom. Dihalo and polyhaloalkyl radicals may have two and more of the same or different halogen atoms respectively. Examples of haloalkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl, difluoropropyl and the like.

As used herein, the term "haloalkoxy" refers to radicals wherein one or more of the hydrogen atoms of the alkoxy group are substituted with one or more halogens. Representative examples of "haloalkoxy" groups include, but not limited to, difluoromethoxy (—$OCHF_2$)), trifluoromethoxy (—$OCF_3$) or trifluoroethoxy (—$OCH_2CF_3$).

As used herein, the term "aryl" alone or in combination with other term(s) means a 6- to 10-membered carbocyclic aromatic system containing one or two rings wherein such rings may be fused. The term "fused" means that the second ring is attached or formed by having two adjacent atoms in common with the first ring. The term "fused" is equivalent to the term "condensed". Examples of aryl groups include but are not limited to phenyl, naphthyl or indanyl. Unless otherwise specified, all aryl groups described herein may be optionally substituted.

The terms "amine" and "amino" are art-recognized and refer to both unsubstituted and substituted amines and salts thereof, e.g., a moiety that can be represented by

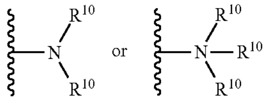

wherein each $R^{10}$ independently represents a hydrogen or a hydrocarbyl group, or two $R^{10}$ are taken together with the N atom to which they are attached complete a heterocycle having from 4 to 8 atoms in the ring structure.

As used herein, "aminoalkyl" refers to an amino group, as defined above, in which one or two hydrogen atoms are substituted with alkyl group.

As used herein, "nitro" refers to an —$NO_2$ group.

As used herein, "alkylamino" and "cycloalkylamino", refer to an —N-group, wherein nitrogen atom of said group being attached to alkyl or cycloalkyl respectively. Representative examples of an "Alkylamino" and "Cycloalkylamino" groups include, but are not limited to —$NHCH_3$ and —NH-cyclopropyl. An amino group can be optionally substituted with one or more of the suitable groups.

As used herein the term "cycloalkyl" alone or in combination with other term(s) means $C_3$-$C_{10}$ saturated cyclic hydrocarbon ring. A cycloalkyl may be a single ring, which typically contains from 3 to 7 carbon ring atoms. Examples of single-ring cycloalkyls include cyclopropyl, cyclobutyl, cyclopentyl, cyclohexyl, cycloheptyl and the like. A cycloalkyl may alternatively be polycyclic or contain more than one ring. Examples of polycyclic cycloalkyls include bridged, fused, and spirocyclic carbocyclyls.

As used herein, the term "cyano" refers to —CN group.

As used herein, the term "hydroxy" or "hydroxyl" refers to —OH group.

As used herein the term "hydroxyalkyl" or "hydroxylalkyl" means alkyl substituted with one or more hydroxyl groups, wherein the alkyl groups are as defined above. Examples of "hydroxyalkyl" include but are not limited to hydroxymethyl, hydroxyethyl, hydroxypropyl, propan-2-ol and the like.

As used herein, the term "halo" or "halogen" alone or in combination with other term(s) means fluorine, chlorine, bromine or iodine.

As used herein, the term "heterocyclyl" includes definitions of "heterocycloalkyl" and "heteroaryl".

As used herein, the term "heterocycloalkyl" refers to a non-aromatic, saturated or partially saturated, monocyclic or polycyclic ring system of 3 to 15 member having at least one heteroatom or heterogroup selected from O, N, S, S(O), $S(O)_2$, NH or C(O) with the remaining ring atoms being independently selected from carbon, oxygen, nitrogen, and sulfur. Examples of "heterocycloalkyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, 2-aza-bicyclo[2.2.2]octanyl, azocinyl, chromanyl, xanthenyl and N-oxides thereof. Attachment of a heterocycloalkyl substituent can occur via either a carbon atom or a heteroatom. A heterocycloalkyl group can be optionally substituted with one or more suitable groups by one or more aforesaid groups. Preferably "heterocycloalkyl" refers to 5- to 6-membered ring selected from azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyland N-oxides thereof. More preferably, "heterocycloalkyl" includes azetidinyl, pyrrolidinyl, morpholinyl and piperidinyl. All heterocycloalkyl are optionally substituted by one or more aforesaid groups.

As used herein, the term "heteroaryl" refers to an aromatic heterocyclic ring system containing 5 to 20 ring atoms, suitably 5 to 10 ring atoms, which may be a single ring (monocyclic) or multiple rings (bicyclic, tricyclic or polycyclic) fused together or linked covalently. Preferably, "heteroaryl" is a 5- to 6-membered ring. The rings may contain from 1 to 4 heteroatoms selected from N, O and S, wherein the N or S atom is optionally oxidized or the N atom is optionally quarternized. Any suitable ring position of the heteroaryl moiety may be covalently linked to the defined chemical structure.

Examples of heteroaryl include, but are not limited to: furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl, pyridazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carboline, indolizinyl, benzoisothiazolyl, benzoxazolyl, pyrrolopyridyl, furopyridinyl, purinyl, benzothiadiazolyl, benzooxadiazolyl, benzotriazolyl, benzotriadiazolyl, carbazolyl, dibenzothienyl, acridinyl and the like. Preferably "heteroaryl" refers to 5- to 6-membered ring selected from furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl, pyrimidinyl, pyrazinyl and pyridazinyl. More preferably, pyrazolyl, pyridyl, oxazolyl and furanyl. All heteroaryls are optionally substituted by one or more aforesaid groups.

As used herein, the term 'compound(s)' comprises the compounds disclosed in the present invention.

As used herein, the term "comprise" or "comprising" is generally used in the sense of include, that is to say permitting the presence of one or more features or components.

As used herein, the term "or" means "and/or" unless stated otherwise.

As used herein, the term "including" as well as other forms, such as "include", "includes" and "included" is not limiting.

The phrase "pharmaceutically acceptable" refers to compounds or compositions that are physiologically tolerable and do not typically produce allergic or similar untoward reaction, including but not limited to gastric upset or dizziness when administered to mammal.

The term "pharmaceutically acceptable salt" refers to a product obtained by reaction of the compound of the present invention with a suitable acid or a base. Pharmaceutically acceptable salts of the compounds of this invention include those derived from suitable inorganic bases such as Li, Na, K, Ca, Mg, Fe, Cu, Al, Zn and Mn salts; Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts, and the like. Certain compounds of the invention (can form pharmaceutically acceptable salts with various organic bases such as lysine, arginine, guanidine, diethanolamine or metformin. Suitable base salts include, but are not limited to, aluminum, calcium, lithium, magnesium, potassium, sodium, or zinc, salts.

As used herein, the term "stereoisomer" is a term used for all isomers of individual compounds of compound of formula (I) that differ only in the orientation of their atoms in space. The term stereoisomer includes mirror image isomers (enantiomers) of compounds of the present invention, mixtures of mirror image isomers (racemates, racemic mixtures) of compounds of the present invention, geometric (cis/trans or E/Z, R/S) isomers of compounds of the present invention and isomers of compounds of the present invention with more than one chiral center that are not mirror images of one another (diastereoisomers).

In certain embodiments, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically labeled compounds of the present inventions can generally be prepared by following procedures well known in the art, such as by substituting an isotopically labeled reagent for a non-isotopically labeled reagent.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. The examples of carriers, stabilizers and adjuvant are mentioned in literature like, Martin, Remington's Pharmaceutical Sciences, 15th Ed., Mack Publ. Co., Easton, PA [1975].

The term "treatment"/"treating" means any treatment of a disease in a mammal, including: (a) Inhibiting the disease, i.e., slowing or arresting the development of clinical symptoms; and/or (b) Relieving the disease, i.e., causing the regression of clinical symptoms and/or (c) Alleviating or abrogating a disease and/or its attendant symptoms.

As used herein, the term "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

As used herein, the term "subject" refers to an animal, preferably a mammal, and most preferably a human.

As used herein, the term, "therapeutically effective amount" refers to an amount of a compound of the present invention or a pharmaceutically acceptable salt or a stereoisomer thereof; or a composition comprising the compound of the present invention or a pharmaceutically acceptable salt or a stereoisomer thereof, effective in producing the desired therapeutic response in a particular patient suffering from AML. Particularly, the term "therapeutically effective amount" includes the amount of the compound of the present invention or a pharmaceutically acceptable salt or a stereoisomer thereof, when administered, that induces a positive modification in the disease or disorder to be treated or is sufficient to prevent development of, or alleviate to some extent, one or more of the symptoms of the disease or disorder being treated in a subject. In respect of the therapeutic amount of the compound, the amount of the compound used for the treatment of a subject is low enough to avoid undue or severe side effects, within the scope of sound medical judgment can also be considered. The therapeutically effective amount of the compound or composition will be varied with the particular condition being treated, the severity of the condition being treated or prevented, the duration of the treatment, the nature of concurrent therapy, the age and physical condition of the end user, the specific compound or composition employed the particular pharmaceutically acceptable carrier utilized.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. In some embodiments, the additional therapeutic compound is administered within about 5 minutes to within about 168 hours prior to or after administration of the compound of formula I, the compound of formula II, or the compound of formula III. Thus, a subject who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

Provided herein is a method of treating or preventing acute myeloid leukemia in a subject, comprising administering a compound of formula (I)

(I)

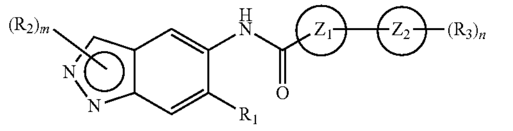

or a pharmaceutically acceptable salt thereof;

wherein

Ring $Z_1$ is an optionally substituted heteroaryl;

Ring $Z_2$ is an optionally substituted heterocycloalkyl, optionally substituted heteroaryl or a direct bond;

$R_1$ is alkyl, cyano, —$NR_aR_b$, or optionally substituted groups selected from cycloalkyl, aryl or heterocyclyl; wherein the substituent, at each occurrence, independently is alkyl, alkoxy, halogen, hydroxyl, hydroxyalkyl, amino, aminoalkyl, nitro, cyano, haloalkyl, haloalkoxy, —OCO—$CH_2$—O-alkyl, —OP(O)(O-alkyl)$_2$ or —$CH_2$—OP(O)(O-alkyl)$_2$;

$R_2$, at each occurrence, independently is an optionally substituted group selected from alkyl or cycloalkyl; wherein the substituent, at each occurrence, is independently halogen, alkoxy, hydroxyl, hydroxyalkyl, haloalkyl or haloalkoxy;

$R_3$, at each occurrence, independently is hydrogen, halogen, alkyl, haloalkyl, haloalkoxy, alkoxy, —$NR_aR_b$, hydroxyl or hydroxyalkyl;

$R_a$ is hydrogen or alkyl;

$R_b$ is hydrogen, alkyl, acyl, hydroxyalkyl, —$SO_2$-alkyl or optionally substituted cycloalkyl;

'm' and 'n' are independently 1 or 2.

In some embodiments, the present methods include a compound of formula (I) or a pharmaceutically acceptable salt thereof; wherein, Ring $Z_1$ is a 5- or 6-membered optionally substituted heteroaryl.

In some embodiments, the present methods include a compound of formula (I) or a pharmaceutically acceptable salt thereof; wherein Ring $Z_1$ is an optionally substituted heteroaryl; wherein the optional substituent is alkyl.

In some embodiments, the present methods include a compound of formula (I) or a pharmaceutically acceptable salt thereof, wherein Ring $Z_1$ is selected from tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl and pyrazolyl.

In some embodiments, the present methods include a compound of formula (I) or a pharmaceutically acceptable salt thereof, wherein Ring $Z_1$ is selected from pyridyl, oxazolyl and furanyl; wherein the pyridyl group is optionally substituted with alkyl; in particular alkyl is methyl.

In some embodiments, the present methods include a compound of formula (I) or a pharmaceutically acceptable salt thereof, wherein Ring $Z_2$ is a 5- or 6-membered heteroaryl selected from tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl or pyrazolyl.

In some embodiments, the present methods include a compound of formula (I) or a pharmaceutically acceptable salt thereof, wherein Ring $Z_2$ is a 5- or 6-membered heterocycloalkyl selected from azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl or 1,4-dioxanyl.

In some embodiments, the present methods include a compound of formula (I) or a pharmaceutically acceptable salt thereof, wherein Ring $Z_2$ is pyridyl, pyrazolyl or pyrrolidinyl.

In some embodiments, the present methods include a compound of formula (I) or a pharmaceutically acceptable salt thereof, wherein Ring $Z_2$ is a direct bond.

In some embodiments, the present methods include a compound of formula (I) that is a compound of formula (TA)

(IA)

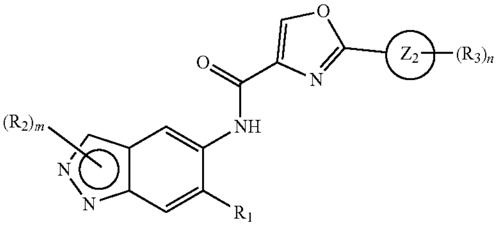

or a pharmaceutically acceptable salt thereof;

wherein, $Z_2$, $R_1$, $R_2$, $R_3$, 'm' and 'n' are same as defined in compound of formula (I).

In some embodiments, the present methods include a compound of formula (I) that is a compound of formula (IB)

(IB)

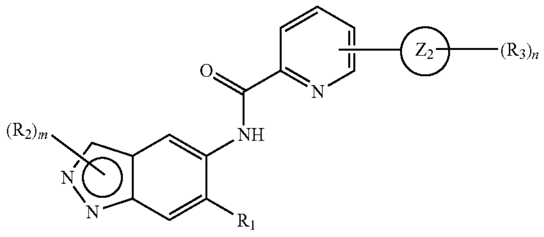

or a pharmaceutically acceptable salt thereof;

wherein, $Z_2$, $R_1$, $R_2$, $R_3$, 'm' and 'n' are same as defined in compound of formula (I).

In some embodiments, the present methods include a compound of formula (I) that is a compound of formula (IC)

(IC)

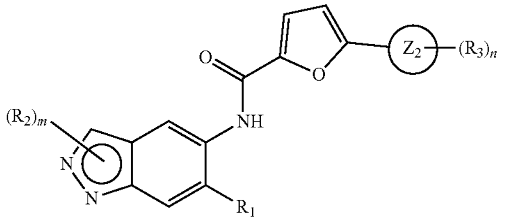

or a pharmaceutically acceptable salt thereof;

wherein, $Z_2$, $R_1$, $R_2$, $R_3$, 'm' and 'n' are same as defined in compound of formula (I).

In some embodiments, the present methods include a compound of formula (I) wherein

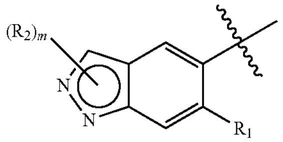

is

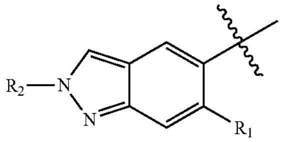

,

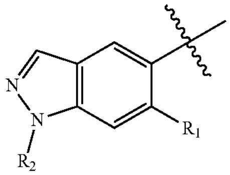

,

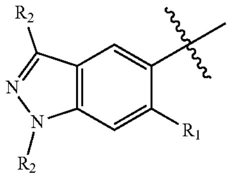

or

-continued

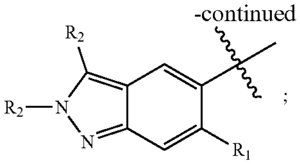

;

wherein $R_1$, $R_2$ and 'm' are same as defined in compound of formula (I).

In some embodiments, the present methods include a compound of formula (I) or a pharmaceutically acceptable salt thereof, wherein Ring $Z_2$ is pyridyl.

In some embodiments, the present methods include a compound of formula (I) or a pharmaceutically acceptable salt thereof, wherein Ring $Z_2$ is pyrazolyl.

In some embodiments, the present methods include a compound of formula (I) or a pharmaceutically acceptable salt thereof, wherein Ring $Z_2$ is pyrrolidinyl.

In some embodiments, the present methods include a compound of formula (I) or a pharmaceutically acceptable salt thereof, wherein $R_1$ is optionally substituted heterocyclyl; wherein the substituent is halogen, hydroxyl, hydroxyalkyl, amino, aminoalkyl, —OCO—$CH_2$—O-alkyl, —OP(O)(O-alkyl)$_2$ or —$CH_2$—OP(O)(O-alkyl)$_2$.

In some embodiments, the present methods include a compound of formula (I) or a pharmaceutically acceptable salt thereof, wherein $R_1$ is optionally substituted azetidinyl, piperidinyl, morpholinyl, pyrrolidinyl or azepanyl; wherein the substituent is amino, halogen, hydroxyl, hydroxyalkyl, aminoalkyl, —OCO—$CH_2$—O-alkyl, —OP(O)(O-alkyl)$_2$ or —$CH_2$—OP(O)(O-alkyl)$_2$.

In some embodiments, the present methods include a compound of formula (I) or a pharmaceutically acceptable salt thereof, wherein $R_1$ is optionally substituted piperidinyl; wherein the substituent is hydroxyl.

In some embodiments, the present methods include a compound of formula (I) or a pharmaceutically acceptable salt thereof, wherein $R_1$ is optionally substituted phenyl; wherein the substituent is halogen.

In some embodiments, the present methods include a compound of formula (I) or a pharmaceutically acceptable salt thereof, wherein $R_1$ is cycloalkyl.

In some embodiments, the present methods include a compound of formula (I) or a pharmaceutically acceptable salt thereof, wherein $R_1$ is cyclopropyl or cyclohexyl.

In some embodiments, the present methods include a compound of formula (I) or a pharmaceutically acceptable salt thereof, wherein $R_1$ is —$NR_aR_b$; $R_a$ is hydrogen; $R_b$ is optionally substituted cycloalkyl; wherein the substituent is hydroxyl.

In some embodiments, the present methods include a compound of formula (I) or a pharmaceutically acceptable salt thereof, wherein $R_1$ is cyano.

In some embodiments, the present methods include a compound of formula (I) or a pharmaceutically acceptable salt thereof, wherein $R_2$ is optionally substituted alkyl; wherein substituent is alkoxy.

In some embodiments, the present methods include a compound of formula (I) or a pharmaceutically acceptable salt thereof, wherein $R_2$ is cycloalkyl.

In some embodiments, the present methods include a compound of formula (I) or a pharmaceutically acceptable salt thereof, wherein $R_3$ is hydrogen, halogen, alkyl, alkoxy, —$NR_aR_b$, hydroxyl or hydroxyalkyl; $R_a$ is hydrogen or alkyl; and $R_b$ is hydrogen, alkyl, acyl, hydroxyalkyl or —$SO_2$-alkyl.

In some embodiments, the present methods include a compound of formula (I) or a pharmaceutically acceptable salt thereof, wherein Ring $Z_1$ is optionally substituted pyridyl; Ring $Z_2$ is pyridyl, pyrazolyl, pyrrolidinyl or direct bond; $R_1$ is an optionally substituted group selected from cyclopropyl, piperidinyl, morpholinyl or pyrrolidinyl; $R_2$ is optionally substituted alkyl or cycloalkyl; $R_3$ is hydrogen, halogen, alkyl, alkoxy, —$NR_aR_b$, hydroxyl or hydroxyalkyl; $R_a$ is hydrogen or alkyl; and $R_b$ is hydrogen or hydroxyalkyl.

In some embodiments, the present methods include a compound of formula (I) or a pharmaceutically acceptable salt thereof, wherein Ring $Z_1$ is oxazolyl; Ring $Z_2$ is pyridyl, pyrazolyl or pyrrolidinyl; $R_1$ is cyano, —$NR_aR_b$, or an optionally substituted group selected from cyclopropyl, cyclohexyl, phenyl, azetidinyl, piperidinyl, morpholinyl or pyrrolidinyl; $R_2$ is optionally substituted alkyl or cycloalkyl; $R_3$ is hydrogen, halogen, alkyl, alkoxy, —$NR_aR_b$, hydroxyl or hydroxyalkyl; $R_a$ is hydrogen or alkyl; and $R_b$ is hydrogen, alkyl, acyl, hydroxyalkyl, —$SO_2$-alkyl or optionally substituted cycloalkyl.

In some embodiments, the present methods include a s compound of formula (I) or a pharmaceutically acceptable salt thereof, wherein $R_3$ is —$NR_aR_b$; $R_a$ is hydrogen or alkyl; and $R_b$ is hydrogen, alkyl, acyl, hydroxyalkyl, —$SO_2$-alkyl or optionally substituted cycloalkyl; wherein the optional substituent is hydroxyl;

In some embodiments, the present methods include a compound of formula (I) or a pharmaceutically acceptable salt thereof, wherein 'n' is 1.

In some embodiments, the present methods include a compound of formula (I) or a pharmaceutically acceptable salt thereof, wherein 'n' is 2.

In some embodiments, the present methods include a compound of formula (I) or a pharmaceutically acceptable salt thereof, wherein 'm' is 1.

In some embodiments, the present methods include a compound of formula (I) or a pharmaceutically acceptable salt thereof, wherein 'm' is 2.

In some embodiments, the present methods include a compound of formula (I) selected from:

N-(2-methyl-6-(piperidin-1-yl)-2H-indazol-5-yl)-6-(1H-pyrazol-4-yl) picolinamide;
N-(2-methyl-6-(piperidin-1-yl)-2H-indazol-5-yl)-2-(2-methylpyridin-4-yl) oxazole-4-carboxamide;
N-(1-methyl-6-(piperidin-1-yl)-1H-indazol-5-yl)-2-(2-methylpyridin-4-yl) oxazole-4-carboxamide;
N-(2-cyclopentyl-6-(piperidin-1-yl)-2H-indazol-5-yl)-2-(2-methylpyridin-4-yl) oxazole-4-carboxamide;
N-(6-cyano-2-cyclopentyl-2H-indazol-5-yl)-2-(2-methylpyridin-4-yl) oxazole-4-carboxamide;
N-(2-cyclopentyl-6-cyclopropyl-2H-indazol-5-yl)-2-(2-methylpyridin-4-yl) oxazole-4-carboxamide;
N-(2-cyclopentyl-6-cyclopropyl-2H-indazol-5-yl)-6-(1H-pyrazol-4-yl) picolinamide;
N-(2-cyclopentyl-6-morpholino-2H-indazol-5-yl)-2-(2-methylpyridin-4-yl) oxazole-4-carboxamide;
6'-amino-N-(2-cyclopentyl-6-morpholino-2H-indazol-5-yl)-[2,3'-bipyridine]-6-carboxamide 2,2,2-trifluoroacetate;
N-(6-(3-fluorophenyl)-2-methyl-2H-indazol-5-yl)-2-(2-methylpyridin-4-yl)oxazole-4-carboxamide;
N-(6-cyclohexyl-2-methyl-2H-indazol-5-yl)-2-(2-methylpyridin-4-yl)oxazole-4-carboxamide hydrochloride;
6'-fluoro-N-(2-methyl-6-(piperidin-1-yl)-2H-indazol-5-yl)-[2,3'-bipyridine]-6-carboxamide hydrochloride;
N-(6-cyclohexyl-2-methyl-2H-indazol-5-yl)-6-(1H-pyrazol-4-yl)picolinamide hydrochloride;
2'-fluoro-N-(2-methyl-6-(piperidin-1-yl)-2H-indazol-5-yl)-[2,3'-bipyridine]-6-carboxamide;
2-(2-chloropyridin-4-yl)-N-(2-methyl-6-(piperidin-1-yl)-2H-indazol-5-yl)oxazole-4-carboxamide hydrochloride;
N-(6-cyclopropyl-2-methyl-2H-indazol-5-yl)-2-(2-methylpyridin-4-yl)oxazole-4-carboxamide hydrochloride;
N-(1-cyclopentyl-6-cyclopropyl-1H-indazol-5-yl)-6-(1-methyl-1H-pyrazol-4-yl)picolinamide;
N-(2-cyclopentyl-6-cyclopropyl-2H-indazol-5-yl)-6-(1-methyl-1H-pyrazol-4-yl)picolinamide;
6-(1-methyl-1H-pyrazol-4-yl)-N-(2-methyl-6-(piperidin-1-yl)-2H-indazol-5-yl)picolinamide;
N-(2-cyclopentyl-6-cyclopropyl-2H-indazol-5-yl)-2-(6-methoxypyridin-3-yl)oxazole-4-carboxamide;
2-(6-methoxypyridin-3-yl)-N-(2-methyl-6-(piperidin-1-yl)-2H-indazol-5-yl)oxazole-4-carboxamide;
N-(2-methyl-6-(piperidin-1-yl)-2H-indazol-5-yl)-2-(3-methylpyridin-4-yl)oxazole-4-carboxamide;
6-bromo-N-(2-methyl-6-(piperidin-1-yl)-2H-indazol-5-yl)picolinamide;
6-chloro-5-methyl-N-(2-methyl-6-(piperidin-1-yl)-2H-indazol-5-yl)picolinamide
N-(2-methyl-6-(piperidin-1-yl)-2H-indazol-5-yl)-2-(6-methylpyridin-3-yl)oxazole-4-carboxamide;
N-(2-cyclopentyl-6-cyclopropyl-2H-indazol-5-yl)-2-(2-methylpyridin-3-yl)oxazole-4-carboxamide;
N-(2-cyclopentyl-6-cyclopropyl-2H-indazol-5-yl)-2-(3-methylpyridin-4-yl)oxazole-4-carboxamide;
N-(2-cyclopentyl-6-cyclopropyl-2H-indazol-5-yl)-2-(6-methylpyridin-3-yl)oxazole-4-carboxamide;

-continued

6'-amino-3-methyl-N-(2-methyl-6-(piperidin-1-yl)-2H-indazol-5-yl)-[2,3'-bipyridine]-6-carboxamide hydrochloride;
5-methyl-6-(1-methyl-1H-pyrazol-4-yl)-N-(2-methyl-6-(piperidin-1-yl)-2H-indazol-5-yl)picolinamide;
N-(1-cyclopropyl-6-(piperidin-1-yl)-1H-indazol-5-yl)-2-(2-methylpyridin-4-yl)oxazole-4-carboxamide hydrochloride;
2-(2-hydroxypyridin-3-yl)-N-(2-methyl-6-(piperidin-1-yl)-2H-indazol-5-yl)oxazole-4-carboxamide;
(S)-6-(3-aminopyrrolidin-1-yl)-N-(2-methyl-6-(piperidin-1-yl)-2H-indazol-5-yl)picolinamide 2,2,2-trifluoroacetate;
(S)-6-(1-(2-hydroxypropyl)-1H-pyrazol-4-yl)-N-(2-methyl-6-(piperidin-1-yl)-2H-indazol-5-yl)picolinamide;
N-(1,6-dicyclopropyl-1H-indazol-5-yl)-2-(6-methoxypyridin-3-yl)oxazole-4-carboxamide;
N-(1,6-dicyclopropyl-1H-indazol-5-yl)-2-(2-methylpyridin-4-yl)oxazole-4-carboxamide hydrochloride;
(S)-N-(6-cyclopropyl-1-methyl-1H-indazol-5-yl)-6-(3-hydroxypyrrolidin-1-yl)picolinamide;
(R)-6-(3-hydroxypyrrolidin-1-yl)-N-(2-methyl-6-(piperidin-1-yl)-2H-indazol-5-yl)picolinamide;
(S)-6-(3-hydroxypyrrolidin-1-yl)-N-(2-methyl-6-(piperidin-1-yl)-2H-indazol-5-yl)picolinamide;
6-(3-hydroxypyrrolidin-1-yl)-N-(2-methyl-6-(piperidin-1-yl)-2H-indazol-5-yl)picolinamide;
(S)-6-(3-aminopyrrolidin-1-yl)-N-(6-cyclopropyl-1-methyl-1H-indazol-5-yl)picolinamide;
(R)-6-(3-aminopyrrolidin-1-yl)-N-(2-methyl-6-(piperidin-1-yl)-2H-indazol-5-yl)picolinamide;
(R)-6-(1-(2-hydroxypropyl)-1H-pyrazol-4-yl)-N-(2-methyl-6-(piperidin-1-yl)-2H-indazol-5-yl)picolinamide;
(S)-2-(3-aminopyrrolidin-1-yl)-N-(2-methyl-6-(piperidin-1-yl)-2H-indazol-5-yl)oxazole-4-carboxamide;
N-(6-cyclopropyl-1-methyl-1H-indazol-5-yl)-2-(2-methylpyridin-4-yl)oxazole-4-carboxamide;
(S)-N-(6-cyclopropyl-1-methyl-1H-indazol-5-yl)-6-(1-(2-hydroxypropyl)-1H-pyrazol-4-yl)picolinamide;
(S)-N-(6-cyclopropyl-2-methyl-2H-indazol-5-yl)-6-(1-(2-hydroxypropyl)-1H-pyrazol-4-yl)picolinamide;
(S)-6-(3-aminopyrrolidin-1-yl)-N-(6-cyclopropyl-2-methyl-2H-indazol-5-yl)picolinamide;
(S)-N-(6-cyclopropyl-2-methyl-2H-indazol-5-yl)-6-(3-hydroxypyrrolidin-1-yl)picolinamide;
(S)-N-(6-cyclopropyl-1-methyl-1H-indazol-5-yl)-2-(3-hydroxypyrrolidin-1-yl)oxazole-4-carboxamide;
(S)-2-(3-aminopyrrolidin-1-yl)-N-(6-cyclopropyl-1-methyl-1H-indazol-5-yl)oxazole-4-carboxamide;
(S)-2-(3-hydroxypyrrolidin-1-yl)-N-(2-methyl-6-(piperidin-1-yl)-2H-indazol-5-yl)oxazole-4-carboxamide;
(S)-N-(6-cyclopropyl-1-methyl-1H-indazol-5-yl)-2-(1-(2-hydroxypropyl)-1H-pyrazol-4-yl)oxazole-4-carboxamide;
(S)-2-(3-aminopyrrolidin-1-yl)-N-(6-cyclopropyl-2-methyl-2H-indazol-5-yl)oxazole-4-carboxamide;
(S)-N-(6-cyclopropyl-2-methyl-2H-indazol-5-yl)-2-(3-hydroxypyrrolidin-1-yl)oxazole-4-carboxamide;
(S)-6-(1-(2-hydroxypropyl)-1H-pyrazol-4-yl)-N-(2-methyl-6-(piperidin-1-yl)-2H-indazol-5-yl)picolinamide;
6-((2-hydroxypropyl)amino)-N-(2-methyl-6-(piperidin-1-yl)-2H-indazol-5-yl)picolinamide;
N-(6-(4-hydroxypiperidin-1-yl)-2-methyl-2H-indazol-5-yl)-2-(2-methylpyridin-4-yl)oxazole-4-carboxamide;
N-(6-(azetidin-1-yl)-1-methyl-1H-indazol-5-yl)-2-(2-methylpyridin-4-yl)oxazole-4-carboxamide;
N-(6-(azetidin-1-yl)-2-methyl-2H-indazol-5-yl)-2-(2-methylpyridin-4-yl)oxazole-4-carboxamide;
N-(6-(3-hydroxyazetidin-1-yl)-2-methyl-2H-indazol-5-yl)-2-(2-methylpyridin-4-yl)oxazole-4-carboxamide;
N-(1-methyl-6-(pyrrolidin-1-yl)-1H-indazol-5-yl)-2-(2-methylpyridin-4-yl)oxazole-4-carboxamide;
N-(2-methyl-6-(pyrrolidin-1-yl)-2H-indazol-5-yl)-2-(2-methylpyridin-4-yl)oxazole-4-carboxamide;
(S)-N-(6-(3-hydroxypyrrolidin-1-yl)-2-methyl-2H-indazol-5-yl)-2-(2-methylpyridin-4-yl)oxazole-4-carboxamide;
(R)-N-(6-(3-hydroxypyrrolidin-1-yl)-2-methyl-2H-indazol-5-yl)-2-(2-methylpyridin-4-yl)oxazole-4-carboxamide;
N-(2-methyl-6-(piperidin-1-yl)-2H-indazol-5-yl)-5-(2-methylpyridin-4-yl)furan-2-carboxamide;
N-(6-(4-hydroxypiperidin-1-yl)-2-methyl-2H-indazol-5-yl)-5-(2-methylpyridin-4-yl)furan-2-carboxamide;

-continued

N-(6-(3-hydroxypiperidin-1-yl)-2-methyl-2H-indazol-5-yl)-2-(2-methylpyridin-4-yl)oxazole-4-carboxamide;
(R)-N-(6-(3-hydroxypiperidin-1-yl)-2-methyl-2H-indazol-5-yl)-5-(2-methylpyridin-4-yl)furan-2-carboxamide;
N-(6-(3-hydroxypiperidin-1-yl)-2-methyl-2H-indazol-5-yl)-5-(2-methylpyridin-4-yl)furan-2-carboxamide;
N-(6-(azepan-1-yl)-2-methyl-2H-indazol-5-yl)-2-(2-methylpyridin-4-yl)oxazole-4-carboxamide;
N-(6-(azepan-1-yl)-1-methyl-1H-indazol-5-yl)-2-(2-methylpyridin-4-yl)oxazole-4-carboxamide;
N-(2,3-dimethyl-6-(piperidin-1-yl)-2H-indazol-5-yl)-2-(2-methylpyridin-4-yl)oxazole-4-carboxamide;
N-(1,3-dimethyl-6-(piperidin-1-yl)-1H-indazol-5-yl)-2-(2-methylpyridin-4-yl)oxazole-4-carboxamide;
N-(6-(4-hydroxypiperidin-1-yl)-1-(2-methoxyethyl)-1H-indazol-5-yl)-2-(2-methylpyridin-4-yl)oxazole-4-carboxamide;
N-(6-(4-hydroxypiperidin-1-yl)-2-(2-methoxyethyl)-2H-indazol-5-yl)-2-(2-methylpyridin-4-yl)oxazole-4-carboxamide;
N-(6-(4-hydroxypiperidin-1-yl)-1-methyl-1H-indazol-5-yl)-2-(2-methylpyridin-4-yl)oxazole-4-carboxamide;
N-(6-(4-fluoropiperidin-1-yl)-1-methyl-1H-indazol-5-yl)-2-(2-methylpyridin-4-yl)oxazole-4-carboxamide;
N-(6-(3-fluoropiperidin-1-yl)-2-methyl-2H-indazol-5-yl)-2-(2-methylpyridin-4-yl)oxazole-4-carboxamide;
N-(6-(4-(hydroxymethyl)piperidin-1-yl)-2-methyl-2H-indazol-5-yl)-2-(2-methylpyridin-4-yl)oxazole-4-carboxamide;
N-(6-(4-hydroxypiperidin-1-yl)-1,3-dimethyl-1H-indazol-5-yl)-2-(2-methylpyridin-4-yl)oxazole-4-carboxamide;
N-(6-(3-(hydroxymethyl)piperidin-1-yl)-2-methyl-2H-indazol-5-yl)-2-(2-methylpyridin-4-yl)oxazole-4-carboxamide;
N-(6-(4-hydroxypiperidin-1-yl)-2,3-dimethyl-2H-indazol-5-yl)-2-(2-methylpyridin-4-yl)oxazole-4-carboxamide;
2-(2-acetamidopyridin-4-yl)-N-(2-methyl-6-(piperidin-1-yl)-2H-indazol-5-yl)oxazole-4-carboxamide;
2-(2-acetamidopyridin-4-yl)-N-(6-(3-fluoropiperidin-1-yl)-2-methyl-2H-indazol-5-yl)oxazole-4-carboxamide;
2-(2-aminopyridin-4-yl)-N-(2-methyl-6-(piperidin-1-yl)-2H-indazol-5-yl)oxazole-4-carboxamide hydrochloride;
N-(6-(4-fluoropiperidin-1-yl)-1,3-dimethyl-1H-indazol-5-yl)-2-(2-methylpyridin-4-yl)oxazole-4-carboxamide;
N-(6-(((1R,4R)-4-hydroxycyclohexyl)amino)-2-methyl-2H-indazol-5-yl)-2-(2-methylpyridin-4-yl)oxazole-4-carboxamide;
N-(6-(4-(hydroxymethyl)piperidin-1-yl)-1-methyl-1H-indazol-5-yl)-2-(2-methylpyridin-4-yl)oxazole-4-carboxamide;
2-(2-aminopyridin-4-yl)-N-(6-(4-fluoropiperidin-1-yl)-2-methyl-2H-indazol-5-yl)oxazole-4-carboxamide hydrochloride;
N-(6-(4-fluoropiperidin-1-yl)-2-methyl-2H-indazol-5-yl)-2-(2-methylpyridin-4-yl)oxazole-4-carboxamide hydrochloride;
(S)-N-(6-(4-(hydroxymethyl)piperidin-1-yl)-2-methyl-2H-indazol-5-yl)-6-(1-(2-hydroxypropyl)-1H-pyrazol-4-yl)picolinamide;
2-(2-aminopyridin-4-yl)-N-(6-(4-hydroxypiperidin-1-yl)-2-methyl-2H-indazol-5-yl)oxazole-4-carboxamide hydrochloride;
N-(6-(4-(hydroxymethyl)piperidin-1-yl)-1-(2-methoxyethyl)-1H-indazol-5-yl)-2-(2-methylpyridin-4-yl)oxazole-4-carboxamide;
(S)-N-(6-(4-(hydroxymethyl)piperidin-1-yl)-1-methyl-1H-indazol-5-yl)-6-(1-(2-hydroxypropyl)-1H-pyrazol-4-yl)picolinamide;
N-(6-(4-(hydroxymethyl)piperidin-1-yl)-2-(2-methoxyethyl)-2H-indazol-5-yl)-2-(2-methylpyridin-4-yl)oxazole-4-carboxamide;
N-(6-(4-(hydroxymethyl)piperidin-1-yl)-2-methyl-2H-indazol-5-yl)-2-(2-methoxypyridin-4-yl)oxazole-4-carboxamide;
2-(2-acetamidopyridin-4-yl)-N-(6-(4-(hydroxymethyl)piperidin-1-yl)-2-methyl-2H-indazol-5-yl)oxazole-4-carboxamide;
2-(2-aminopyridin-4-yl)-N-(6-(4-(hydroxymethyl)piperidin-1-yl)-1-methyl-1H-indazol-5-yl)oxazole-4-carboxamide hydrochloride;
2-(2-aminopyridin-4-yl)-N-(6-(4-(hydroxymethyl)piperidin-1-yl)-2-methyl-2H-indazol-5-yl)oxazole-4-carboxamide hydrochloride;
N-(6-(4-hydroxypiperidin-1-yl)-1-methyl-1H-indazol-5-yl)-2-(2-methoxypyridin-4-yl)oxazole-4-carboxamide;
2-(2-aminopyridin-4-yl)-N-(6-(3-hydroxypiperidin-1-yl)-2-methyl-2H-indazol-5-yl)oxazole-4-carboxamide hydrochloride;
2-(2-methoxypyridin-4-yl)-N-(2-methyl-6-(piperidin-1-yl)-2H-indazol-5-yl)oxazole-4-carboxamide;
2-(2-aminopyridin-4-yl)-N-(6-(3-fluoropiperidin-1-yl)-2-methyl-2H-indazol-5-yl)oxazole-4-carboxamide hydrochloride;
(R)-2-(2-aminopyridin-4-yl)-N-(6-(3-hydroxypyrrolidin-1-yl)-2-methyl-2H-indazol-5-yl)oxazole-4-carboxamide hydrochloride;
1-(1,3-dimethyl-5-(2-(2-methylpyridin-4-yl)oxazole-4-carboxamido)-1H-indazol-6-yl)piperidin-4-yl 2-methoxyacetate;

-continued

N-(6-(4-hydroxypiperidin-1-yl)-2-methyl-2H-indazol-5-yl)-2-(2-methoxypyridin-4-yl)oxazole-4-carboxamide hydrochloride;
N-(6-(4-aminopiperidin-1-yl)-1-(2-methoxyethyl)-1H-indazol-5-yl)-2-(2-methylpyridin-4-yl)oxazole-4-carboxamide hydrochloride;
N-(6-(4-aminopiperidin-1-yl)-2-methyl-2H-indazol-5-yl)-2-(2-methylpyridin-4-yl)oxazole-4-carboxamide hydrochloride;
N-(6-(4-(hydroxymethyl)piperidin-1-yl)-1-(2-methoxyethyl)-3-methyl-1H-indazol-5-yl)-2-(2-methylpyridin-4-yl)oxazole-4-carboxamide;
N-(6-(4-(hydroxymethyl)piperidin-1-yl)-1,3-dimethyl-1H-indazol-5-yl)-2-(2-methylpyridin-4-yl)oxazole-4-carboxamide;
2-(2-aminopyridin-4-yl)-N-(6-(4-(hydroxymethyl)piperidin-1-yl)-1,3-dimethyl-1H-indazol-5-yl)oxazole-4-carboxamide;
N-(6-(4-hydroxypiperidin-1-yl)-1-methyl-1H-indazol-5-yl)-2-(2-hydroxypyridin-4-yl)oxazole-4-carboxamide;
2-(2,6-dimethylpyridin-4-yl)-N-(6-(4-hydroxypiperidin-1-yl)-1-methyl-1H-indazol-5-yl)oxazole-4-carboxamide;
(S)-N-(6-(3-hydroxypyrrolidin-1-yl)-1-methyl-1H-indazol-5-yl)-2-(2-methylpyridin-4-yl)oxazole-4-carboxamide;
N-(6-(4-hydroxypiperidin-1-yl)-1-(2-methoxyethyl)-3-methyl-1H-indazol-5-yl)-2-(2-methylpyridin-4-yl)oxazole-4-carboxamide;
N-(1-(2-hydroxyethyl)-6-(4-hydroxypiperidin-1-yl)-1H-indazol-5-yl)-2-(2-methylpyridin-4-yl)oxazole-4-carboxamide;
N-(6-(4-aminopiperidin-1-yl)-2-(2-methoxyethyl)-2H-indazol-5-yl)-2-(2-methylpyridin-4-yl)oxazole-4-carboxamide hydrochloride;
2-(2,6-dimethylpyridin-4-yl)-N-(2-methyl-6-(piperidin-1-yl)-2H-indazol-5-yl)oxazole-4-carboxamide hydrochloride;
2-(2-(dimethylamino)pyridin-4-yl)-N-(2-methyl-6-(piperidin-1-yl)-2H-indazol-5-yl)oxazole-4-carboxamide;
N-(6-(4-hydroxypiperidin-1-yl)-1-methyl-1H-indazol-5-yl)-2-(2-(methylamino)pyridin-4-yl)oxazole-4-carboxamide;
N-(2-methyl-6-(piperidin-1-yl)-2H-indazol-5-yl)-2-(2-(methylamino)pyridin-4-yl)oxazole-4-carboxamide;
N-(6-(4-hydroxypiperidin-1-yl)-2-methyl-2H-indazol-5-yl)-2-(2-(methylsulfonamido) pyridin-4-yl) oxazole-4-carboxamide;
2-(2-(dimethylamino) pyridin-4-yl)-N-(6-(4-hydroxypiperidin-1-yl)-1-methyl-1H-indazol-5-yl) oxazole-4-carboxamide;
N-(6-(4-(aminomethyl)piperidin-1-yl)-1-(2-methoxyethyl)-1H-indazol-5-yl)-2-(2-methylpyridin-4-yl)oxazole-4-carboxamide;
2-(2,6-dimethylpyridin-4-yl)-N-(6-(4-hydroxypiperidin-1-yl)-2-methyl-2H-indazol-5-yl) oxazole-4-carboxamide;
2-(2,6-dimethylpyridin-4-yl)-N-(6-(4-fluoropiperidin-1-yl)-2-methyl-2H-indazol-5-yl) oxazole-4-carboxamide;
Diethyl (1-(1-methyl-5-(2-(2-methylpyridin-4-yl)oxazole-4-carboxamido)-1H-indazol-6-yl)piperidin-4-yl) phosphate; and
Diethyl ((1-(2-methyl-5-(2-(2-methylpyridin-4-yl) oxazole-4-carboxamido)-2H-indazol-6-yl) piperidin-4-yl) methyl) phosphate;

or a pharmaceutically acceptable salt or a stereoisomer thereof.

Provided herein is a method of treating or preventing acute myeloid leukemia in a subject, comprising administering a compound of formula (II):

(II)

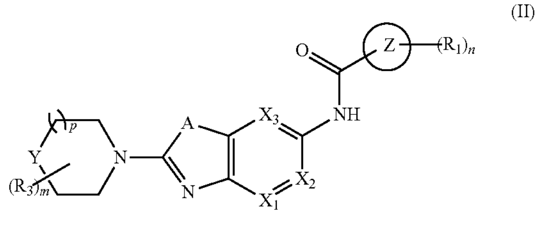

or a pharmaceutically acceptable salt thereof;

wherein, $X_1$ and $X_3$ independently are CH or N; $X_2$ is $CR_2$ or N; provided one and not more than one of $X_1$, $X_2$ or $X_3$ is N;

A is O or S;

Y is —$CH_2$— or O;

Ring Z is aryl or heterocyclyl;

$R_1$, at each occurrence, is independently halo or optionally substituted heterocyclyl; wherein the substituent is alkyl, alkoxy, aminoalkyl, halo, hydroxyl, hydroxyalkyl or —$NR_aR_b$;

$R_2$ is hydrogen, optionally substituted cycloalkyl, optionally substituted aryl, optionally substituted heterocyclyl or —$NR_aR_b$; wherein the substituent is alkyl, amino, halo or hydroxyl;

$R_3$, at each occurrence, is alkyl or hydroxyl;

$R_a$ and $R_b$ are independently hydrogen, alkyl, acyl or heterocyclyl;

'm' and 'n' are independently 0, 1 or 2;

'p' is 0 or 1.

In some embodiments, the present methods include a compound of formula (II) or a pharmaceutically acceptable salt thereof, wherein the group

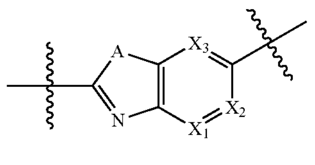

is

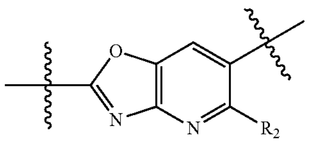

,

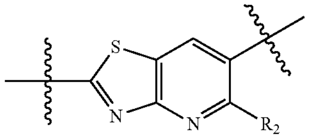

,

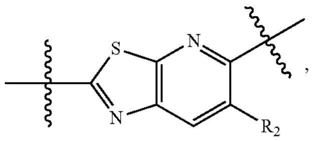

,

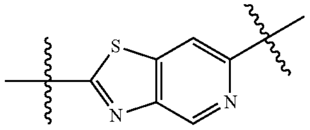

or

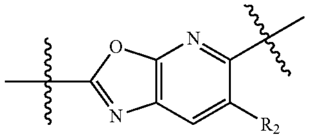

;

wherein $R_2$ are as defined in compound of formula (II).

In some embodiments, the present methods include a compound of formula (II) or a pharmaceutically acceptable salt thereof, wherein the Ring Z is aryl or 5- or 6-membered heterocyclyl.

In some embodiments, the present methods include a compound of formula (II) or a pharmaceutically acceptable salt thereof, wherein the Ring Z is phenyl, furanyl, thienyl, pyrrolyl, pyrazolyl, imidazolyl, oxazolyl, isoxazolyl, thiazolyl, isothiazolyl, 1H-tetrazolyl, oxadiazolyl, triazolyl, pyridyl, pyrimidinyl, pyrazinyl, pyridazinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl or dihydropyranyl; each of which is optionally substituted with alkyl, alkoxy, halo, hydroxyl, hydroxyalkyl or —$NR_aR_b$; $R_a$ and $R_b$ are independently are hydrogen, alkyl or acyl.

In some embodiments, the present methods include a compound of formula (II) or a pharmaceutically acceptable salt thereof, wherein the Ring Z is phenyl, oxazolyl, furanyl, thienyl or pyridyl; each of which is optionally substituted with one or more $R_1$.

In some embodiments, the present methods include a compound of formula (II) or a pharmaceutically acceptable salt thereof, wherein

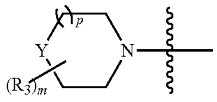

is

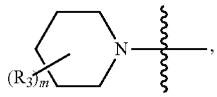

,

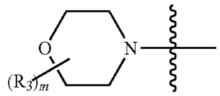

or

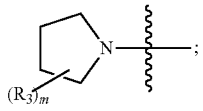

;

wherein $R_3$ and 'm' are defined in compound of formula (II).

In some embodiments, the present methods include a compound of formula (II) that is a compound of formula (IIA):

(IIA)

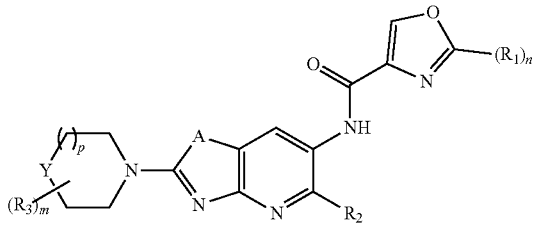

or a pharmaceutically acceptable salt thereof;

wherein, A, Y, $R_1$, $R_2$, $R_3$, 'm', 'p' and 'n' are same as defined in compound of formula (II).

In some embodiments, the present methods include a compound of formula (II) that is a compound of formula (IIB):

(IIB)

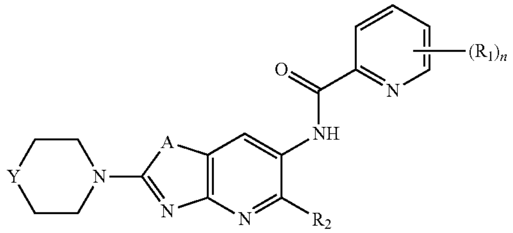

or a pharmaceutically acceptable salt thereof;

wherein, A, Y, $R_1$, $R_2$ and 'n' are same as defined in compound of formula (II).

In some embodiments, the present methods include a compound of formula (II) that is a compound of formula (IIC):

(IIC)

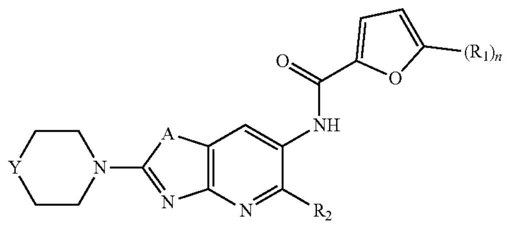

or a pharmaceutically acceptable salt thereof;

wherein, A, Y, $R_1$, $R_2$, $R_3$ and 'n' are same as defined compounds of formula (I).

In some embodiments, the present methods include a compound of formula (II), (IIA), (IIB), or (IIC) or a pharmaceutically acceptable salt thereof, wherein Y is O or $CH_2$.

In some embodiments, the present methods include a compound of formula (II) or a pharmaceutically acceptable salt thereof, wherein $R_1$ is optionally substituted heterocyclyl; wherein the substituent is alkyl, alkoxy, aminoalkyl, halo, hydroxyl, hydroxyalkyl or —$NR_aR_b$; $R_a$ and $R_b$ are independently hydrogen, alkyl or acyl.

In some embodiments, the present methods include a compound of formula (II) or a pharmaceutically acceptable salt thereof, wherein $R_1$ is pyridyl, pyrazolyl, pyrrolidinyl or piperidinyl; each of which is optionally substituted with alkyl, alkoxy, halo, hydroxyl, hydroxyalkyl or —$NR_aR_b$; $R_a$ and $R_b$ are independently hydrogen or acyl.

In some embodiments, the present methods include a compound of formula (II) or a pharmaceutically acceptable salt thereof, wherein $R_2$ is hydrogen.

In some embodiments, the present methods include a compound of formula (II) or a pharmaceutically acceptable salt thereof, wherein $R_2$ is optionally substituted cycloalkyl.

In some embodiments, the present methods include a compound of formula (II) or a pharmaceutically acceptable salt thereof, wherein $R_2$ is cyclopropyl.

In some embodiments, the present methods include a compound of formula (II) or a pharmaceutically acceptable salt thereof, wherein $R_2$ is optionally substituted heterocyclyl; wherein the substituent is alkyl, amino, halo or hydroxyl.

In some embodiments, the present methods include a compound of formula (II) or a pharmaceutically acceptable salt thereof, wherein $R_2$ is piperidinyl, pyrrolidinyl, morpholinyl, piperazinyl, azetidinyl, pyrazolyl, furanyl, pyridyl, azepanyl or azabicyclo[3.2.1]octanyl; wherein the substituent is alkyl, amino, halo or hydroxyl.

In some embodiments, the present methods include a compound of formula (II) or a pharmaceutically acceptable salt thereof, wherein $R_2$ is optionally substituted aryl; wherein the substituent is halo.

In some embodiments, the present methods include a compound of formula (II) or a pharmaceutically acceptable salt thereof, wherein $R_2$ is optionally substituted phenyl; wherein the substituent is fluoro.

In some embodiments, the present methods include a compound of formula (II) or a pharmaceutically acceptable salt thereof, wherein $R_2$ is —$NR_aR_b$; wherein $R_a$ and $R_b$ are independently hydrogen or heterocyclyl.

In some embodiments, the present methods include a compound of formula (II) or a pharmaceutically acceptable salt thereof, wherein $R_2$ is —$NR_aR_b$; wherein $R_a$ and $R_b$ are independently hydrogen or pyrrolidinyl.

In some embodiments, the present methods include a compound of formula (IIA) or a pharmaceutically acceptable salt thereof, wherein A is O or S; Y is —$CH_2$— or O; $R_1$ is halo, pyridyl, pyrazolyl, pyrrolidinyl each of which is optionally substituted with alkyl, alkoxy, halo, hydroxyl, hydroxyalkyl or —$NR_aR_b$; $R_2$ is hydrogen, optionally substituted cycloalkyl, optionally substituted aryl, optionally substituted heterocyclyl or —$NR_aR_b$; wherein the substituent is alkyl, amino, halo or hydroxyl; $R_a$ and $R_b$ are independently hydrogen or alkyl.

In some embodiments, the present methods include a compound of formula (IIB) or a pharmaceutically acceptable salt thereof, wherein A is O or S; Y is —$CH_2$— or O; $R_1$ is pyridyl, pyrazolyl, pyrrolidinyl; each of which is optionally substituted with alkyl, hydroxyl, hydroxyalkyl or —$NR_aR_b$; $R_a$ and $R_b$ are independently hydrogen; $R_2$ is hydrogen, optionally substituted cycloalkyl, optionally substituted aryl, optionally substituted heterocyclyl or —$NR_aR_b$; wherein the substituent is alkyl, amino, halo or hydroxyl; $R_a$ and $R_b$ are independently hydrogen, alkyl, acyl or heterocyclyl.

In some embodiments, the present methods include a compound of formula (IIA), (IIB) or (IIC), or a pharmaceutically acceptable salt thereof, wherein 'n' is 0, 1 or 2.

In some embodiments, the present methods include a compound of formula (IIA) or (IIB), or a pharmaceutically acceptable salt thereof, wherein 'p' is 0 or 1.

In some embodiments, the present methods include a compound of formula (IIA) or (IIB), or a pharmaceutically acceptable salt thereof, wherein 'm' is 0 or 2.

In some embodiments, the present methods include a compound of formula (II) selected from:

6'-amino-N-(2-morpholinooxazolo[4,5-b]pyridin-6-yl)-[2,3'-bipyridine]-6-carboxamide;
6'-amino-N-(5-cyclopropyl-2-morpholinooxazolo[4,5-b]pyridin-6-yl)-[2,3'-bipyridine]-6-carboxamide hydrochloride;
N-(5-cyclopropyl-2-morpholinooxazolo[4,5-b]pyridin-6-yl)-2-(2-methylpyridin-4-yl)oxazole-4-carboxamide hydrochloride;
N-(2,5-di(piperidin-1-yl)oxazolo[4,5-b]pyridin-6-yl)-6-(1H-pyrazol-4-yl)picolinamide hydrochloride;
N-(2,5-di(piperidin-1-yl)oxazolo[4,5-b]pyridin-6-yl)-2-(2-methylpyridin-4-yl)oxazole-4-carboxamide;
N-(2-morpholino-5-(piperidin-1-yl)oxazolo[4,5-b]pyridin-6-yl)-6-(1H-pyrazol-4-yl)picolinamide;
2-(2-methylpyridin-4-yl)-N-(2-morpholino-5-(piperidin-1-yl)oxazolo[4,5-b]pyridin-6-yl)oxazole-4-carboxamide;
6-chloro-N-(2-morpholino-5-(piperidin-1-yl)oxazolo[4,5-b]pyridin-6-yl)picolinamide;
N-(2,5-di(piperidin-1-yl)oxazolo[4,5-b]pyridin-6-yl)-6-(1-methyl-1H-pyrazol-4-yl)picolinamide;
2-(2-chloropyridin-4-yl)-N-(2,5-di(piperidin-1-yl)oxazolo[4,5-b]pyridin-6-yl)oxazole-4-carboxamide;

-continued (S)-2-(2-methylpyridin-4-yl)-N-(2-morpholino-5-(pyrrolidin-3-ylamino)oxazolo[4,5-b]pyridin-6-yl)oxazole-4-carboxamide;
6'-amino-N-(2-morpholinooxazolo[5,4-b]pyridin-5-yl)-[2,3'-bipyridine]-6-carboxamide;
6'-amino-N-(2-morpholinothiazolo[4,5-c]pyridin-6-yl)-[2,3'-bipyridine]-6-carboxamide;
6'-amino-N-(2-morpholinothiazolo[5,4-b]pyridin-5-yl)-[2,3'-bipyridine]-6-carboxamide;
2-(2-methylpyridin-4-yl)-N-(2-morpholinothiazolo[4,5-b]pyridin-6-yl)oxazole-4-carboxamide;
6'-amino-N-(2-morpholinothiazolo[4,5-b]pyridin-6-yl)-[2,3'-bipyridine]-6-carboxamide;
N-(2-morpholinothiazolo[4,5-b]pyridin-6-yl)-6-(1H-pyrazol-4-yl)picolinamide;
3-(4-(aminomethyl)piperidin-1-yl)-5-fluoro-N-(2-morpholinothiazolo[4,5-b]pyridin-6-yl)benzamide;
2-(4-(aminomethyl)piperidin-1-yl)-5-fluoro-N-(2-morpholinothiazolo[4,5-b]pyridin-6-yl)benzamide;
2-(2-methylpyridin-4-yl)-N-(2-morpholino-5-(piperidin-1-yl)thiazolo[4,5-b]pyridin-6-yl)oxazole-4-carboxamide;
N-(2-morpholino-5-(piperidin-1-yl)thiazolo[4,5-b]pyridin-6-yl)-6-(1H-pyrazol-4-yl)picolinamide;
N-(2,5-di(piperidin-1-yl)thiazolo[4,5-b]pyridin-6-yl)-6-(1H-pyrazol-4-yl)picolinamide;
N-(2,5-di(piperidin-1-yl)thiazolo[4,5-b]pyridin-6-yl)-2-(2-methylpyridin-4-yl)oxazole-4-carboxamide;
N-(2,5-dimorpholinooxazolo[4,5-b]pyridin-6-yl)-2-(2-methylpyridin-4-yl)oxazole-4-carboxamide;
N-(5-(4-methylpiperazin-1-yl)-2-morpholinooxazolo[4,5-b]pyridin-6-yl)-2-(2-methylpyridin-4-yl)oxazole-4-carboxamide;
N-(2,5-di(piperidin-1-yl)oxazolo[4,5-b]pyridin-6-yl)-2-(6-methoxypyridin-3-yl)oxazole-4-carboxamide;
N-(2,5-di(piperidin-1-yl)oxazolo[4,5-b]pyridin-6-yl)-2-(2-methylpyridin-3-yl)oxazole-4-carboxamide;
N-(2,5-di(piperidin-1-yl)oxazolo[4,5-b]pyridin-6-yl)-2-(2-hydroxypyridin-3-yl)oxazole-4-carboxamide;
2-(2-hydroxypyridin-3-yl)-N-(2-morpholino-5-(piperidin-1-yl)oxazolo[4,5-b]pyridin-6-yl)oxazole-4-carboxamide;
N-(2,5-di(piperidin-1-yl)oxazolo[4,5-b]pyridin-6-yl)-2-(6-hydroxypyridin-3-yl)oxazole-4-carboxamide;
2-(2-methoxypyridin-4-yl)-N-(2-morpholino-5-(piperidin-1-yl)oxazolo[4,5-b]pyridin-6-yl)oxazole-4-carboxamide;
2-(2-methylpyridin-3-yl)-N-(2-morpholino-5-(piperidin-1-yl)oxazolo[4,5-b]pyridin-6-yl)oxazole-4-carboxamide;
2-(3-methylpyridin-4-yl)-N-(2-morpholino-5-(piperidin-1-yl)oxazolo[4,5-b]pyridin-6-yl)oxazole-4-carboxamide;
N-(2,5-di(piperidin-1-yl)oxazolo[4,5-b]pyridin-6-yl)-2-(3-methylpyridin-4-yl)oxazole-4-carboxamide;
2-(6-methylpyridin-3-yl)-N-(2-morpholino-5-(piperidin-1-yl)oxazolo[4,5-b]pyridin-6-yl)oxazole-4-carboxamide;
6-(1-methyl-1H-pyrazol-4-yl)-N-(2-morpholino-5-(piperidin-1-yl)oxazolo[4,5-b]pyridin-6-yl)picolinamide;
N-(2,5-di(piperidin-1-yl)oxazolo[4,5-b]pyridin-6-yl)-2-(6-methylpyridin-3-yl)oxazole-4-carboxamide;
(S)-N-(5-(3-aminopyrrolidin-1-yl)-2-morpholinooxazolo[4,5-b]pyridin-6-yl)-2-(2-methylpyridin-4-yl)oxazole-4-carboxamide;
(S)-N-(5-(3-hydroxypyrrolidin-1-yl)-2-morpholinooxazolo[4,5-b]pyridin-6-yl)-2-(2-methylpyridin-4-yl)oxazole-4-carboxamide;
(R)-N-(5-(3-aminopyrrolidin-1-yl)-2-morpholinooxazolo[4,5-b]pyridin-6-yl)-2-(2-methylpyridin-4-yl)oxazole-4-carboxamide;
(R)-N-(5-(3-hydroxypyrrolidin-1-yl)-2-morpholinooxazolo[4,5-b]pyridin-6-yl)-2-(2-methylpyridin-4-yl)oxazole-4-carboxamide;
(S)-2-(3-aminopyrrolidin-1-yl)-N-(2-morpholino-5-(piperidin-1-yl)oxazolo[4,5-b]pyridin-6-yl)oxazole-4-carboxamide;
(S)-6-(3-hydroxypyrrolidin-1-yl)-N-(2-morpholino-5-(piperidin-1-yl)oxazolo[4,5-b]pyridin-6-yl)picolinamide;
(S)-6-(3-aminopyrrolidin-1-yl)-N-(2-morpholino-5-(piperidin-1-yl)oxazolo[4,5-b]pyridin-6-yl)picolinamide;
(S)-2-(3-hydroxypyrrolidin-1-yl)-N-(2-morpholino-5-(piperidin-1-yl)oxazolo[4,5-b]pyridin-6-yl)oxazole-4-carboxamide;
(S)-N-(5-cyclopropyl-2-morpholinooxazolo[4,5-b]pyridin-6-yl)-2-(3-hydroxypyrrolidin-1-yl)oxazole-4-carboxamide;
(S)-2-(3-aminopyrrolidin-1-yl)-N-(5-cyclopropyl-2-morpholinooxazolo[4,5-b]pyridin-6-yl)oxazole-4-carboxamide;
2-(2-methylpyridin-4-yl)-N-(5-(piperidin-1-yl)-2-(pyrrolidin-1-yl)oxazolo[4,5-b]pyridin-6-yl)oxazole-4-carboxamide hydrochloride;
N-(2-(2,6-dimethylmorpholino)-5-(piperidin-1-yl)oxazolo[4,5-b]pyridin-6-yl)-2-(2-methylpyridin-4-yl)oxazole-4-carboxamide hydrochloride;
N-(2,5-di(piperidin-1-yl)thiazolo[4,5-b]pyridin-6-yl)-6-(1-methyl-1H-pyrazol-4-yl)picolinamide hydrochloride;

-continued 6-(1-methyl-1H-pyrazol-4-yl)-N-(2-morpholino-5-(piperidin-1-yl)thiazolo[4,5-b]pyridin-6-yl)picolinamide;
N-(2,5-di(piperidin-1-yl)thiazolo[4,5-b]pyridin-6-yl)-2-(2-methylpyridin-3-yl)oxazole-4-carboxamide hydrochloride;
N-(2-((2S,6R)-2,6-dimethylmorpholino)-5-(piperidin-1-yl)thiazolo[4,5-b]pyridin-6-yl)-2-(2-methylpyridin-4-yl)oxazole-4-carboxamide;
2-(2-methylpyridin-3-yl)-N-(2-morpholino-5-(piperidin-1-yl)thiazolo[4,5-b]pyridin-6-yl)oxazole-4-carboxamide;
2-(2-hydroxypyridin-3-yl)-N-(2-morpholino-5-(piperidin-1-yl)thiazolo[4,5-b]pyridin-6-yl)oxazole-4-carboxamide;
N-(2,5-di(piperidin-1-yl)thiazolo[4,5-b]pyridin-6-yl)-2-(2-methoxypyridin-4-yl)oxazole-4-carboxamide;
2-(6-methoxypyridin-3-yl)-N-(2-morpholino-5-(piperidin-1-yl)thiazolo[4,5-b]pyridin-6-yl)oxazole-4-carboxamide;
2-(2-methoxypyridin-4-yl)-N-(2-morpholino-5-(piperidin-1-yl)thiazolo[4,5-b]pyridin-6-yl)oxazole-4-carboxamide;
(S)-N-(5-(3-fluoropiperidin-1-yl)-2-morpholinothiazolo[4,5-b]pyridin-6-yl)-2-(2-methylpyridin-4-yl)oxazole-4-carboxamide;
2-(6-methylpyridin-3-yl)-N-(2-morpholino-5-(piperidin-1-yl)thiazolo[4,5-b]pyridin-6-yl)oxazole-4-carboxamide;
2-(3-methylpyridin-4-yl)-N-(2-morpholino-5-(piperidin-1-yl)thiazolo[4,5-b]pyridin-6-yl)oxazole-4-carboxamide;
(S)-6-(3-aminopyrrolidin-1-yl)-N-(2-morpholino-5-(piperidin-1-yl)thiazolo[4,5-b]pyridin-6-yl)picolinamide;
(S)-6-(3-hydroxypyrrolidin-1-yl)-N-(2-morpholino-5-(piperidin-1-yl)thiazolo[4,5-b]pyridin-6-yl)picolinamide;
(S)-6-(3-aminopyrrolidin-1-yl)-N-(2,5-di(piperidin-1-yl)thiazolo[4,5-b]pyridin-6-yl)picolinamide;
(S)-N-(2,5-di(piperidin-1-yl)thiazolo[4,5-b]pyridin-6-yl)-6-(3-hydroxypyrrolidin-1-yl)picolinamide;
(S)-2-(3-aminopyrrolidin-1-yl)-N-(2-morpholino-5-(piperidin-1-yl)thiazolo[4,5-b]pyridin-6-yl)oxazole-4-carboxamide;
(S)-N-(5-(3-aminopyrrolidin-1-yl)-2-morpholinothiazolo[4,5-b]pyridin-6-yl)-2-(2-methylpyridin-4-yl)oxazole-4-carboxamide;
(S)-2-(3-aminopyrrolidin-1-yl)-N-(5-cyclopropyl-2-morpholinothiazolo[4,5-b]pyridin-6-yl)oxazole-4-carboxamide;
N-(5-cyclopropyl-2-morpholinothiazolo[4,5-b]pyridin-6-yl)-2-(2-methylpyridin-4-yl)oxazole-4-carboxamide;
(S)-2-(3-hydroxypyrrolidin-1-yl)-N-(2-morpholino-5-(piperidin-1-yl)thiazolo[4,5-b]pyridin-6-yl)oxazole-4-carboxamide;
(S)-N-(5-(3-hydroxypyrrolidin-1-yl)-2-morpholinothiazolo[4,5-b]pyridin-6-yl)-2-(2-methylpyridin-4-yl)oxazole-4-carboxamide;
(S)-N-(5-cyclopropyl-2-morpholinothiazolo[4,5-b]pyridin-6-yl)-6-(3-hydroxypyrrolidin-1-yl)picolinamide;
(S)-N-(5-cyclopropyl-2-morpholinothiazolo[4,5-b]pyridin-6-yl)-2-(3-hydroxypyrrolidin-1-yl)oxazole-4-carboxamide;
(S)-N-(5-cyclopropyl-2-morpholinothiazolo[4,5-b]pyridin-6-yl)-6-(1-(2-hydroxypropyl)-1H-pyrazol-4-yl)picolinamide;
(S)-N-(5-cyclopropyl-2-morpholinothiazolo[4,5-b]pyridin-6-yl)-2-(1-(2-hydroxypropyl)-1H-pyrazol-4-yl)oxazole-4-carboxamide;
N-(5-(3-hydroxypyrrolidin-1-yl)-2-morpholinothiazolo[4,5-b]pyridin-6-yl)-2-(6-methoxypyridin-3-yl)oxazole-4-carboxamide;
(S)-N-(5-(3-hydroxypyrrolidin-1-yl)-2-morpholinothiazolo[4,5-b]pyridin-6-yl)-2-(6-methoxypyridin-3-yl)oxazole-4-carboxamide;
(R)-N-(5-(3-hydroxypyrrolidin-1-yl)-2-morpholinothiazolo[4,5-b]pyridin-6-yl)-2-(6-methoxypyridin-3-yl)oxazole-4-carboxamide;
(S)-N-(5-(azetidin-1-yl)-2-morpholinothiazolo[4,5-b]pyridin-6-yl)-6-(3-hydroxypyrrolidin-1-yl)picolinamide;
N-(5-(3-hydroxyazetidin-1-yl)-2-morpholinothiazolo[4,5-b]pyridin-6-yl)-2-(2-methylpyridin-4-yl)oxazole-4-carboxamide;
(S)-N-(5-(3-hydroxypyrrolidin-1-yl)-2-morpholinothiazolo[4,5-b]pyridin-6-yl)-5-(2-methylpyridin-4-yl)thiophene-2-carboxamide;
(S)-N-(5-(3-hydroxypyrrolidin-1-yl)-2-morpholinothiazolo[4,5-b]pyridin-6-yl)-5-(2-methylpyridin-4-yl)furan-2-carboxamide;
(S)-N-(5-(3-hydroxypiperidin-1-yl)-2-morpholinothiazolo[4,5-b]pyridin-6-yl)-2-(2-methylpyridin-4-yl)oxazole-4-carboxamide;
N-(5-(4-hydroxypiperidin-1-yl)-2-morpholinothiazolo[4,5-b]pyridin-6-yl)-2-(2-methylpyridin-4-yl)oxazole-4-carboxamide
(R)-N-(5-(3-hydroxypyrrolidin-1-yl)-2-morpholinothiazolo[4,5-b]pyridin-6-yl)-2-(2-methylpyridin-4-yl)oxazole-4-carboxamide;
N-(5-(4-hydroxypiperidin-1-yl)-2-morpholinothiazolo[4,5-b]pyridin-6-yl)-5-(2-methylpyridin-4-yl)furan-2-carboxamide;
N-(5-(azetidin-1-yl)-2-(piperidin-1-yl)thiazolo[4,5-b]pyridin-6-yl)-2-(2-methylpyridin-4-yl)oxazole-4-carboxamide;
2-(2-methylpyridin-4-yl)-N-(2-(piperidin-1-yl)-5-(pyrrolidin-1-yl)thiazolo[4,5-b]pyridin-6-yl)oxazole-4-carboxamide;
2-(2-methylpyridin-4-yl)-N-(2-morpholino-5-(pyrrolidin-1-yl)thiazolo[4,5-b]pyridin-6-yl)oxazole-4-carboxamide;

-continued 5-(2-methylpyridin-4-yl)-N-(2-morpholino-5-(piperidin-1-yl)thiazolo[4,5-b]pyridin-6-yl)furan-2-carboxamide;
N-(5-(azepan-1-yl)-2-morpholinothiazolo[4,5-b]pyridin-6-yl)-2-(2-methylpyridin-4-yl)oxazole-4-carboxamide;
2-(2-aminopyridin-4-yl)-N-(2-morpholino-5-(piperidin-1-yl)thiazolo[4,5-b]pyridin-6-yl)oxazole-4-carboxamide hydrochloride;
N-(5-(azetidin-1-yl)-2-morpholinothiazolo[4,5-b]pyridin-6-yl)-2-(2-methylpyridin-4-yl)oxazole-4-carboxamide;
(R)-N-(5-(3-hydroxypiperidin-1-yl)-2-morpholinothiazolo[4,5-b]pyridin-6-yl)-2-(2-methylpyridin-4-yl)oxazole-4-carboxamide;
(R)-N-(5-(3-hydroxypiperidin-1-yl)-2-morpholinothiazolo[4,5-b]pyridin-6-yl)-5-(2-methylpyridin-4-yl)furan-2-carboxamide;
(S)-6-(1-(2-hydroxypropyl)-1H-pyrazol-4-yl)-N-(2-morpholino-5-(piperidin-1-yl)thiazolo[4,5-b]pyridin-6-yl)picolinamide
N-(5-(4-fluoropiperidin-1-yl)-2-morpholinothiazolo[4,5-b]pyridin-6-yl)-5-(2-methylpyridin-4-yl)furan-2-carboxamide
N-(5-(4-fluoropiperidin-1-yl)-2-morpholinothiazolo[4,5-b]pyridin-6-yl)-2-(2-methylpyridin-4-yl)oxazole-4-carboxamide hydrochloride
N-(5-(1-methyl-1H-pyrazol-4-yl)-2-morpholinothiazolo[4,5-b]pyridin-6-yl)-2-(2-methylpyridin-4-yl)oxazole-4-carboxamide;
N-(5-(3-fluorophenyl)-2-morpholinothiazolo[4,5-b]pyridin-6-yl)-2-(2-methylpyridin-4-yl)oxazole-4-carboxamide;
N-(5-(4-hydroxypiperidin-1-yl)-2-morpholinothiazolo[4,5-b]pyridin-6-yl)-5-(2-methylpyridin-4-yl)furan-2-carboxamide;
N-(5-(3-fluoropiperidin-1-yl)-2-morpholinothiazolo[4,5-b]pyridin-6-yl)-5-(2-methylpyridin-4-yl)furan-2-carboxamide;
(S)-N-(5-(3-hydroxypyrrolidin-1-yl)-2-morpholinooxazolo[4,5-b]pyridin-6-yl)-2-(6-methoxypyridin-3-yl)oxazole-4-carboxamide;
N-(5-(3-hydroxypyrrolidin-1-yl)-2-morpholinooxazolo[4,5-b]pyridin-6-yl)-2-(2-methylpyridin-4-yl)oxazole-4-carboxamide;
(R)-N-(5-(3-hydroxypyrrolidin-1-yl)-2-morpholinooxazolo[4,5-b]pyridin-6-yl)-2-(6-methoxypyridin-3-yl)oxazole-4-carboxamide;
N-(5-(3-hydroxypyrrolidin-1-yl)-2-morpholinooxazolo[4,5-b]pyridin-6-yl)-2-(6-methoxypyridin-3-yl)oxazole-4-carboxamide;
(S)-N-(5-(3-hydroxypyrrolidin-1-yl)-2-morpholinooxazolo[4,5-b]pyridin-6-yl)-5-(2-methylpyridin-4-yl)furan-2-carboxamide;
(S)-N-(5-(3-hydroxypyrrolidin-1-yl)-2-morpholinooxazolo[4,5-b]pyridin-6-yl)-5-(2-methylpyridin-4-yl)thiophene-2-carboxamide;
N-(5-(azetidin-1-yl)-2-(piperidin-1-yl)oxazolo[4,5-b]pyridin-6-yl)-2-(2-methylpyridin-4-yl)oxazole-4-carboxamide;
2-(2-methylpyridin-4-yl)-N-(2-(piperidin-1-yl)-5-(pyrrolidin-1-yl)oxazolo[4,5-b]pyridin-6-yl)oxazole-4-carboxamide;
5-(2-methylpyridin-4-yl)-N-(2-morpholino-5-(piperidin-1-yl)oxazolo[4,5-b]pyridin-6-yl)furan-2-carboxamide;
N-(5-(azetidin-1-yl)-2-morpholinooxazolo[4,5-b]pyridin-6-yl)-2-(2-methylpyridin-4-yl)oxazole-4-carboxamide;
2-(2-methylpyridin-4-yl)-N-(2-morpholino-5-(pyrrolidin-1-yl)oxazolo[4,5-b]pyridin-6-yl)oxazole-4-carboxamide;
N-(5-(4-hydroxypiperidin-1-yl)-2-morpholinooxazolo[4,5-b]pyridin-6-yl)-5-(2-methylpyridin-4-yl)furan-2-carboxamide;
(R)-N-(5-(3-hydroxypiperidin-1-yl)-2-morpholinooxazolo[4,5-b]pyridin-6-yl)-5-(2-methylpyridin-4-yl)furan-2-carboxamide;
N-(5-(furan-3-yl)-2-morpholinooxazolo[4,5-b]pyridin-6-yl)-2-(2-methylpyridin-4-yl)oxazole-4-carboxamide;
N-(5-(3-fluoropiperidin-1-yl)-2-morpholinooxazolo[4,5-b]pyridin-6-yl)-2-(2-methylpyridin-4-yl)oxazole-4-carboxamide;
N-(5-(4-hydroxypiperidin-1-yl)-2-morpholinooxazolo[4,5-b]pyridin-6-yl)-2-(2-methylpyridin-4-yl)oxazole-4-carboxamide;
N-(5-(4-fluoropiperidin-1-yl)-2-morpholinooxazolo[4,5-b]pyridin-6-yl)-2-(2-methylpyridin-4-yl)oxazole-4-carboxamide;
(S)-N-(5-(3-aminopiperidin-1-yl)-2-morpholinothiazolo[4,5-b]pyridin-6-yl)-2-(2-methylpyridin-4-yl)oxazole-4-carboxamide;
2-(2-methylpyridin-4-yl)-N-(2-morpholino-5-(1H-pyrazol-4-yl)thiazolo[4,5-b]pyridin-6-yl)oxazole-4-carboxamide;
N-(5-(6-fluoropyridin-3-yl)-2-morpholinothiazolo[4,5-b]pyridin-6-yl)-2-(2-methylpyridin-4-yl)oxazole-4-carboxamide;
N-(5-(3-hydroxy-8-azabicyclo[3.2.1]octan-8-yl)-2-morpholinothiazolo[4,5-b]pyridin-6-yl)-2-(2-methylpyridin-4-yl)oxazole-4-carboxamide;
N-(2-(3-hydroxypiperidin-1-yl)-5-(piperidin-1-yl)thiazolo[4,5-b]pyridin-6-yl)-2-(2-methylpyridin-4-yl)oxazole-4-carboxamide;
2-(2-acetamidopyridin-4-yl)-N-(5-(4-hydroxypiperidin-1-yl)-2-morpholinothiazolo[4,5-b]pyridin-6-yl)oxazole-4-carboxamide;
N-(2-(3-hydroxypiperidin-1-yl)-5-(4-hydroxypiperidin-1-yl)thiazolo[4,5-b]pyridin-6-yl)-2-(2-methylpyridin-4-yl)oxazole-4-carboxamide;
2-(2-acetamidopyridin-4-yl)-N-(5-(3-hydroxypiperidin-1-yl)-2-morpholinothiazolo[4,5-b]pyridin-6-yl)oxazole-4-carboxamide;
2-(2-aminopyridin-4-yl)-N-(5-(3-hydroxypiperidin-1-yl)-2-morpholinothiazolo[4,5-b]pyridin-6-yl)oxazole-4-carboxamide hydrochloride;

-continued

| |
|---|
| 5-(2-aminopyridin-4-yl)-N-(5-(4-hydroxypiperidin-1-yl)-2-morpholinothiazolo[4,5-b]pyridin-6-yl)furan-3-carboxamide hydrochloride; |
| 2-(2-aminopyridin-4-yl)-N-(5-(4-hydroxypiperidin-1-yl)-2-morpholinothiazolo[4,5-b]pyridin-6-yl)oxazole-4-carboxamide hydrochloride; |
| 2-(2-aminopyridin-4-yl)-N-(5-(4-fluoropiperidin-1-yl)-2-morpholinothiazolo[4,5-b]pyridin-6-yl)oxazole-4-carboxamide hydrochloride; |
| N-(5-(2-fluoropyridin-4-yl)-2-morpholinothiazolo[4,5-b]pyridin-6-yl)-2-(2-methylpyridin-4-yl)oxazole-4-carboxamide; |
| N-(5-(4-fluoropiperidin-1-yl)-2-(3-hydroxypiperidin-1-yl)thiazolo[4,5-b]pyridin-6-yl)-2-(2-methylpyridin-4-yl)oxazole-4-carboxamide; |
| N-(5-(4-aminopiperidin-1-yl)-2-(3-hydroxypiperidin-1-yl)thiazolo[4,5-b]pyridin-6-yl)-2-(2-methylpyridin-4-yl)oxazole-4-carboxamide hydrochloride; and |
| N-(5-(2-hydroxypyridin-4-yl)-2-morpholinothiazolo[4,5-b]pyridin-6-yl)-2-(2-methylpyridin-4-yl)oxazole-4-carboxamide hydrochloride; |

or a pharmaceutically acceptable salt or a stereoisomer thereof.

Provided herein is a method of treating or preventing acute myeloid leukemia in a subject, comprising administering a compound of formula (III):

(III)

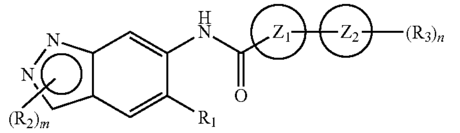

or a pharmaceutically acceptable salt thereof;

wherein, $Z_1$ represents optionally substituted cycloalkyl, optionally substituted aryl, optionally substituted heterocyclyl or is absent;

$Z_2$ represents optionally substituted cycloalkyl, optionally substituted aryl or optionally substituted heterocyclyl;

$R_1$ is hydrogen, optionally substituted alkyl, amino, halo, cyano, optionally substituted cycloalkyl, optionally substituted aryl, optionally substituted heterocyclyl, optionally substituted arylalkyl or optionally substituted heterocyclylalkyl;

$R_2$ at each occurrence is amino, optionally substituted alkyl, optionally substituted cycloalkyl, optionally substituted aryl, optionally substituted heterocyclyl, optionally substituted arylalkyl or optionally substituted heterocyclylalkyl;

$R_3$ at each occurrence is hydroxy, halo, optionally substituted alkyl, optionally substituted alkoxy, optionally substituted cycloalkyl or $-NR_aR_b$;

$R_a$ and $R_b$, independently for each occurrence, are hydrogen, optionally substituted alkyl, optionally substituted acyl, optionally substituted cycloalkyl, optionally substituted aryl, optionally substituted heterocyclyl, optionally substituted arylalkyl or optionally substituted heterocyclylalkyl;

m, at each occurrence, is 0, 1 or 2; and n, at each occurrence, is 0, 1, or 2.

In some embodiments, the present methods include a compound of formula (III) or a pharmaceutically acceptable salt thereof, wherein $Z_1$ is an optionally substituted heterocyclyl.

In some embodiments, the present methods include a compound of formula (III) or a pharmaceutically acceptable salt thereof, wherein $Z_1$ represents cycloalkyl, aryl, or heterocyclyl, optionally substituted by one or more substituents selected, independently for each occurrence, from hydroxy, halo, alkyl, cycloalkyl, or $NR_aR_b$.

In some embodiments, the present methods include a compound of formula (III) or a pharmaceutically acceptable salt thereof, wherein $Z_1$ is an optionally substituted heteroaryl; wherein the optional substituent is alkyl or cycloalkyl.

In some embodiments, the present methods include a compound of formula (III) or a pharmaceutically acceptable salt thereof, wherein $Z_1$ is tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl, pyrazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carboline, indolizinyl, benzoisothiazolyl, benzoxazolyl, pyrrolopyridyl, furopyridinyl, purinyl, benzothiadiazolyl, benzooxadiazolyl, benzotriazolyl, benzotriadiazolyl, carbazolyl, dibenzothienyl, acridinyl and pyrazolopyrimidyl; each of which is optionally substituted.

In some embodiments, the present methods include a compound of formula (III) or a pharmaceutically acceptable salt thereof, wherein $Z_1$ is tetrazolyl, thienyl, triazolyl, pyrrolyl, pyridyl, pyranyl, pyrazinyl, pyridazinyl, pyrimidyl, imidazolyl, oxadiazolyl, thiadiazolyl, thiazolyl, isothiazolyl, oxazolyl, furanyl or pyrazolyl.

In some embodiments, the present methods include a compound of formula (III) or a pharmaceutically acceptable salt thereof, wherein $Z_1$ is pyridyl or oxazolyl; wherein the oxazolyl group is optionally substituted with alkyl; in particular alkyl is methyl.

In some embodiments, the present methods include a compound of formula (III) or a pharmaceutically acceptable thereof, wherein $Z_1$ is absent.

In some embodiments, the present methods include a compound of formula (III) or a pharmaceutically acceptable salt thereof, wherein $Z_2$ is cycloalkyl, aryl or heterocyclyl.

In some embodiments, the present methods include a compound of formula (III) or a pharmaceutically acceptable salt thereof, wherein $Z_2$ represents cycloalkyl, aryl, or heterocyclyl, optionally substituted by one or more substituents selected from hydroxy, halo, alkyl, alkoxyl, cycloalkyl, $-NR_aR_b$, or cycloalkoxy.

In some embodiments, the present methods include a compound of formula (III) or a pharmaceutically acceptable salt thereof, wherein $Z_2$ is heterocyclyl.

In some embodiments, the present methods include a compound of formula (III) or a pharmaceutically acceptable salt thereof, wherein $Z_2$ is azetidinyl, oxetanyl, furanyl, piperidinyl, morpholinyl, piperazinyl, thiomorpholinyl, 1,4-dioxanyl, tetrahydropyranyl, tetrahydrofuranyl, tetrahydropyridyl, tetrazolyl, thienyl, triazolyl, pyrrolyl, pyridyl, pyranyl, pyrazinyl, pyridazinyl, pyrimidyl, imidazolidinyl, imidazolyl, thiadiazolyl, thiazolyl, thiazolidinyl, isothiazolyl, oxadiazolyl, oxazolyl, pyrazolyl, pyrrolidinyl, oxazolidinyl, pyrazolidinyl, benzisoxazolyl, benzothiazolyl, benzofuranyl, benzothienyl, benzotriazinyl, indolyl, isoindolyl, indazolyl, quinolinyl, isoquinolinyl pyrrolopyridyl or pyrazolopyrimidyl.

In some embodiments, the present methods include a compound of formula (III) or a pharmaceutically acceptable salt thereof, wherein $Z_2$ is pyridyl, piperazinyl, pyrimidyl, pyrrolidinyl, 1,2,3,4-tetrahydropyridyl, piperidinyl, pyrazolopyrimidyl or pyrrolopyridyl.

In certain embodiments, the compound of formula (III) is compound of formula (IIIA)

(IIIA)

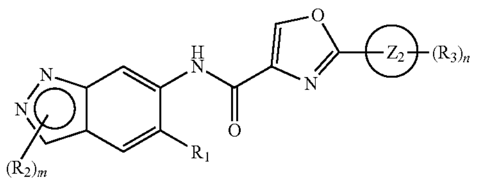

or a pharmaceutically acceptable salt thereof;

wherein, $Z_2$, $R_1$, $R_2$, $R_3$, 'm', and 'n' are as defined in compound of formula (III).

In certain embodiments, the compound of formula (III) is compound of formula (IIIB)

(IIIB)

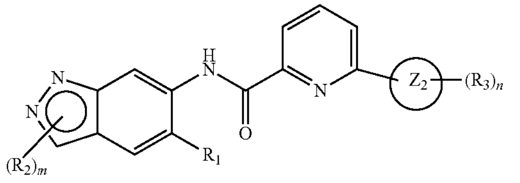

or a pharmaceutically acceptable salt thereof;

wherein, $Z_2$, $R_1$, $R_2$, $R_3$, 'm', and 'n' are as defined in compound of formula (III).

In some embodiments, the present methods include a compound of formula (III) or a pharmaceutically acceptable salt thereof, wherein the group

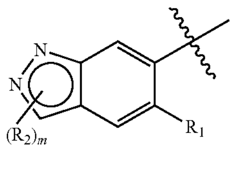

is

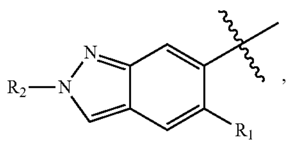

,

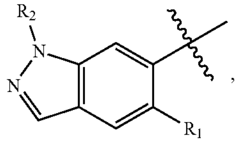

,

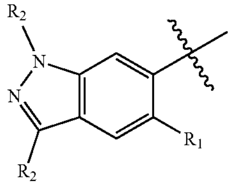

or

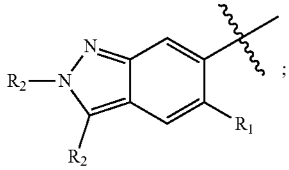

;

wherein $R_1$, $R_2$ and 'm' are same as defined in compound of formula (III).

In some embodiments, the present methods include a compound of formula (III) or a pharmaceutically acceptable salt thereof, wherein $Z_2$ is pyridyl.

In some embodiments, the present methods include a compound of formula (III) or a pharmaceutically acceptable salt thereof, wherein $Z_2$ is pyrrolidinyl.

In some embodiments, the present methods include a compound of formula (III) or a pharmaceutically acceptable salt thereof, wherein $Z_2$ is piperidinyl, piperazinyl, tetrahydropyridyl, pyrimidyl or pyrazolopyridyl.

In some embodiments, the present methods include a compound of formula (III) or a pharmaceutically acceptable salt thereof, wherein $R_1$ is hydrogen, optionally substituted alkyl, amino, halo, cyano, optionally substituted cycloalkyl, optionally substituted aryl, optionally substituted heterocyclyl, optionally substituted arylalkyl or optionally substituted heterocyclylalkyl.

In some embodiments, the present methods include a compound of formula (III) or a pharmaceutically acceptable salt, wherein $R_1$ is alkyl, cycloalkyl, aryl, heterocyclyl, arylalkyl, optionally substituted with one or more substituents selected, independently for each occurrence, from hydroxy, halo, alkyl, or hydroxyalkyl.

In some embodiments, the present methods include a compound of formula (III) or a pharmaceutically acceptable salt, wherein $R_1$ is heterocyclyl; optionally substituted with halogen, hydroxyl or hydroxyalkyl.

In some embodiments, the present methods include a compound of formula (III) or a pharmaceutically acceptable salt, wherein $R_1$ is optionally substituted azetidinyl, piperidinyl, morpholinyl, pyrrolidinyl or azepanyl.

In some embodiments, the present methods include a compound of formula (III) or a pharmaceutically acceptable salt, wherein $R_1$ is piperidinyl, optionally substituted with hydroxyl.

In some embodiments, the present methods include a compound of formula (III) or a pharmaceutically acceptable salt, wherein $R_1$ is pyrrolidinyl, optionally substituted with hydroxyl.

In some embodiments, the present methods include a compound of formula (III) or a pharmaceutically acceptable salt, wherein $R_2$, at each occurrence, is amino, optionally substituted alkyl, optionally substituted cycloalkyl, optionally substituted aryl, optionally substituted heterocyclyl, optionally substituted arylalkyl or optionally substituted heterocyclylalkyl.

In some embodiments, the present methods include a compound of formula (III) or a pharmaceutically acceptable salt, wherein $R_2$ is alkyl, cycloalkyl, aryl, heterocyclyl, arylalkyl, or heterocyclylalkyl, optionally substituted with one or more substituents selected, independently for each occurrence, from alkyl, cycloalkyl, or heterocyclyl.

In some embodiments, the present methods include a compound of formula (III) or a pharmaceutically acceptable salt thereof, wherein $R_2$ is optionally substituted alkyl, preferably, methyl.

In some embodiments, the present methods include a compound of formula (III) or a pharmaceutically acceptable salt thereof, wherein $R_2$ is optionally substituted cycloalkyl, preferably, cyclopropyl.

In some embodiments, the present methods include a compound of formula (III) or a pharmaceutically acceptable salt thereof, wherein $R_3$, at each occurrence, is hydroxy, halo, optionally substituted alkyl, optionally substituted alkoxy, optionally substituted cycloalkyl or —$NR_aR_b$, wherein $R_a$ is hydrogen or optionally substituted alkyl; and $R_b$ is hydrogen, optionally substituted alkyl, optionally substituted acyl, hydroxyalkyl or —$SO_2$-alkyl.

In some embodiments, the present methods include a compound of formula (III) or a pharmaceutically acceptable salt thereof, wherein $Z_1$ is optionally substituted pyridyl; $Z_2$ is pyrrolidinyl; $R_1$ is an optionally substituted groups selected from piperidinyl or pyrrolidinyl; $R_2$ is optionally substituted alkyl; $R_3$ is halogen, alkyl, —$NR_aR_b$, hydroxyl or hydroxyalkyl; $R_a$ is hydrogen or alkyl; and $R_b$ is hydrogen or hydroxyalkyl.

In some embodiments, the present methods include a compound of formula (III) or a pharmaceutically acceptable salt thereof, wherein $Z_1$ is oxazolyl; $Z_2$ is pyridyl, pyrimidyl or pyrrolidinyl, piperidinyl, tetrahydropyridyl, piperazinyl, pyrrolopyridyl; $R_1$ is an optionally substituted group selected from piperidinyl or pyrrolidinyl; $R_2$ is optionally substituted alkyl or cyclopropyl; $R_3$ is halogen, alkyl, alkoxy, —$NR_aR_b$, hydroxyl, hydroxyalkyl optionally substituted cyclopropyl; $R_a$ is hydrogen or alkyl; and $R_b$ is hydrogen, alkyl, acyl, hydroxyalkyl, —$SO_2$-alkyl or optionally substituted cycloalkyl.

In some embodiments, the present methods include a compound of formula (III) or a pharmaceutically acceptable salt thereof, wherein 'm' is 0.

In some embodiments, the present methods include a compound of formula (III) or a pharmaceutically acceptable salt thereof, wherein 'm' is 1.

In some embodiments, the present methods include a compound of formula (III) or a pharmaceutically acceptable salt thereof, wherein 'm' is 2.

In some embodiments, the present methods include a compound of formula (III) or a pharmaceutically acceptable salt thereof, wherein 'n' is 0.

In some embodiments, the present methods include a compound of formula (III) or a pharmaceutically acceptable salt thereof, wherein 'n' is 1.

In some embodiments, the present methods include a compound of formula (III) or a pharmaceutically acceptable salt thereof, wherein 'n' is 2.

In some embodiments, the present methods include a compound of formula (III) selected from:

N-(1-methyl-5-(piperidin-1-yl)-1H-indazol-6-yl)-2-(2-methylpyridin-4-yl)oxazole-4-carboxamide hydrochloride;
N-(2-methyl-5-(piperidin-1-yl)-2H-indazol-6-yl)-2-(2-methylpyridin-4-yl)oxazole-4-carboxamide hydrochloride;
(S)-6-(3-hydroxypyrrolidin-1-yl)-N-(2-methyl-5-(piperidin-1-yl)-2H-indazol-6-yl)picolinamide;
(S)-2-(3-aminopyrrolidin-1-yl)-N-(1-methyl-5-(piperidin-1-yl)-1H-indazol-6-yl)oxazole-4-carboxamide;
(S)-2-(3-aminopyrrolidin-1-yl)-N-(2-methyl-5-(piperidin-1-yl)-2H-indazol-6-yl)oxazole-4-carboxamide;
(S)-2-(3-hydroxypyrrolidin-1-yl)-N-(2-methyl-5-(piperidin-1-yl)-2H-indazol-6-yl)oxazole-4-carboxamide;
(S)-6-(3-aminopyrrolidin-1-yl)-N-(2-methyl-5-(piperidin-1-yl)-2H-indazol-6-yl)picolinamide
(S)-6-(3-aminopyrrolidin-1-yl)-N-(1-methyl-5-(piperidin-1-yl)-1H-indazol-6-yl)picolinamide;
(S)-6-(3-hydroxypyrrolidin-1-yl)-N-(1-methyl-5-(piperidin-1-yl)-1H-indazol-6-yl)picolinamide;
(S)-2-(3-hydroxypyrrolidin-1-yl)-N-(1-methyl-5-(piperidin-1-yl)-1H-indazol-6-yl)oxazole-4-carboxamide;
(S)-N-(5-(3-hydroxypyrrolidin-1-yl)-1-methyl-1H-indazol-6-yl)-2-(2-methylpyridin-4-yl)oxazole-4-carboxamide;
N-(5-(3-hydroxypiperidin-1-yl)-1-methyl-1H-indazol-6-yl)-2-(2-methylpyridin-4-yl)oxazole-4-carboxamide
N-(5-(3-hydroxypiperidin-1-yl)-2-methyl-2H-indazol-6-yl)-2-(2-methylpyridin-4-yl)oxazole-4-carboxamide;
N-(5-(3-fluoropiperidin-1-yl)-2-methyl-2H-indazol-6-yl)-2-(2-methylpyridin-4-yl)oxazole-4-carboxamide;
(S)-2-(2-acetamidopyridin-4-yl)-N-(5-(3-hydroxypyrrolidin-1-yl)-1-methyl-1H-indazol-6-yl)oxazole-4-carboxamide;
N-(5-(3-fluoropiperidin-1-yl)-1-methyl-1H-indazol-6-yl)-2-(2-methylpyridin-4-yl)oxazole-4-carboxamide;
N-(5-(4-hydroxypiperidin-1-yl)-1-methyl-1H-indazol-6-yl)-2-(2-methylpyridin-4-yl)oxazole-4-carboxamide;
(S)-2-(2-aminopyridin-4-yl)-N-(5-(3-hydroxypyrrolidin-1-yl)-1-methyl-1H-indazol-6-yl)oxazole-4-carboxamide;
N-(5-(4-fluoropiperidin-1-yl)-1-methyl-1H-indazol-6-yl)-2-(2-methylpyridin-4-yl)oxazole-4-carboxamide;
N-(5-(4-(hydroxymethyl)piperidin-1-yl)-1-methyl-1H-indazol-6-yl)-2-(2-methylpyridin-4-yl)oxazole-4-carboxamide;
(S)-2-(2,6-dimethylpyridin-4-yl)-N-(5-(3-hydroxypyrrolidin-1-yl)-1-methyl-1H-indazol-6-yl)oxazole-4-carboxamide;
(R)-N-(5-(3-hydroxypyrrolidin-1-yl)-1-methyl-1H-indazol-6-yl)-2-(2-methylpyridin-4-yl)oxazole-4-carboxamide;
(S)-2-(2-aminopyridin-3-yl)-N-(5-(3-hydroxypyrrolidin-1-yl)-1-methyl-1H-indazol-6-yl)oxazole-4-carboxamide Hydrochloride;
6-((S)-3-hydroxypyrrolidin-1-yl)-N-(5-((R)-3-hydroxypyrrolidin-1-yl)-1-methyl-1H-indazol-6-yl)picolinamide;
(S)-N-(5-(3-hydroxypyrrolidin-1-yl)-1-methyl-1H-indazol-6-yl)pyrazolo[1,5-a]pyrimidine-3-carboxamide;
6-((S)-3-hydroxypyrrolidin-1-yl)-N-(5-((S)-3-hydroxypyrrolidin-1-yl)-1-methyl-1H-indazol-6-yl) picolinamide;
(S)-N-(5-(3-hydroxypyrrolidin-1-yl)-1-methyl-1H-indazol-6-yl)-2-(1H-pyrrolo[2,3-b]pyridin-4-yl)oxazole-4-carboxamide;
(S)-N-(5-(3-hydroxypyrrolidin-1-yl)-1H-indazol-6-yl)-2-(2-methylpyridin-4-yl)oxazole-4-carboxamide;
(S)-2-(2-amino-3-fluoropyridin-4-yl)-N-(5-(3-hydroxypyrrolidin-1-yl)-1-methyl-1H-indazol-6-yl)oxazole-4-carboxamide;
(R)-2-(2-aminopyridin-3-yl)-N-(5-(3-hydroxypyrrolidin-1-yl)-1-methyl-1H-indazol-6-yl)oxazole-4-carboxamide hydrochloride;
(S)-N-(5-(3-hydroxypyrrolidin-1-yl)-1-methyl-1H-indazol-6-yl)-2-(4-methylpiperazin-1-yl)oxazole-4-carboxamide;
(S)-N-(5-(3-hydroxypyrrolidin-1-yl)-1-methyl-1H-indazol-6-yl)-2-(piperazin-1-yl)oxazole-4-carboxamide;
(S)-N-(1-ethyl-5-(3-hydroxypyrrolidin-1-yl)-1H-indazol-6-yl)-2-(2-methylpyridin-4-yl)oxazole-4-carboxamide hydrochloride;
(S)-N-(1-cyclopropyl-5-(3-hydroxypyrrolidin-1-yl)-1H-indazol-6-yl)-2-(2-methylpyridin-4-yl)oxazole-4-carboxamide hydrochloride;
(S)-N-(5-(3-hydroxypyrrolidin-1-yl)-1-methyl-1H-indazol-6-yl)-2-(1,2,3,6-tetrahydropyridin-4-yl)oxazole-4-carboxamide hydrochloride;
(S)-N-(5-(3-hydroxypyrrolidin-1-yl)-1-methyl-1H-indazol-6-yl)-2-(2-methylpyrimidin-4-yl)oxazole-4-carboxamide;
(S)-N-(5-(3-hydroxypyrrolidin-1-yl)-1-methyl-1H-indazol-6-yl)-4-methyl-2-(2-methylpyridin-4-yl) oxazole-5-carboxamide;

-continued (S)-N-(5-(3-hydroxypyrrolidin-1-yl)-1-methyl-1H-indazol-6-yl)-2-(piperidin-4-yl)oxazole-4-carboxamide hydrochloride;
N-(5-(3-hydroxy-8-azabicyclo[3.2.1]octan-8-yl)-1-methyl-1H-indazol-6-yl)-2-(2-methylpyridin-4-yl)oxazole-4-carboxamide;
(S)-N-(5-(3-hydroxypyrrolidin-1-yl)-1-methyl-1H-indazol-6-yl)-2-(2-methylpyridin-4-yl) oxazole-5-carboxamide;
N-(5-(4-hydroxy-4-(hydroxymethyl)piperidin-1-yl)-1-methyl-1H-indazol-6-yl)-2-(2-methylpyridin-4-yl)oxazole-4-carboxamide hydrochloride;
(S)-N-(5-(3-hydroxypyrrolidin-1-yl)-1-methyl-1H-indazol-6-yl)-5-methyl-2-(2-methylpyridin-4-yl)oxazole-4-carboxamide;
(S)-2-(2-ethylpyridin-4-yl)-N-(5-(3-hydroxypyrrolidin-1-yl)-1-methyl-1H-indazol-6-yl)oxazole-4-carboxamide;
2-(2-aminopyridin-4-yl)-N-(5-(4-(hydroxymethyl)piperidin-1-yl)-1,3-dimethyl-1H-indazol-6-yl)oxazole-4-carboxamide hydrochloride;
(S)-N-(5-(3-hydroxypyrrolidin-1-yl)-1-(piperidin-4-ylmethyl)-1H-indazol-6-yl)-2-(2-methylpyridin-4-yl)oxazole-4-carboxamide;
N-(5-(4-(hydroxymethyl)piperidin-1-yl)-1,3-dimethyl-1H-indazol-6-yl)-2-(2-methylpyridin-4-yl)oxazole-4-carboxamide;
(S)-2-(2-cyclopropylpyridin-4-yl)-N-(5-(3-hydroxypyrrolidin-1-yl)-1-methyl-1H-indazol-6-yl)oxazole-4-carboxamide; and
N-(5-(4-hydroxypiperidin-1-yl)-2-methyl-2H-indazol-6-yl)pyrazolo[1,5-a]pyrimidine-3-carboxamide;

Pharmaceutical Compositions

In certain embodiments, the present methods include a pharmaceutical composition comprising the compound as disclosed herein, optionally admixed with a pharmaceutically acceptable carrier or diluent.

As used herein, the term "composition" is intended to encompass a product comprising the specified ingredients in the specified amounts, as well as any product which results, directly or indirectly, from combination of the specified ingredients in the specified amounts.

As used herein, the term "pharmaceutical composition" refers to a composition(s) containing a therapeutically effective amount of at least one compound of formula (I) or its pharmaceutically acceptable salt; and a conventional pharmaceutically acceptable carrier.

The pharmaceutical composition(s) of the present invention can be administered orally, for example in the form of tablets, coated tablets, pills, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of ointments or creams or transdermals, in the form of patches, or in other ways, for example in the form of aerosols or nasal sprays.

The pharmaceutical composition(s) usually contain(s) about 1% to 99%, for example, about 5% to 75%, or from about 10% to about 30% by weight of the compound of formula (I) or pharmaceutically acceptable salts thereof. The amount of the compound of formula (I) or pharmaceutically acceptable salts thereof in the pharmaceutical composition (s) can range from about 1 mg to about 1000 mg or from about 2.5 mg to about 500 mg or from about 5 mg to about 250 mg or in any range falling within the broader range of 1 mg to 1000 mg or higher or lower than the afore mentioned range.

The present invention also provides methods for formulating the disclosed compounds as for pharmaceutical administration.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters.

In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate;

(13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, about 0.1 to about 99.5%

(more preferably, about 0.5 to about 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The compounds of the present invention may be administered in combination with one or more other drugs (1) to complement and/or enhance prevention and/or therapeutic efficacy of the preventive and/or therapeutic drug effect of the compound of the present invention, (2) to modulate pharmacodynamics, improve absorption improvement, or reduce dosage reduction of the preventive and/or therapeutic compound of the present invention, and/or (3) to reduce or ameliorate the side effects of the preventive and/or therapeutic compound of the present invention. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds. The respective compounds may be administered by the same or different route and the same or different method.

A concomitant medicine comprising the compounds of the present invention and other drug may be administered as a combination preparation in which both components are contained in a single formulation, or administered as separate formulations. The administration by separate formulations includes simultaneous administration and or administration of the formulations separated by some time intervals. In the case of the administration with some time intervals, the compound of the present invention can be administered first, followed by another drug or another drug can be administered first, followed by the compound of the present invention, so long as the two compounds are simultaneously active in the patient at least some of the time during the conjoint therapy. The administration method of the respective drugs may be administered by the same or different route and the same or different method.

The dosage of the other drug can be properly selected, based on a dosage that has been clinically used, or may be a reduced dosage that is effective when administered in combination with a compound of the present invention. The compounding ratio of the compound of the present invention and the other drug can be properly selected according to age and weight of a subject to be administered, administration method, administration time, disorder to be treated, symptom and combination thereof. For example, the other drug may be used in an amount of about 0.01 to about 100 parts by mass, based on 1 part by mass of the compound of the present invention. The other drug may be a combination of two or more kind of arbitrary drugs in a proper proportion. The other drug that complements and/or enhances the preventive and/or therapeutic efficacy of the compound of the present invention includes not only those that have already been discovered, but those that will be discovered in future, based on the above mechanism.

In certain embodiments, a compound of the invention may be conjointly administered with non-chemical methods of cancer treatment. In certain embodiments, a compound of the invention may be conjointly administered with radiation therapy. In certain embodiments, a compound of the invention may be conjointly administered with surgery, with thermoablation, with focused ultrasound therapy, with cryotherapy, or with any combination of these.

Methods of Treatment

Acute myeloid leukemia is a cancer of the myeloid line of blood cells, characterized by the rapid growth of abnormal white blood cells that build up in the bone marrow and interfere with the production of normal blood cells. AML is the most common acute leukemia affecting adults, and its incidence increases with age. Although AML is a relatively rare disease, it accounts for roughly 1.2% of cancer deaths in the United States.

The symptoms of AML are caused by replacement of normal bone marrow with leukemic cells, which causes a drop in red blood cells, platelets, and normal white blood cells. Several risk factors and chromosomal abnormalities have been identified, but the specific cause is not clear. As an acute leukemia, AML progresses rapidly and is typically fatal within weeks or months if left untreated. AML differs from chronic myelogenous leukemia (CML) because cellular differentiation is not the same. AML involves higher percentages of dedifferentiated and undifferentiated cells, including more blasts (myeloblasts, monoblasts, and megakaryoblasts).

Diagnosis of AML often begins with an abnormal result on a complete blood count. While an excess of abnormal white blood cells (leukocytosis) is a common finding, and leukemic blasts are sometimes seen, AML can also present with isolated decreases in platelets, red blood cells, or even with a low white blood cell count (leukopenia). While a presumptive diagnosis of AML can be made by examination of the peripheral blood smear when there are circulating leukemic blasts, a definitive diagnosis usually requires an adequate bone marrow aspiration and biopsy.

Genetic studies may also be performed to look for specific mutations in genes such as FLT-3 or the genes that regulate FLT-3 expression, which may influence the outcome of the disease. Indeed, the ability of many of the compounds disclosed herein to inhibit FLT-3 is believed to contribute to their particular efficacy against AML, which is known to be sensitive to FLT-3 inhibition. Some patients may develop resistance to treatment with a FLT-3 inhibitor due to mutations that arise in the FLT-3 gene. Such FLT-3 mutations include, but are not limited to, D835H, D835V, D835Y, K663Q, N841I, internal tandem duplication (ITD), ITD and D835V, and ITD and F691L. However, compounds as disclosed herein have demonstrated efficacy against AML that has developed resistance against treatment with FLT-3 inhibitors. Accordingly, in some embodiments, disclosed compounds are effective in treating AML that is resistant to a FLT-3 inhibitor, such as AML that is characterized by cells having one or more of these mutations.

The malignant cell in AML is the myeloblast. In normal hematopoiesis, the myeloblast is an immature precursor of myeloid white blood cells; a normal myeloblast will gradually mature into a mature white blood cell. In AML, though, a single myeloblast accumulates genetic changes which "freeze" the cell in its immature state and prevent differentiation. Such a mutation alone does not cause leukemia; however, when such a "differentiation arrest" is combined with other mutations which disrupt genes controlling proliferation, the result is the uncontrolled growth of an immature clone of cells, leading to the clinical entity of AML.

Myelodysplastic syndromes (MDS) are a group of cancers in which immature blood cells in the bone marrow do not mature and become healthy blood cells. Some types may develop into acute myeloid leukemia. Problems with blood cell formation result in some combination of low red blood cells, low platelets, and low white blood cells. Some types have an increase in immature blood cells, called blasts, in the bone marrow or blood. The types of MDS are based on specific changes in the blood cells and bone marrow.

MDS is thought to arise from mutations in the multipotent bone marrow stem cell, but the specific defects responsible for these diseases remain poorly understood. Differentiation of blood precursor cells is impaired, and there is a significant increase in levels of apoptotic cell death in bone marrow cells. Clonal expansion of the abnormal cells results in the production of cells which have lost the ability to differentiate. If the overall percentage of bone marrow myeloblasts rises over a particular cutoff, such as 20-30%, then transformation to acute myelogenous leukemia is said to have occurred. The progression of MDS to AML indicates how a series of mutations can occur in an initially normal cell and transform it into a cancer cell.

IRAK-1 is known to be overexpressed in AML and MDS, and inhibition of IRAK-1 has been demonstrated to cause apoptosis in MDS cell lines. See, e.g., Rhyasen, G. W., et al. *Cancer Cell* 2013 24:90-104; Rhyasen, G. W., et al. *British J. Cancer* 2014 pp. 1-6. The potent activity of the disclosed compounds, including compounds that are not potent inhibitors of IRAK-1, in affecting AML cell lines, such as MV4-11 and MOLM-13, indicates that IRAK-4 is an attractive and effective target for AML and MDS in its own right.

Disclosed herein are methods for treating or preventing acute myeloid leukemia. These methods may be equally applicable to treating or preventing myelodysplastic syndrome. Similarly, these methods may be equally applicable to treating or preventing multiple myeloma. In certain embodiments, the present invention relates to a compound, or a pharmaceutically acceptable salt thereof as disclosed herein for treating or preventing AML and/or MDS. In certain embodiments, the present invention relates to use of a compound or a pharmaceutically acceptable salt thereof as disclosed herein for the preparation of a medicament for treating or preventing AML and/or MDS.

Compounds suitable for the compositions and methods disclosed herein can be found in are disclosed in WO2015/104662, WO2015/104688, and WO2015/193846, each of which is incorporated by reference in its entirety, and in particular for the compounds disclosed therein as IRAK4 inhibitors.

EXAMPLES

Compound A

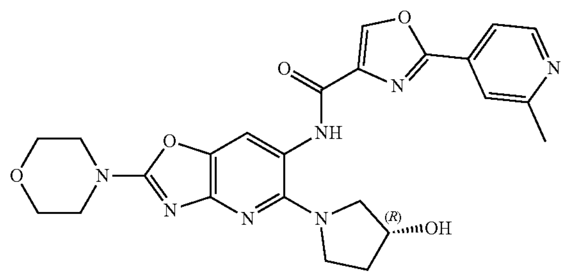

Compound B

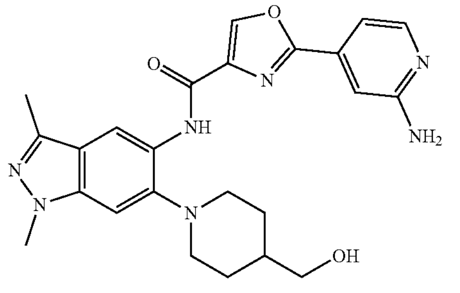

Example 1: FLT-3 Inhibition by Compound A

Inhibition of FLT-3 wild type by the compounds was tested using the substrate peptide EAIYAAPFAKKK. Flt3 (h) (14-500, GenBank NM_004119) was incubated with 8 mM MOPS pH 7.0, 0.2 mM EDTA, 50 μM EAIYAAP-FAKKK, 10 mM magnesium acetate and [gamma-33P]-ATP (specific activity and concentration as required). The reaction was initiated by the addition of the Mg/ATP mix. After incubation for 40 minutes at room temperature, the reaction was stopped by the addition of phosphoric acid to a concentration of 0.5%. 10 μL of the reaction was then spotted onto P30 filtermat and washed four times for 4 minutes in 0.425% phosphoric acid and once in methanol prior to drying and scintillation counting.

Compound A was tested against Flt-3 using the Eurofins standard KinaseProfiler assay as depicted above. Compound A was also tested against IRAK1 and Flt-3 (D835Y) using the same protocol with the substrates myelin basic protein (MBP) and EAIYAAPFAKKK respectively. Protein kinases (with the exception of ATM(h) and DNA-PK(h)) were assayed in a radiometric format, whereas lipid kinases, ATM(h), ATR/ATRIP(h) and DNA-PK(h) were assayed using an HTRF® format.

Compound A was prepared to the 50× stock of test compound was added to the assay well, before a reaction mix containing the enzyme and substrate was added. The reaction was initiated by the addition of ATP at the selected concentration. There was no pre-incubation of the compound with the enzyme/substrate mix prior to ATP addition. a working stock of 50× final assay concentration in 100% DMSO.

Results are expressed as kinase activity remaining, as a percentage of the DMSO control. This is calculated using the following formula:

$$\frac{\text{Mean of Sample Counts—Mean of Blank Counts}}{\text{Mean of Control Counts}}$$

For $IC_{50}$ determinations, data were analyzed using XLFit version 5.3 (ID Business Solutions). Sigmoidal dose-response (variable slope) curves are fit based on the mean result for each test concentration using non-linear regression analysis. Where the top and/or bottom of the curve fall >10% out with 100 and 0, respectively, either or both of these limits may be constrained at 100 and 0, provided that the QC criterion on R2 is met. Table 1 provides $IC_{50}$ data on representative kinase inhibition by Compound A.

TABLE 1

| Kinase | $IC_{50}$ (nM) |
|---|---|
| IRAK4 | 37 |
| IRAK1 | >10,000 |
| FLT3 (D835Y) | 11 |
| FLT3 | 82 |

Compound A was also tested against each of the selected kinases using the DiscoverX standard KINOMEscan and KdELECT assays and following the relevant standard operating procedures. See, e.g., *Nat. Biotechnol.* 2011, 29(11): 1046-51. KINOMEscan and KdELECT is based on a competition binding assay that quantitatively measures the ability of a compound to compete with an immobilized, active-site directed ligand. The assay is performed by combining three components: DNA-tagged kinase; immobilized ligand; and a test compound. The ability of the test compound to compete with the immobilized ligand is measured via quantitative PCR of the DNA tag. Binding constants (Kds) were calculated with a standard dose-response curve.

FIG. 1 shows the activity of Compound A against IRAK1, IRAK4 and numerous variants of FLT-3, indicating its potency as a dual IRAK/FLT-3 inhibitor. It is expected that structurally analogous compounds possess this dual activity to a similar extent.

For example, Compound A shows exceptional binding to FLT-3 with ITD mutations and with mutations in the activation loop, such as D835Y. These mutations occur in one-third of all treatment-naive AML patients. Known inhibitors of activation loop mutated FLT-3 are not equipotent. See, e.g., Nguyen, B., et al., *Oncotarget* 2017 pgs. 1-14; Nagoya, *J. Med. Sci.* 2015 77:7-17. In contrast, Compound A binds D835Y mutant FLT-3 at 2.5 nM, and ITD mutant FLT-3 at 7.8 nM.

Example 2: AML Model MV4-11 In Vitro Assay

The CellTiter Glo Luminescent cell viability assay is a highly sensitive homogenous assay to determine the number of viable cells in culture based on quantitation of ATP levels in metabolically active cells. Addition of CTG reagent results in cell lysis and generation of a luminescent signal proportional to the amount of ATP present. The amount of ATP is proportional to the number of cells present. The luminescence is measured using a multilabel reader capable of measuring luminescence. An increase or decrease in cell numbers results in a concomitant change in luminescence level, indicating the effect of the test material on cellular proliferation.

Preparation of Solutions/Reagents

Preparation of CTG Reagent

CellTiter-Glo buffer was thawed and equilibrated to room temperature. Lyophilized CellTiter-Glo substrate was brought to room temperature. CTG reagent is prepared by mixing the CellTiter-Glo buffer (Promega Cat #G7572) into an amber bottle containing CellTiter-Glo substrate to reconstitute the lyophilized enzyme/substrate mixture. Both Buffer and the lyophilized substrate are supplied with the kit.

Media Preparation:

Add 1% Penicillin Streptomycin and 10% FBS to commercially available liquid IMDM (Iscove's Modified Dulbecco's Medium, Invitrogen Cat #12440046).

Preparation of 1×PBS (Phosphate Buffered Saline):

One pouch of PBS powder (Sigma: Cat #P3813) was dissolved in 1 L MiliQ water. DMSO is used a vehicle do dissolve the test item.

Procedure ($IC_{50}$ Determination)

1. MV4-11 cells were counted and re-suspended to a density of 0.1×106 cells/ml in complete IMDM medium. 95 μL of this cell suspension was added per well of a 96-well plate (black plate with clear bottom) to seed ~0.1×105 cells per well. The plates were incubated at 37° C. under a humidified atmosphere of 5% CO2 for ~2 hours before compound addition.
2. Test compounds were dissolved in 100% DMSO to generate a 2/6/10/20 mM stock solution. A 200× concentration of the required final concentrations was prepared in DMSO. 10 μL of each concentration (200×) was then diluted in 90 μL of serum-free IMDM to prepare an intermediate concentration of 20× in medium. The DMSO concentration in this step was 10% (Intermediate dilution). 5 μL of each intermediate dilution was then added in triplicates to cells previously seeded in 96-well plate. The final DMSO concentration was 0.5% in the experimental wells. Cells treated with 0.5% DMSO served as a positive control. 100 μL of complete IMDM medium served as media blank for data analysis. 200 μL of 1×PBS was added in all corner wells of the assay plate to avoid evaporation of media in experimental wells. Plates were then incubated for 72 hours in an incubator with 5% $CO_2$ at 37° C.
3. To terminate the assay, 50 μL of CTG reagent was added to each well and the plate was incubated at room temperature for 15 minutes on a shaker. The plate was read using the luminescence mode on a multilabel reader capable of measuring luminescence. The luminescence values were plotted against respective concentrations of the test item using GraphPad Prism to calculate the $IC_{50}$ value for the test item.

Percent Inhibition is Calculated as Follows:

Percent (%) Inhibition was calculated by normalizing DMSO control values to 0% inhibition using the formula:

$$\%\ \text{Inhibition}=100-(L_{test\ compound\text{-}blank})/(L_{positive\ control\text{-}blank})*100$$ where $L$ is Luminescence Experimental wells contained cells, test compound, IMDM medium and 0.5% DMSO. Positive control wells contained cells, IMDM medium and 0.5% DMSO. Blank control wells contained IMDM medium alone.

The $IC_{50}$ values for the following compounds in μM are given in Table 2. A is <0.05 μM, B is 0.05 to 0.5 μM, and C is >0.5 μM.

TABLE 2

| Structure | MV4-11 $IC_{50}$ in μM |
|---|---|
| 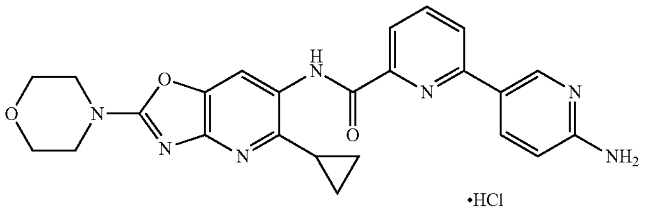 [SMILES: Nc1ccc(-c2cccc(C(=O)Nc3cc4oc(N5CCOCC5)nc4nc3C3CC3)n2)cn1 ; Cl] | C |
| 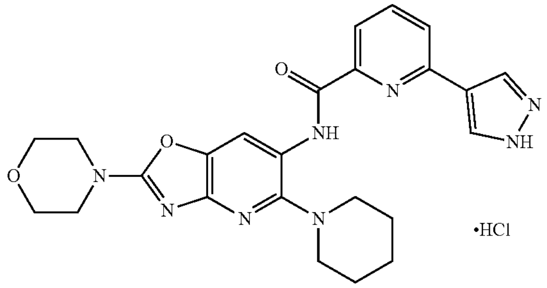 [SMILES: O=C(Nc1cc2oc(N3CCOCC3)nc2nc1N1CCCCC1)c1cccc(-c2cn[nH]c2)n1 ; Cl] | A |

TABLE 2-continued
| Structure | MV4-11 IC$_{50}$ in μM |
| --- | --- |
| 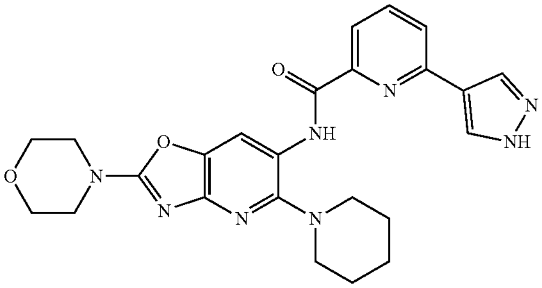 [SMILES: O=C(Nc1cc2oc(N3CCOCC3)nc2nc1N1CCCCC1)c1cccc(-c2cn[nH]c2)n1] | A |
| 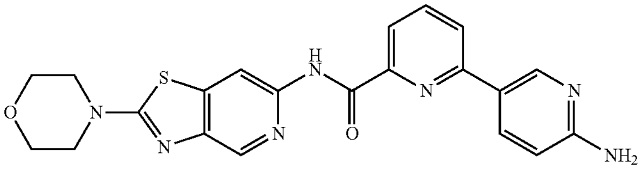 [SMILES: Nc1ccc(-c2cccc(C(=O)Nc3cc4sc(N5CCOCC5)nc4cn3)n2)cn1] | B |
| 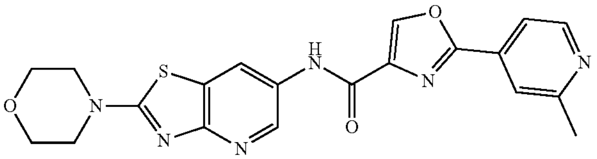 [SMILES: Cc1cc(-c2nc(C(=O)Nc3cnc4nc(N5CCOCC5)sc4c3)co2)ccn1] | A |
| 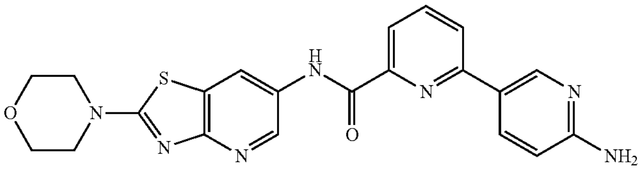 [SMILES: Nc1ccc(-c2cccc(C(=O)Nc3cnc4nc(N5CCOCC5)sc4c3)n2)cn1] | C |
| 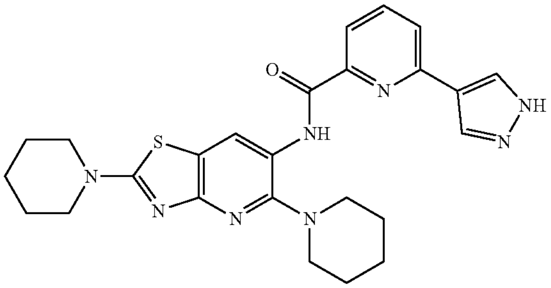 [SMILES: O=C(Nc1cc2sc(N3CCCCC3)nc2nc1N1CCCCC1)c1cccc(-c2cn[nH]c2)n1] | B |
| 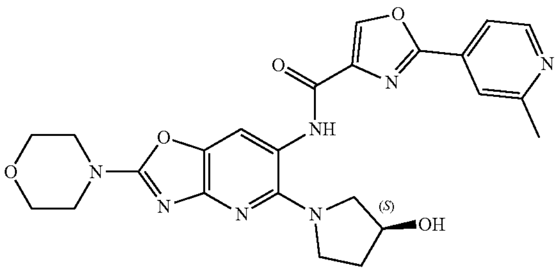 | A |

TABLE 2-continued
| Structure | MV4-11 $IC_{50}$ in μM |
|---|---|
| 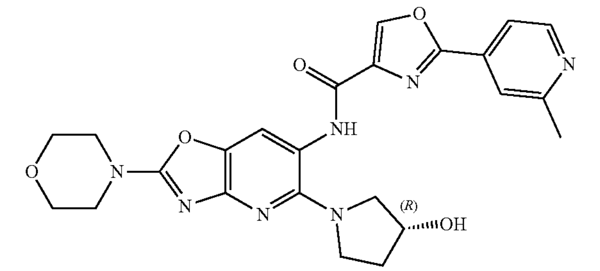 | A |
| 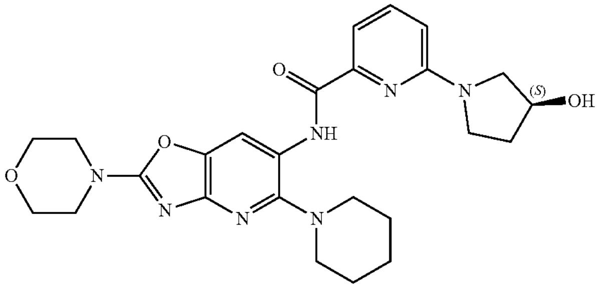 | C |
| 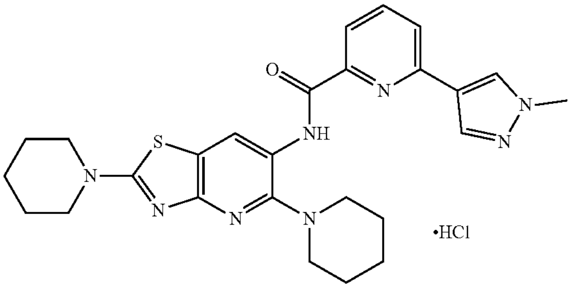 [SMILES: Cn1cc(-c2cccc(C(=O)Nc3cc4sc(N5CCCCC5)nc4nc3N3CCCCC3)n2)cn1 ; Cl] •HCl | A |
| 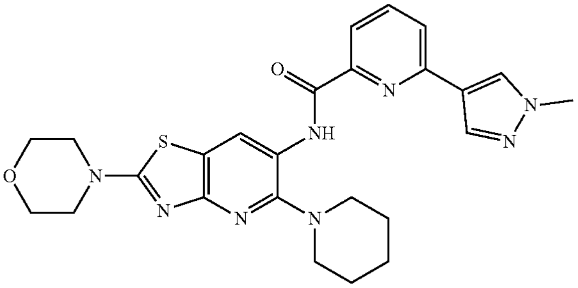 [SMILES: Cn1cc(-c2cccc(C(=O)Nc3cc4sc(N5CCOCC5)nc4nc3N3CCCCC3)n2)cn1] | A |
| 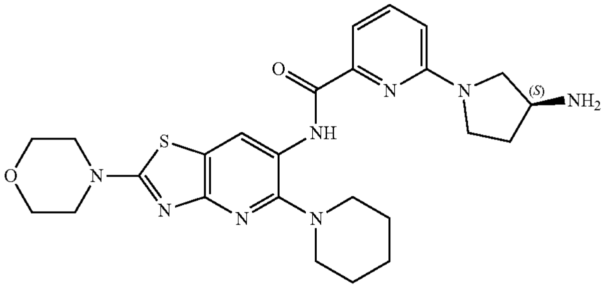 | C |

TABLE 2-continued
| Structure | MV4-11 $IC_{50}$ in μM |
| --- | --- |
| 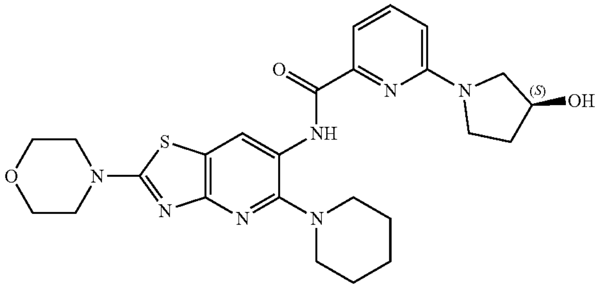 | C |
| 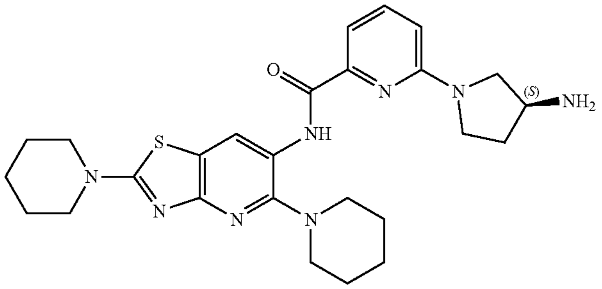 | C |
| 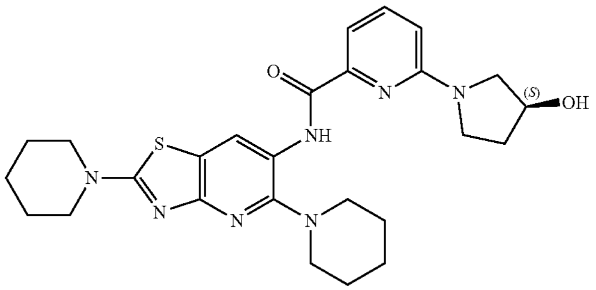 | C |
| 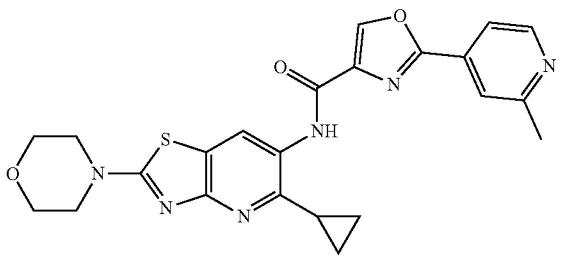 [SMILES: Cc1cc(-c2nc(C(=O)Nc3cc4sc(N5CCOCC5)nc4nc3C3CC3)co2)ccn1] | A |
| 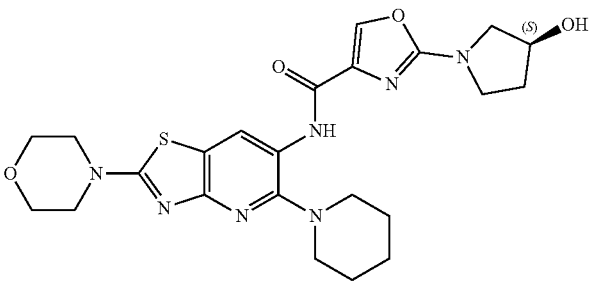 | A |

TABLE 2-continued
| Structure | MV4-11 $IC_{50}$ in μM |
|---|---|
| 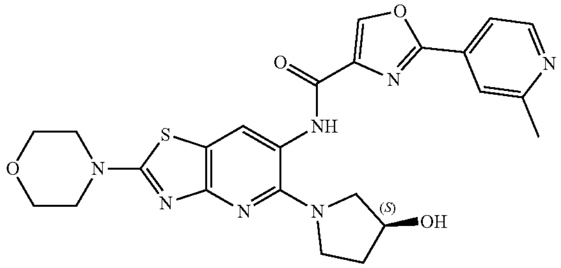 | A |
| 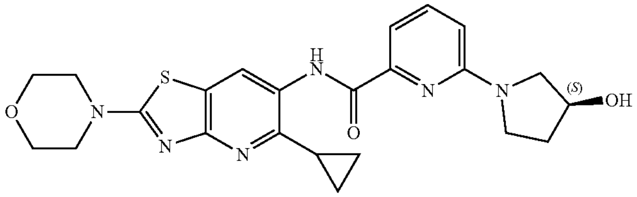 | C |
| 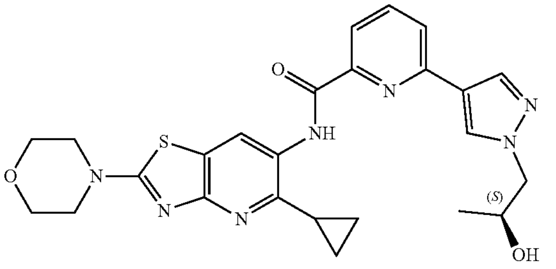 | A |
| 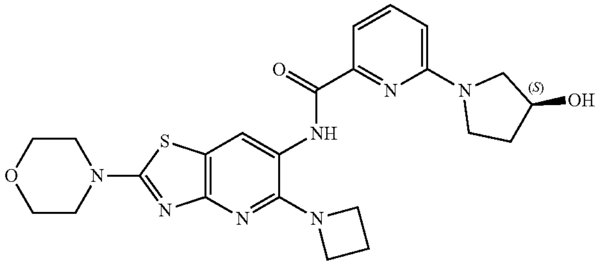 | C |
| 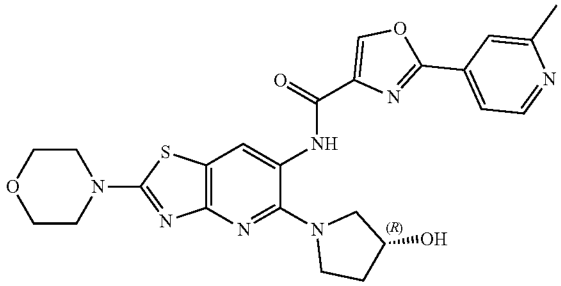 | A |

TABLE 2-continued
| Structure | MV4-11 $IC_{50}$ in μM |
|---|---|
| 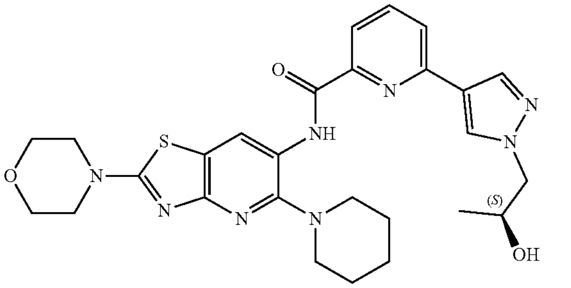 | A |
| 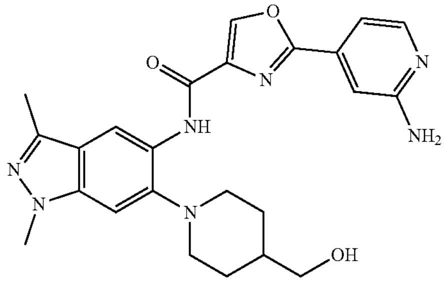 [SMILES: Cc1nn(C)c2cc(N3CCC(CO)CC3)c(NC(=O)c3coc(-c4ccnc(N)c4)n3)cc12] | A |
| 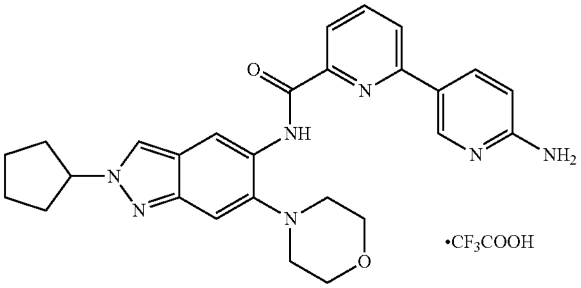 [SMILES: Nc1ccc(-c2cccc(C(=O)Nc3cc4cn(C5CCCC5)nc4cc3N3CCOCC3)n2)cn1 ; "·CF3COOH"] •$CF_3COOH$ | A |
| 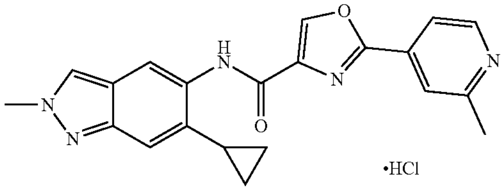 [SMILES: Cc1cc(-c2nc(C(=O)Nc3cc4cn(C)nc4cc3C3CC3)co2)ccn1 ; Cl] •HCl | A |
| 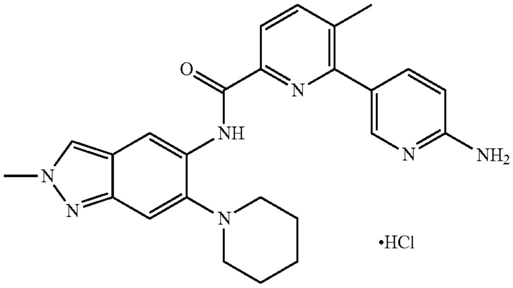 [SMILES: Cc1ccc(C(=O)Nc2cc3cn(C)nc3cc2N2CCCCC2)nc1-c1ccc(N)nc1 ; Cl] •HCl | A |

TABLE 2-continued
| Structure | MV4-11 IC$_{50}$ in μM |
| --- | --- |
| 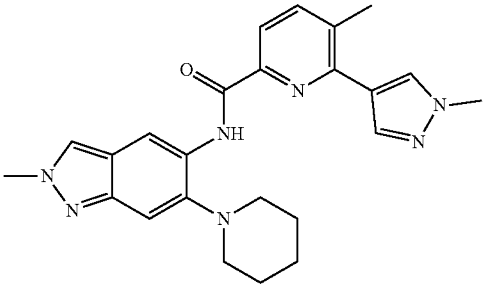 | A |
| 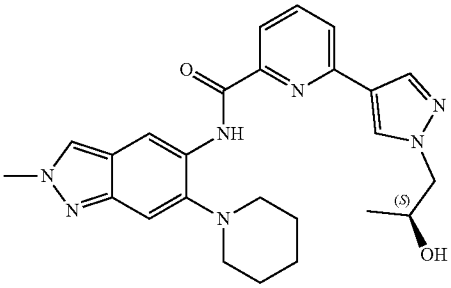 | A |
| 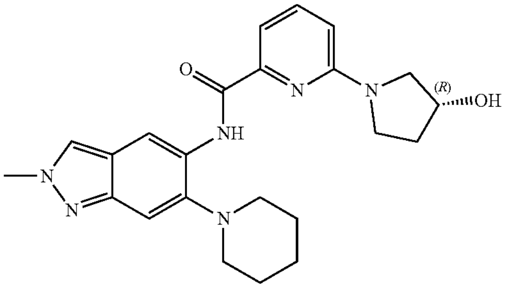 | C |
| 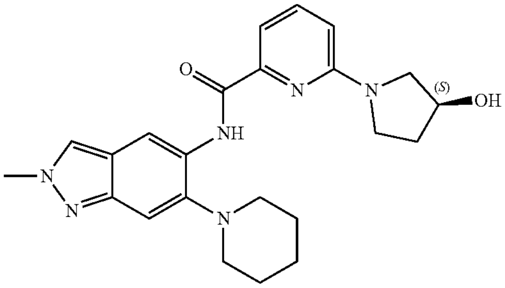 | B |
| 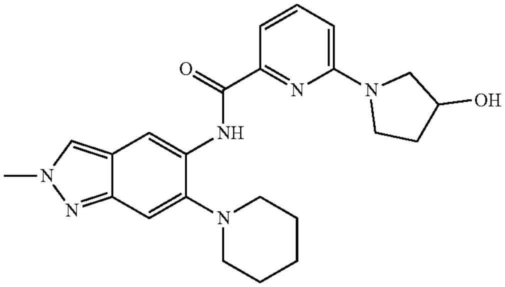 [SMILES: Cn1cc2cc(NC(=O)c3cccc(N4CCC(O)C4)n3)c(N3CCCCC3)cc2n1] | B |

TABLE 2-continued

| Structure | MV4-11 $IC_{50}$ in μM |
|---|---|
| 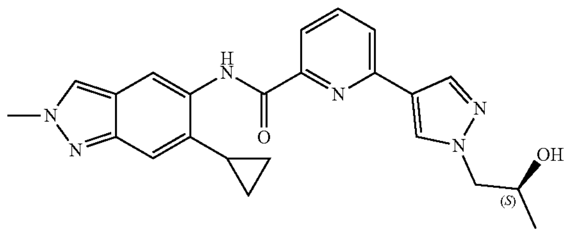 | A |

Example 3: Cellular Proliferation Inhibition in MV4-11 Xenograft Model

Figure 2B:
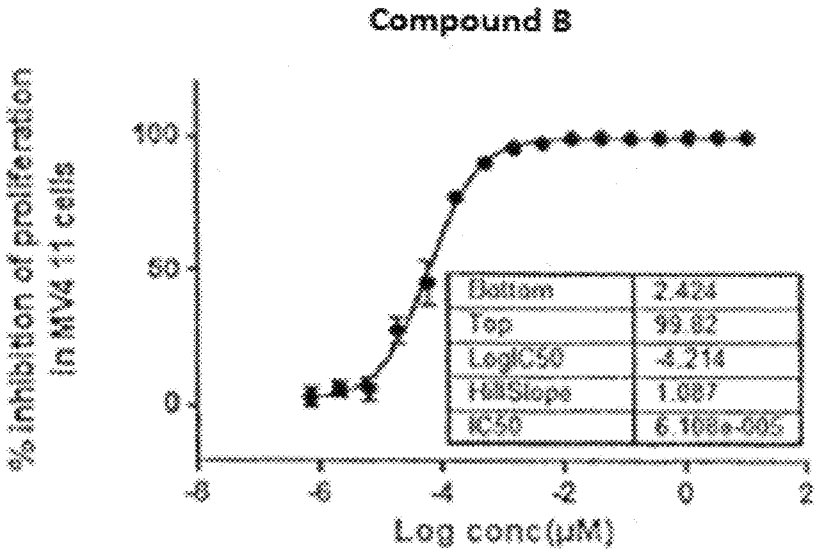
FIG. 2B depicts the % inhibition of proliferation in MV4-11 cells by Compound B.

Using the procedure of Example 2, Compounds A and B were assessed to determine the % inhibition of proliferation in MV4-11 cells. The $IC_{50}$ of Compound A was 0.031 μM (FIG. 2A) and Compound B was 6.1e-005 μM (FIG. 2B).

Example 4: In Vivo Tumor Growth Inhibition in AML Xenograft Model MV4-11

Using an AML Xenograft Model MV4-11 protocol, Compound A was evaluated at 12.5, 25, and 50 mpk doses. ND-2158 at 100 mpk was used as a control.

The antitumor activity of Compound A was evaluated in male athymic nude mice. MV4-11 cells were grown in Iscove's Modified Dulbecco's medium supplemented with 10% FBS and 1% penicillin streptomycin. To establish tumors, 15×106 MV4-11 cells were injected subcutaneously in 200 μl of 1:1 HBSS and ECM gel into the right flank of the athymic nude mice. Animals were randomized based on tumor volumes. For 21 days, Compound A was dosed orally once daily and ND-2158 was dosed once daily by i.p. route. Treatments were initiated when the average tumor volume sizes were 333 $mm^3$. Tumor volumes were measured three times a week and body weights were monitored daily. Compound A at 12.5, 25, and 50 mg/kg and ND-2158 100 mg/kg treatments were well tolerated without any treatment related clinical signs and gross pathological changes.

Figure 3:
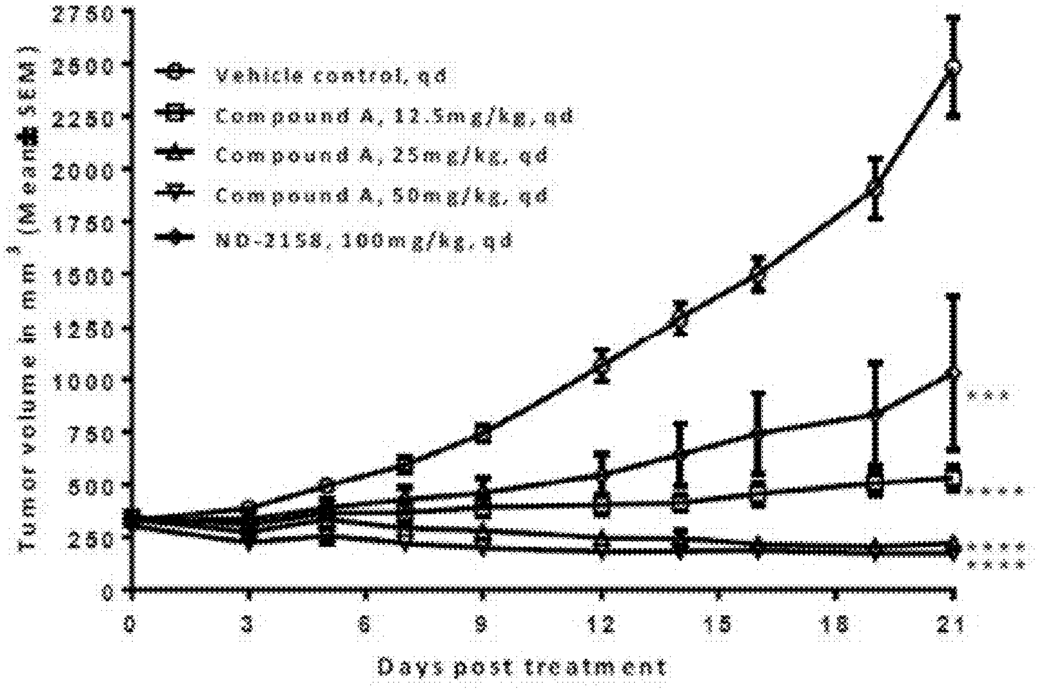
FIG. 3 depicts the increase in tumor growth inhibition with increasing doses of Compound A at 12.5, 25, and 50 mpk.
Figure 4:
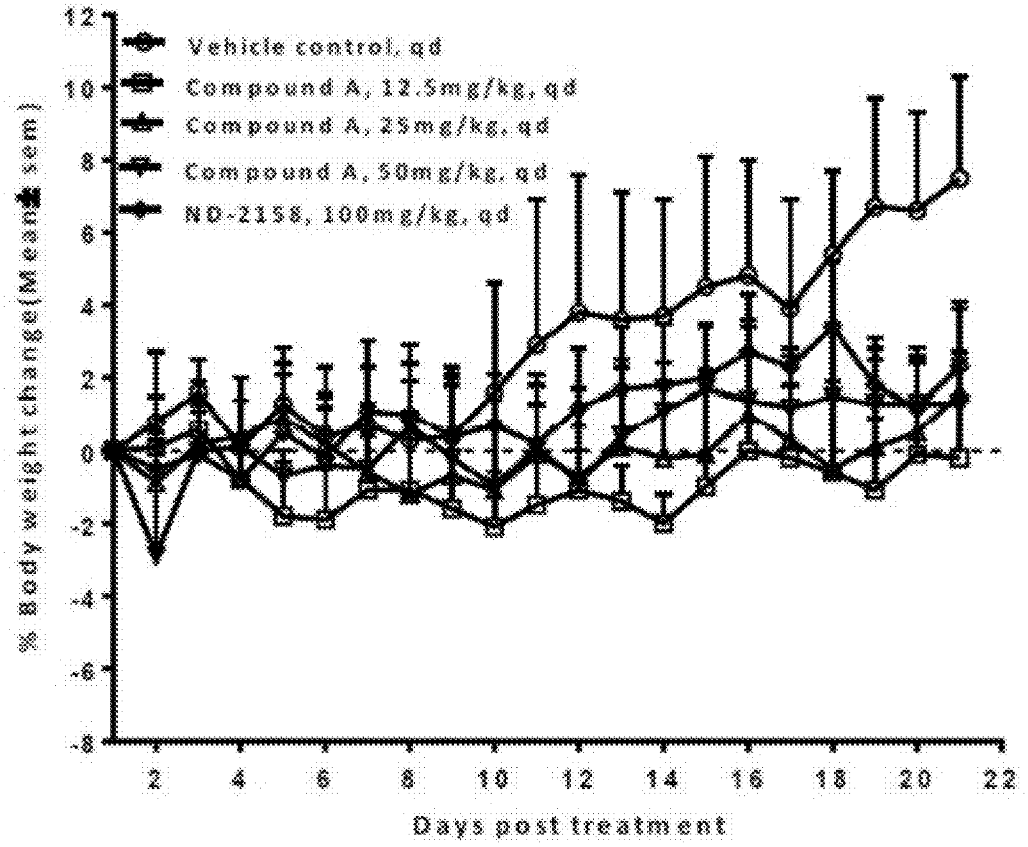
FIG. 4 depicts the static body weight of animals in an MV4-11 in vivo xenograft model.

FIG. 3 depicts the increase in tumor growth inhibition with increasing doses of Compound A. Tumor growth stasis was achieved at 12.5 mpk and tumor regression was seen at 25 and 50 mpk after 21 days of treatment. Compound A at 12.5 mg/kg treatment resulted in 92% tumor growth inhibition. Compound A at 25 mg/kg and 50 mg/kg treatments resulted in partial tumor regression. ND-2158 100 mg/kg treatment resulted in 68% tumor growth inhibition. No body weight reduction was observed, as shown in FIG. 4.

Example 5: Anti-Proliferative Activity in AML Xenograft Models MV4-11 and MOLM-13

The same procedure was used for both the MV4-11 cells and MOLM-13 cells. Each cell line has an ITD mutation in the FLT-3 kinase.

The cells were grown to ~80% confluence, split in half and grown overnight. The cells were seeded at a density of 5,000 cells/well in a volume of 150 μL into a 96-well black plate in all wells except columns 1 and 12 and rows A and H. They were incubated overnight in 10% serum and HBSS was added to wells on the periphery. In a deep 96-well plate, 1000 μL of 10% FBS was added into wells B2 and D2. 750 μL of 10% FBS, 1% DMSO medium per well was added in row B except well B2. 5 μL of 20 mM compound was added into well B2. 250 μL was transferred from column 2 to column 3 and mixed. The process was repeated until column G to give a 1:4 dilution. 15 μL of compound mixture was added to each well of the cell plate (135 μL volume). The CellTiter Glo assay described in Example 2 was used to determine the $IC_{50}$ value for Compound A in each cell line. Compound A had an $IC_{50}$ of 0.07 μM in the MV4-11 cell line and 0.19 μM in the MOLM-13 cell line.

Figure 5A:
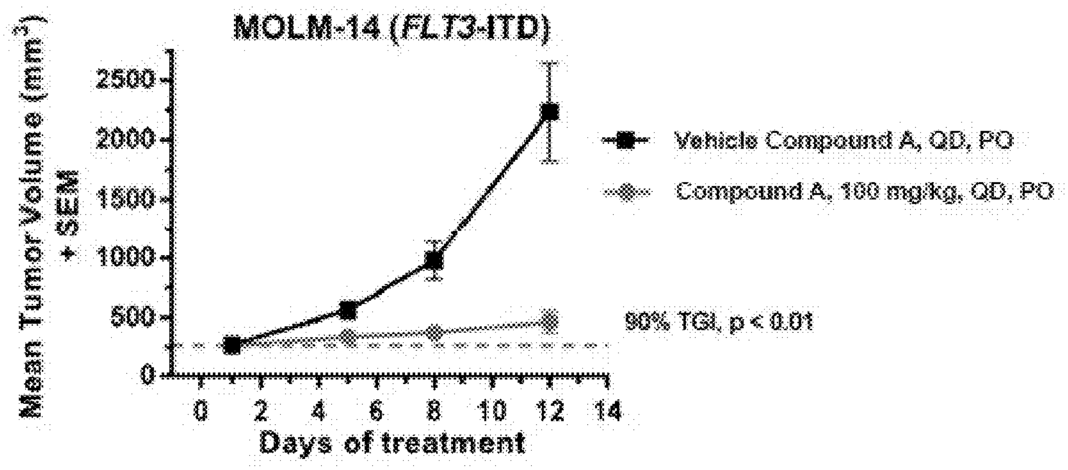
FIG. 5A depicts the percent tumor growth inhibition (% TGI) in mice having a subcutaneous MOLM-14 FLT3-ITD tumor.
Figure 5B:
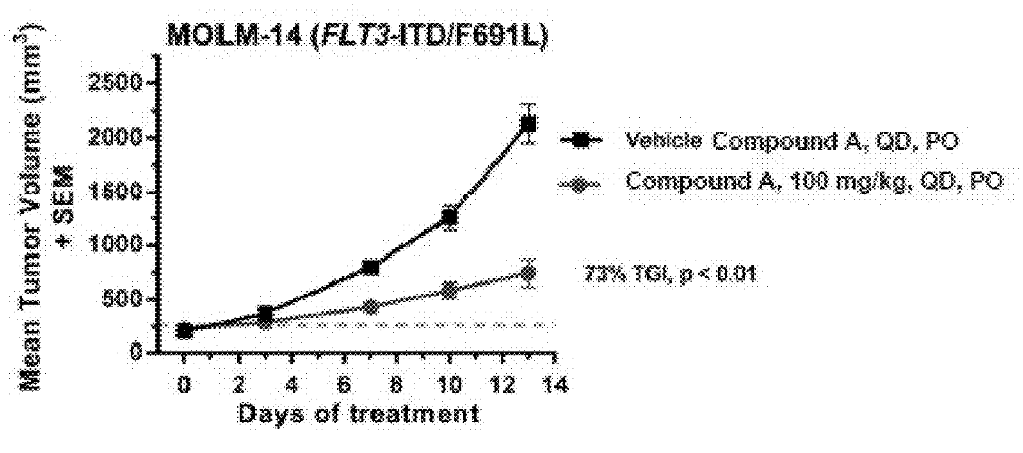
FIG. 5B depicts the percent tumor growth inhibition (% TGI) in mice having a MOLM-14 FLT3-ITD/F691L tumor.
Figure 5C:
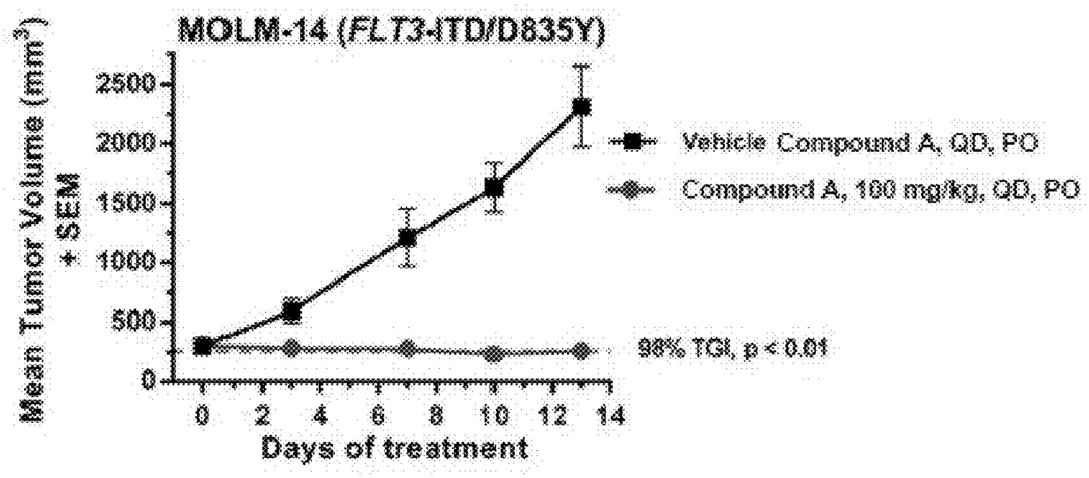
FIG. 5C depicts the percent tumor growth inhibition (% TGI) in mice having a MOLM-14 FLT3-ITD/D835Y tumor.

Example 6: In Vivo Efficacy of Compound a in MOLM-14 FLT3-ITD and MOLM-14 FLT3-ITD/KD (Kinase Domain) Mouse Xenograft Tumor Models Compound A was administered orally at 100 mg/kg once-daily in athymic nude mice bearing subcutaneous MOLM-14 FLT3-ITD, MOLM-14 FLT3-ITD/F691L, or MOLM-14 FLT3-ITD/D835Y tumors. Compound A efficacy was compared to mice administered vehicle. As shown in FIGS. 5A, 5B, and 5C, the percent tumor growth inhibition (% TGI) was 90, 73 and 98%, respectively, after 12 or 14 days of dosing.

Example 7: Cell Viability Assay

The parental MOLM-14 cell line contained a FLT3-ITD mutation. Quizartinib-resistant MOLM-14 derivative cell lines MOLM-14 FLT3-ITD/D835Y and MOLM-14 FLT3-ITD/F691L contained a double FLT3 mutation (the original ITD mutation and a secondary mutation within the kinase domain).

All cells lines were cultured in RPMI 1640+GlutaMAX supplemented with 1× Pen-Strep and 10% FBS (referred to as media hereafter). Cells were cultured in 75 $cm^2$ or 225 $cm^2$ tissue culture flasks in a 37° C. humidified tissue culture incubator with 5% $CO_2$. Cell densities were maintained between 0.5-2.0×$10^6$ cells/mL.

Plating and Dosing

Two days before compound treatment, cells were pelleted and resuspended in fresh medium. The day of dosing, cells were counted and stained with trypan blue to determine cell viability. 5,000 viable cells were transferred in a volume of 90 μL or 135 μL per well to all wells of a 96-well tissue culture plate and returned to the tissue culture incubator. In general, two rows of each cell line to be assayed were added per plate (i.e., maximum of 3 cell lines per plate). The lower limit of viability for cells was 80% for use in this assay; the majority of cell lines exhibited >90% viability.

Compound stock solutions prepared in 100% DMSO were removed from the −80° C. freezer and thawed at room temperature before use. Unused compound was discarded. A compound dilution series was created using a 96-well plate. 40 μL of compound stock solution was transferred to well B2. 30 μL of DMSO was added to wells B3 to B11. 10 μL from well B2 was transferred to well B3, mixed by pipetting up and down 6 times resulting in a 1 in 4 dilution. Alternative volumes or dilution ratios may have been employed. Changing pipet tips between dilution steps, the dilution series was continued until well B10. Well B11 is the DMSO-treated control sample.

198 μL of media was transferred to each well of rows B-G and columns 2-11 of a new 96-well plate. 2 μL from the Compound A DMSO dilution-series plate was transferred to the corresponding wells of each row containing the 198 μL of media and mixed by pipetting 6 times, creating a 10× Compound A dilution-series dosing plate.

From the 10× Compound A dilution-series dosing plate, 10 μL or 15 μL of the diluted compounds were added to the 96-well tissue culture plate containing 90 μL or 135 μL of cells, respectively. Plates were then briefly mixed using a plate mixer at 150 rpms for two minutes. The plates were returned to a tissue culture incubator and incubated at 37° C. for 72 hr. The final concentration of DMSO added to cells was 0.1%.

Each cell line was tested in duplicate per plate, and repeated at least 3 times on different days.

Viability

After 72 h incubation, cell viability was assessed using the CellTiter-Glo Luminescent Cell Viability Assay (2.0) according to the vendor's instructions. After addition of the CellTiter-Glo reagent (1:1 volume), plates were covered with clear plate sealers, followed by mixing on a plate shaker at 150 rpm in the dark for 10 minutes at room-temperature. Luminescence readings were measured using a TopCount384 instrument.

$EC_{50}$ Calculation

The percent inhibition of the compound treated samples was determined relative to the DMSO-treated cell control samples. The percent inhibition values were used to calculate $EC_{50}$ values using GraphPad Prism 7 software. In assays where curve fitting failed to determine an $EC_{50}$ value, the concentration causing 50% inhibition by linear extrapolation was used as the $EC_{50}$ value. The mean $EC_{50}$ values from at least 3 independent viability assays performed on different days were determined.

$$MOLM-14EC_{50}=58\text{ nM}$$

$$MOLM-14FLT3-ITD/D835Y,\ EC_{50}=108\text{ nM}$$

$$MOLM-14FLT3-ITD/F691L,\ EC_{50}=2488\text{ nM}$$

INCORPORATION BY REFERENCE

All publications and patents mentioned herein are hereby incorporated by reference in their entirety as if each individual publication or patent were specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of treating Myelodysplastic syndrome (MDS) in a subject, comprising administering a compound represented by Formula II:

(II)

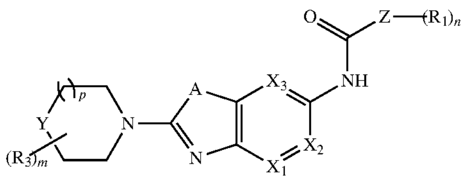

or a pharmaceutically acceptable salt thereof;

wherein the group

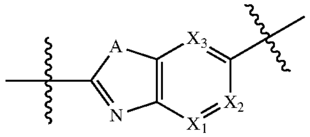

is

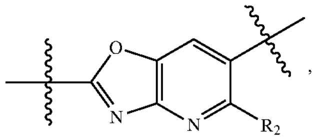

,

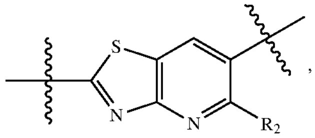

,

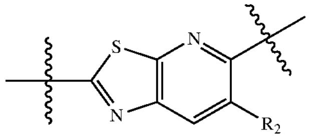

,

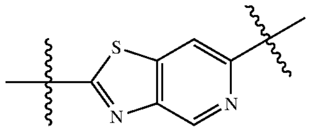

or

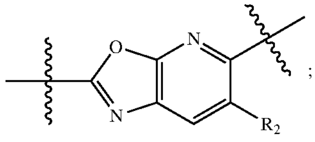

;

Y is $-CH_2-$ or O;

Z is aryl or heterocyclyl;

$R_1$, at each occurrence, is independently halo or optionally substituted heterocyclyl; wherein the optional substituent is alkyl, alkoxy, aminoalkyl, halo, hydroxyl, hydroxyalkyl or —$NR_aR_b$;

$R_2$ is hydrogen, optionally substituted cycloalkyl, optionally substituted aryl, optionally substituted heterocyclyl or —$NR_aR_b$; wherein the optional substituent is alkyl, amino, halo or hydroxyl;

$R_3$, at each occurrence, is alkyl or hydroxyl;

$R_a$ and $R_b$ are independently hydrogen, alkyl, acyl or heterocyclyl;

'm' and 'n' are independently 0, 1 or 2; and

'p' is 0 or 1.

2. The method of claim 1, wherein

Y is —$CH_2$— or O;

Z is aryl or heterocyclyl;

$R_1$, at each occurrence, is independently halo or optionally substituted heterocyclyl, wherein the optional substituent is alkyl, aminoalkyl, halo, or —$NR_aR_b$; where $R_a$ and $R_b$ are independently hydrogen, alkyl, or heterocyclyl;

$R_2$ is hydrogen, cycloalkyl, heterocyclyl or —$NR_aR_b$;

'm' is 0; and

'n' is 1.

3. The method of claim 1, wherein

Y is —$CH_2$— or O;

Z is aryl or heterocyclyl;

$R_1$, at each occurrence, is independently halo or optionally substituted heterocyclyl; wherein the optional substituent is alkyl, alkoxy, aminoalkyl, halo, hydroxyl or —$NR_aR_b$; where $R_a$ and $R_b$ are independently hydrogen, alkyl, or heterocyclyl;

$R_2$ is hydrogen, cycloalkyl, optionally substituted heterocyclyl or —$NR_aR_b$, where the optional substituent is selected from amino, halo or hydroxyl;

'm' and 'n' are independently 0, 1 or 2; and

'p' is 0 or 1.

4. The method of claim 1, wherein Z is aryl or a 5- or 6-membered heterocyclyl.

5. The method of claim 1, wherein Z is an optionally substituted heterocyclyl selected from furanyl, thienyl, pyrrolyl, pyrazolyl, imidazolyl, oxazolyl, isoxazolyl, thiazolyl, isothiazolyl, 1H-tetrazolyl, oxadiazolyl, triazolyl, pyridyl, pyrimidinyl, pyrazinyl, pyridazinyl, azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrothiophenyl, dihydropyranyl and azabicyclo[3.2.1]octanyl; each of which is optionally substituted with alkyl, alkoxy, halo, hydroxyl, hydroxyalkyl or —$NR_aR_b$; and $R_a$ and $R_b$ are independently hydrogen, alkyl or acyl.

6. The method of claim 1, wherein the compound of formula (II) is represented by formula (IIA):

(IIA)

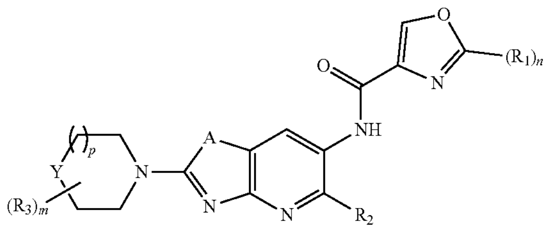

or a pharmaceutically acceptable salt thereof;

wherein A is O or S.

7. The method of claim 6, wherein

Y is —$CH_2$— or O;

$R_1$, at each occurrence, is independently halo or optionally substituted heterocyclyl, wherein the optional substituent is alkyl, aminoalkyl, halo, or —$NR_aR_b$; where $R_a$ and $R_b$ are independently hydrogen, alkyl, or heterocyclyl;

$R_2$ is hydrogen, cycloalkyl, heterocyclyl or —$NR_aR_b$;

'm' is 0; and

'n' is 1.

8. The method of claim 6, wherein

Y is —$CH_2$— or O;

$R_1$, at each occurrence, is independently halo or optionally substituted heterocyclyl; wherein the optional substituent is alkyl, alkoxy, aminoalkyl, halo, hydroxyl or —$NR_aR_b$; where $R_a$ and $R_b$ are independently hydrogen, alkyl, or heterocyclyl;

$R_2$ is hydrogen, cycloalkyl, optionally substituted heterocyclyl or —$NR_aR_b$, where the optional substituent is selected from amino, halo or hydroxyl; and 'm' and 'n' are independently 0, 1 or 2.

9. The method of claim 1, wherein the compound of formula (II) is represented by formula (IIB):

(IIB)

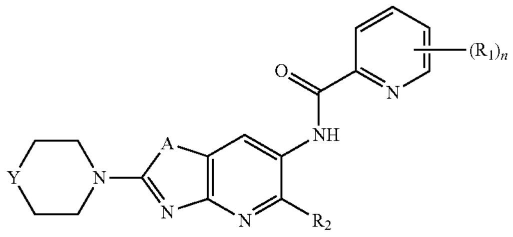

or a pharmaceutically acceptable salt thereof;

wherein A is O or S.

10. The method of claim 9, wherein

Y is —$CH_2$— or O;

$R_1$, at each occurrence, is independently halo or optionally substituted heterocyclyl, wherein the optional substituent is alkyl, aminoalkyl, halo, or —$NR_aR_b$; where $R_a$ and $R_b$ are independently hydrogen, alkyl, or heterocyclyl;

$R_2$ is hydrogen, cycloalkyl, heterocyclyl or —$NR_aR_b$; and

'n' is 1.

11. The method of claim 9, wherein

Y is —$CH_2$— or O;

$R_1$, at each occurrence, is independently halo or optionally substituted heterocyclyl; wherein the optional substituent is alkyl, alkoxy, aminoalkyl, halo, hydroxyl or —$NR_aR_b$; where $R_a$ and $R_b$ are independently hydrogen, alkyl, or heterocyclyl;

$R_2$ is hydrogen, cycloalkyl, optionally substituted heterocyclyl or —$NR_aR_b$, where the optional substituent is selected from amino, halo or hydroxyl; and 'm' and 'n' are independently 0, 1 or 2.

12. The method of claim 1, wherein the compound of formula (II) is represented by formula (IIC):

(IIC)

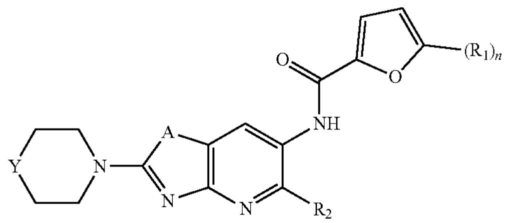

or a pharmaceutically acceptable salt thereof;

wherein A is O or S.

13. The method of claim 1, wherein $R_1$ is optionally substituted heterocyclyl; wherein the optional substituent is alkyl, alkoxy, aminoalkyl, halo, hydroxyl, hydroxyalkyl or —$NR_aR_b$; and $R_a$ and $R_b$ are independently hydrogen or acyl.

14. The method of claim 13, wherein $R_1$ is pyridyl, pyrazolyl, pyrrolidinyl or piperidinyl.

15. The method of claim 13, wherein $R_1$ is optionally substituted pyrazolyl, wherein the optional substituent is alkyl, hydroxyl or —$NR_aR_b$.

16. The method of claim 1, wherein $R_1$ is optionally substituted heterocyclyl; wherein the optional substituent is alkyl, aminoalkyl, halo, or —$NR_aR_b$; and $R_a$ and $R_b$ are independently hydrogen or acyl.

17. The method of claim 16, wherein $R_1$ is pyridyl, pyrazolyl, pyrrolidinyl or piperidinyl.

18. The method of claim 16, wherein $R_1$ is optionally substituted pyrazolyl, wherein the optional substituent is alkyl, hydroxyl or —$NR_aR_b$.

19. The method of claim 1, wherein $R_1$ is optionally substituted heterocyclyl; and the optional substituent is alkyl, aminoalkyl, halo, or —$NR_aR_b$; where $R_a$ and $R_b$ are independently hydrogen, alkyl, or heterocyclyl.

20. The method of claim 19, wherein $R_1$ is pyridyl, pyrazolyl, pyrrolidinyl or piperidinyl.

21. The method of claim 19, wherein $R_1$ is optionally substituted pyrazolyl, wherein the optional substituent is alkyl, hydroxyl or —$NR_aR_b$.

22. The method of claim 1, wherein $R_1$ is optionally substituted heterocyclyl; and the optional substituent is alkyl, alkoxy, aminoalkyl, halo, hydroxyl or —$NR_aR_b$; where $R_a$ and $R_b$ are independently hydrogen, alkyl, or heterocyclyl.

23. The method of claim 22, wherein $R_1$ is pyridyl, pyrazolyl, pyrrolidinyl or piperidinyl.

24. The method of claim 22, wherein $R_1$ is optionally substituted pyrazolyl, wherein the optional substituent is alkyl, hydroxyl or —$NR_aR_b$.

25. The method of claim 1, wherein $R_1$ is halo.

26. The method of claim 1, wherein $R_2$ is hydrogen, cycloalkyl, heterocyclyl or —$NR_aR_b$.

27. The method of claim 1 wherein $R_2$ is hydrogen, cycloalkyl, optionally substituted heterocyclyl or —$NR_aR_b$, where the optional substituent is selected from amino, halo or hydroxyl.

28. The method of claim 1, wherein $R_2$ is optionally substituted heterocyclyl selected from piperidinyl, pyrrolidinyl, morpholinyl, piperazinyl, azetidinyl, pyrazolyl, furanyl or azabicyclo[3.2.1]octanyl; wherein the optional substituent is hydroxyl, halo, alkyl or amino.

29. The method of claim 1, wherein $R_2$ is piperidinyl, pyrrolidinyl, morpholinyl, or piperazinyl.

30. The method of claim 1, wherein $R_2$ is hydrogen.

31. The method of claim 1, wherein $R_2$ is cycloalkyl.

32. The method of claim 31, wherein $R_2$ is cyclopropyl.

33. The method of claim 1, wherein $R_3$ is alkyl.

34. The method of claim 1, wherein m is 0 and p is 1.

35. The method of claim 1, wherein m is 0 or 2, and p is 0 or 1.

36. The method of claim 1, wherein the compound represented by formula (II) is selected from:

6'-amino-N-(2-morpholinooxazolo[4,5-b]pyridin-6-yl)-[2,3'-bipyridine]-6-carboxamide;
6'-amino-N-(5-cyclopropyl-2-morpholinooxazolo[4,5-b]pyridin-6-yl)-[2,3'-bipyridine]-6-carboxamide hydrochloride;
N-(5-cyclopropyl-2-morpholinooxazolo[4,5-b]pyridin-6-yl)-2-(2-methylpyridin-4-yl)oxazole-4-carboxamide hydrochloride;
N-(2,5-di(piperidin-1-yl)oxazolo[4,5-b]pyridin-6-yl)-6-(1H-pyrazol-4-yl)picolinamide hydrochloride;
N-(2,5-di(piperidin-1-yl)oxazolo[4,5-b]pyridin-6-yl)-2-(2-methylpyridin-4-yl)oxazole-4-carboxamide;
N-(2-morpholino-5-(piperidin-1-yl)oxazolo[4,5-b]pyridin-6-yl)-6-(1H-pyrazol-4-yl)picolinamide;
2-(2-methylpyridin-4-yl)-N-(2-morpholino-5-(piperidin-1-yl)oxazolo[4,5-b]pyridin-6-yl)oxazole-4-carboxamide;
6-chloro-N-(2-morpholino-5-(piperidin-1-yl)oxazolo[4,5-b]pyridin-6-yl)picolinamide;
N-(2,5-di(piperidin-1-yl)oxazolo[4,5-b]pyridin-6-yl)-6-(1-methyl-1H-pyrazol-4-yl)picolinamide;
2-(2-chloropyridin-4-yl)-N-(2,5-di(piperidin-1-yl)oxazolo[4,5-b]pyridin-6-yl)oxazole-4-carboxamide;
(S)-2-(2-methylpyridin-4-yl)-N-(2-morpholino-5-(pyrrolidin-3-ylamino)oxazolo[4,5-b]pyridin-6-yl)oxazole-4-carboxamide;
6'-amino-N-(2-morpholinooxazolo[5,4-b]pyridin-5-yl)-[2,3'-bipyridine]-6-carboxamide;
6'-amino-N-(2-morpholinothiazolo[4,5-c]pyridin-6-yl)-[2,3'-bipyridine]-6-carboxamide;
6'-amino-N-(2-morpholinothiazolo[5,4-b]pyridin-5-yl)-[2,3'-bipyridine]-6-carboxamide;
2-(2-methylpyridin-4-yl)-N-(2-morpholinothiazolo[4,5-b]pyridin-6-yl)oxazole-4-carboxamide;
6'-amino-N-(2-morpholinothiazolo[4,5-b]pyridin-6-yl)-[2,3'-bipyridine]-6-carboxamide;

-continued

N-(2-morpholinothiazolo[4,5-b]pyridin-6-yl)-6-(1H-pyrazol-4-yl)picolinamide;
3-(4-(aminomethyl)piperidin-1-yl)-5-fluoro-N-(2-morpholinothiazolo[4,5-b]pyridin-6-yl)benzamide;
2-(4-(aminomethyl)piperidin-1-yl)-5-fluoro-N-(2-morpholinothiazolo[4,5-b]pyridin-6-yl)benzamide;
2-(2-methylpyridin-4-yl)-N-(2-morpholino-5-(piperidin-1-yl)thiazolo[4,5-b]pyridin-6-yl)oxazole-4-carboxamide;
N-(2-morpholino-5-(piperidin-1-yl)thiazolo[4,5-b]pyridin-6-yl)-6-(1H-pyrazol-4-yl)picolinamide;
N-(2,5-di(piperidin-1-yl)thiazolo[4,5-b]pyridin-6-yl)-6-(1H-pyrazol-4-yl)picolinamide;
N-(2,5-di(piperidin-1-yl)thiazolo[4,5-b]pyridin-6-yl)-2-(2-methylpyridin-4-yl)oxazole-4-carboxamide;
N-(2,5-dimorpholinooxazolo[4,5-b]pyridin-6-yl)-2-(2-methylpyridin-4-yl)oxazole-4-carboxamide;
N-(5-(4-methylpiperazin-1-yl)-2-morpholinooxazolo[4,5-b]pyridin-6-yl)-2-(2-methylpyridin-4-yl)oxazole-4-carboxamide;
N-(2,5-di(piperidin-1-yl)oxazolo[4,5-b]pyridin-6-yl)-2-(6-methoxypyridin-3-yl)oxazole-4-carboxamide;
N-(2,5-di(piperidin-1-yl)oxazolo[4,5-b]pyridin-6-yl)-2-(2-methylpyridin-3-yl)oxazole-4-carboxamide;
N-(2,5-di(piperidin-1-yl)oxazolo[4,5-b]pyridin-6-yl)-2-(2-hydroxypyridin-3-yl)oxazole-4-carboxamide;
2-(2-hydroxypyridin-3-yl)-N-(2-morpholino-5-(piperidin-1-yl)oxazolo[4,5-b]pyridin-6-yl)oxazole-4-carboxamide;
N-(2,5-di(piperidin-1-yl)oxazolo[4,5-b]pyridin-6-yl)-2-(6-hydroxypyridin-3-yl)oxazole-4-carboxamide;
2-(2-methoxypyridin-4-yl)-N-(2-morpholino-5-(piperidin-1-yl)oxazolo[4,5-b]pyridin-6-yl)oxazole-4-carboxamide;
2-(2-methylpyridin-3-yl)-N-(2-morpholino-5-(piperidin-1-yl)oxazolo[4,5-b]pyridin-6-yl)oxazole-4-carboxamide;
2-(3-methylpyridin-4-yl)-N-(2-morpholino-5-(piperidin-1-yl)oxazolo[4,5-b]pyridin-6-yl)oxazole-4-carboxamide;
N-(2,5-di(piperidin-1-yl)oxazolo[4,5-b]pyridin-6-yl)-2-(3-methylpyridin-4-yl)oxazole-4-carboxamide;
2-(6-methylpyridin-3-yl)-N-(2-morpholino-5-(piperidin-1-yl)oxazolo[4,5-b]pyridin-6-yl)oxazole-4-carboxamide;
6-(1-methyl-1H-pyrazol-4-yl)-N-(2-morpholino-5-(piperidin-1-yl)oxazolo[4,5-b]pyridin-6-yl)picolinamide;
N-(2,5-di(piperidin-1-yl)oxazolo[4,5-b]pyridin-6-yl)-2-(6-methylpyridin-3-yl)oxazole-4-carboxamide;
(S)-N-(5-(3-aminopyrrolidin-1-yl)-2-morpholinooxazolo[4,5-b]pyridin-6-yl)-2-(2-methylpyridin-4-yl)oxazole-4-carboxamide;
(S)-N-(5-(3-hydroxypyrrolidin-1-yl)-2-morpholinooxazolo[4,5-b]pyridin-6-yl)-2-(2-methylpyridin-4-yl)oxazole-4-carboxamide;
(R)-N-(5-(3-aminopyrrolidin-1-yl)-2-morpholinooxazolo[4,5-b]pyridin-6-yl)-2-(2-methylpyridin-4-yl)oxazole-4-carboxamide;
(R)-N-(5-(3-hydroxypyrrolidin-1-yl)-2-morpholinooxazolo[4,5-b]pyridin-6-yl)-2-(2-methylpyridin-4-yl)oxazole-4-carboxamide;
(S)-2-(3-aminopyrrolidin-1-yl)-N-(2-morpholino-5-(piperidin-1-yl)oxazolo[4,5-b]pyridin-6-yl)oxazole-4-carboxamide;
(S)-6-(3-hydroxypyrrolidin-1-yl)-N-(2-morpholino-5-(piperidin-1-yl)oxazolo[4,5-b]pyridin-6-yl)picolinamide;
(S)-6-(3-aminopyrrolidin-1-yl)-N-(2-morpholino-5-(piperidin-1-yl)oxazolo[4,5-b]pyridin-6-yl)picolinamide;
(S)-2-(3-hydroxypyrrolidin-1-yl)-N-(2-morpholino-5-(piperidin-1-yl)oxazolo[4,5-b]pyridin-6-yl)oxazole-4-carboxamide;
(S)-N-(5-cyclopropyl-2-morpholinooxazolo[4,5-b]pyridin-6-yl)-2-(3-hydroxypyrrolidin-1-yl)oxazole-4-carboxamide;
(S)-2-(3-aminopyrrolidin-1-yl)-N-(5-cyclopropyl-2-morpholinooxazolo[4,5-b]pyridin-6-yl)oxazole-4-carboxamide;
2-(2-methylpyridin-4-yl)-N-(5-(piperidin-1-yl)-2-(pyrrolidin-1-yl)oxazolo[4,5-b]pyridin-6-yl)oxazole-4-carboxamide hydrochloride;
N-(2-(2,6-dimethylmorpholino)-5-(piperidin-1-yl)oxazolo[4,5-b]pyridin-6-yl)-2-(2-methylpyridin-4-yl)oxazole-4-carboxamide hydrochloride;
N-(2,5-di(piperidin-1-yl)thiazolo[4,5-b]pyridin-6-yl)-6-(1-methyl-1H-pyrazol-4-yl)picolinamide hydrochloride;
6-(1-methyl-1H-pyrazol-4-yl)-N-(2-morpholino-5-(piperidin-1-yl)thiazolo[4,5-b]pyridin-6-yl)picolinamide;
N-(2,5-di(piperidin-1-yl)thiazolo[4,5-b]pyridin-6-yl)-2-(2-methylpyridin-3-yl)oxazole-4-carboxamide hydrochloride;
N-(2-((2S,6R)-2,6-dimethylmorpholino)-5-(piperidin-1-yl)thiazolo[4,5-b]pyridin-6-yl)-2-(2-methylpyridin-4-yl)oxazole-4-carboxamide;
2-(2-methylpyridin-3-yl)-N-(2-morpholino-5-(piperidin-1-yl)thiazolo[4,5-b]pyridin-6-yl)oxazole-4-carboxamide;
2-(2-hydroxypyridin-3-yl)-N-(2-morpholino-5-(piperidin-1-yl)thiazolo[4,5-b]pyridin-6-yl)oxazole-4-carboxamide;
N-(2,5-di(piperidin-1-yl)thiazolo[4,5-b]pyridin-6-yl)-2-(2-methoxypyridin-4-yl)oxazole-4-carboxamide;

-continued 2-(6-methoxypyridin-3-yl)-N-(2-morpholino-5-(piperidin-1-yl)thiazolo[4,5-b]pyridin-6-yl)oxazole-4-carboxamide;
2-(2-methoxypyridin-4-yl)-N-(2-morpholino-5-(piperidin-1-yl)thiazolo[4,5-b]pyridin-6-yl)oxazole-4-carboxamide;
(S)-N-(5-(3-fluoropiperidin-1-yl)-2-morpholinothiazolo[4,5-b]pyridin-6-yl)-2-(2-methylpyridin-4-yl)oxazole-4-carboxamide;
2-(6-methylpyridin-3-yl)-N-(2-morpholino-5-(piperidin-1-yl)thiazolo[4,5-b]pyridin-6-yl)oxazole-4-carboxamide;
2-(3-methylpyridin-4-yl)-N-(2-morpholino-5-(piperidin-1-yl)thiazolo[4,5-b]pyridin-6-yl)oxazole-4-carboxamide;
(S)-6-(3-aminopyrrolidin-1-yl)-N-(2-morpholino-5-(piperidin-1-yl)thiazolo[4,5-b]pyridin-6-yl)picolinamide;
(S)-6-(3-hydroxypyrrolidin-1-yl)-N-(2-morpholino-5-(piperidin-1-yl)thiazolo[4,5-b]pyridin-6-yl)picolinamide;
(S)-6-(3-aminopyrrolidin-1-yl)-N-(2,5-di(piperidin-1-yl)thiazolo[4,5-b]pyridin-6-yl)picolinamide;
(S)-N-(2,5-di(piperidin-1-yl)thiazolo[4,5-b]pyridin-6-yl)-6-(3-hydroxypyrrolidin-1-yl)picolinamide;
(S)-2-(3-aminopyrrolidin-1-yl)-N-(2-morpholino-5-(piperidin-1-yl)thiazolo[4,5-b]pyridin-6-yl)oxazole-4-carboxamide;
(S)-N-(5-(3-aminopyrrolidin-1-yl)-2-morpholinothiazolo[4,5-b]pyridin-6-yl)-2-(2-methylpyridin-4-yl)oxazole-4-carboxamide;
(S)-2-(3-aminopyrrolidin-1-yl)-N-(5-cyclopropyl-2-morpholinothiazolo[4,5-b]pyridin-6-yl)oxazole-4-carboxamide;
N-(5-cyclopropyl-2-morpholinothiazolo[4,5-b]pyridin-6-yl)-2-(2-methylpyridin-4-yl)oxazole-4-carboxamide;
(S)-2-(3-hydroxypyrrolidin-1-yl)-N-(2-morpholino-5-(piperidin-1-yl)thiazolo[4,5-b]pyridin-6-yl)oxazole-4-carboxamide;
(S)-N-(5-(3-hydroxypyrrolidin-1-yl)-2-morpholinothiazolo[4,5-b]pyridin-6-yl)-2-(2-methylpyridin-4-yl)oxazole-4-carboxamide;
(S)-N-(5-cyclopropyl-2-morpholinothiazolo[4,5-b]pyridin-6-yl)-6-(3-hydroxypyrrolidin-1-yl)picolinamide;
(S)-N-(5-cyclopropyl-2-morpholinothiazolo[4,5-b]pyridin-6-yl)-2-(3-hydroxypyrrolidin-1-yl)oxazole-4-carboxamide;
(S)-N-(5-cyclopropyl-2-morpholinothiazolo[4,5-b]pyridin-6-yl)-6-(1-(2-hydroxypropyl)-1H-pyrazol-4-yl)picolinamide;
(S)-N-(5-cyclopropyl-2-morpholinothiazolo[4,5-b]pyridin-6-yl)-2-(1-(2-hydroxypropyl)-1H-pyrazol-4-yl)oxazole-4-carboxamide;
N-(5-(3-hydroxypyrrolidin-1-yl)-2-morpholinothiazolo[4,5-b]pyridin-6-yl)-2-(6-methoxypyridin-3-yl)oxazole-4-carboxamide;
(S)-N-(5-(3-hydroxypyrrolidin-1-yl)-2-morpholinothiazolo[4,5-b]pyridin-6-yl)-2-(6-methoxypyridin-3-yl)oxazole-4-carboxamide;
(R)-N-(5-(3-hydroxypyrrolidin-1-yl)-2-morpholinothiazolo[4,5-b]pyridin-6-yl)-2-(6-methoxypyridin-3-yl)oxazole-4-carboxamide;
(S)-N-(5-(azetidin-1-yl)-2-morpholinothiazolo[4,5-b]pyridin-6-yl)-6-(3-hydroxypyrrolidin-1-yl)picolinamide;
N-(5-(3-hydroxyazetidin-1-yl)-2-morpholinothiazolo[4,5-b]pyridin-6-yl)-2-(2-methylpyridin-4-yl)oxazole-4-carboxamide;
(S)-N-(5-(3-hydroxypyrrolidin-1-yl)-2-morpholinothiazolo[4,5-b]pyridin-6-yl)-5-(2-methylpyridin-4-yl)thiophene-2-carboxamide;
(S)-N-(5-(3-hydroxypyrrolidin-1-yl)-2-morpholinothiazolo[4,5-b]pyridin-6-yl)-5-(2-methylpyridin-4-yl)furan-2-carboxamide;
(S)-N-(5-(3-hydroxypiperidin-1-yl)-2-morpholinothiazolo[4,5-b]pyridin-6-yl)-2-(2-methylpyridin-4-yl)oxazole-4-carboxamide;
N-(5-(4-hydroxypiperidin-1-yl)-2-morpholinothiazolo[4,5-b]pyridin-6-yl)-2-(2-methylpyridin-4-yl)oxazole-4-carboxamide
(R)-N-(5-(3-hydroxypyrrolidin-1-yl)-2-morpholinothiazolo[4,5-b]pyridin-6-yl)-2-(2-methylpyridin-4-yl)oxazole-4-carboxamide;
N-(5-(4-hydroxypiperidin-1-yl)-2-morpholinothiazolo[4,5-b]pyridin-6-yl)-5-(2-methylpyridin-4-yl)furan-2-carboxamide;
N-(5-(azetidin-1-yl)-2-(piperidin-1-yl)thiazolo[4,5-b]pyridin-6-yl)-2-(2-methylpyridin-4-yl)oxazole-4-carboxamide;
2-(2-methylpyridin-4-yl)-N-(2-(piperidin-1-yl)-5-(pyrrolidin-1-yl)thiazolo[4,5-b]pyridin-6-yl)oxazole-4-carboxamide;
2-(2-methylpyridin-4-yl)-N-(2-morpholino-5-(pyrrolidin-1-yl)thiazolo[4,5-b]pyridin-6-yl)oxazole-4-carboxamide;
5-(2-methylpyridin-4-yl)-N-(2-morpholino-5-(piperidin-1-yl)thiazolo[4,5-b]pyridin-6-yl)furan-2-carboxamide;
N-(5-(azepan-1-yl)-2-morpholinothiazolo[4,5-b]pyridin-6-yl)-2-(2-methylpyridin-4-yl)oxazole-4-carboxamide;
2-(2-aminopyridin-4-yl)-N-(2-morpholino-5-(piperidin-1-yl)thiazolo[4,5-b]pyridin-6-yl)oxazole-4-carboxamide hydrochloride;
N-(5-(azetidin-1-yl)-2-morpholinothiazolo[4,5-b]pyridin-6-yl)-2-(2-methylpyridin-4-yl)oxazole-4-carboxamide;
(R)-N-(5-(3-hydroxypiperidin-1-yl)-2-morpholinothiazolo[4,5-b]pyridin-6-yl)-2-(2-methylpyridin-4-yl)oxazole-4-carboxamide;
(R)-N-(5-(3-hydroxypiperidin-1-yl)-2-morpholinothiazolo[4,5-b]pyridin-6-yl)-5-(2-methylpyridin-4-yl)furan-2-carboxamide
;

-continued (S)-6-(1-(2-hydroxypropyl)-1H-pyrazol-4-yl)-N-(2-morpholino-5-(piperidin-1-yl)thiazolo[4,5-b]pyridin-6-yl)picolinamide
N-(5-(4-fluoropiperidin-1-yl)-2-morpholinothiazolo[4,5-b]pyridin-6-yl)-5-(2-methylpyridin-4-yl)furan-2-carboxamide
N-(5-(4-fluoropiperidin-1-yl)-2-morpholinothiazolo[4,5-b]pyridin-6-yl)-2-(2-methylpyridin-4-yl)oxazole-4-carboxamide hydrochloride
N-(5-(1-methyl-1H-pyrazol-4-yl)-2-morpholinothiazolo[4,5-b]pyridin-6-yl)-2-(2-methylpyridin-4-yl)oxazole-4-carboxamide;
N-(5-(3-fluorophenyl)-2-morpholinothiazolo[4,5-b]pyridin-6-yl)-2-(2-methylpyridin-4-yl)oxazole-4-carboxamide;
N-(5-(4-hydroxypiperidin-1-yl)-2-morpholinothiazolo[4,5-b]pyridin-6-yl)-5-(2-methylpyridin-4-yl)furan-2-carboxamide;
N-(5-(3-fluoropiperidin-1-yl)-2-morpholinothiazolo[4,5-b]pyridin-6-yl)-5-(2-methylpyridin-4-yl)furan-2-carboxamide;
(S)-N-(5-(3-hydroxypyrrolidin-1-yl)-2-morpholinooxazolo[4,5-b]pyridin-6-yl)-2-(6-methoxypyridin-3-yl)oxazole-4-carboxamide;
N-(5-(3-hydroxypyrrolidin-1-yl)-2-morpholinooxazolo[4,5-b]pyridin-6-yl)-2-(2-methylpyridin-4-yl)oxazole-4-carboxamide;
(R)-N-(5-(3-hydroxypyrrolidin-1-yl)-2-morpholinooxazolo[4,5-b]pyridin-6-yl)-2-(6-methoxypyridin-3-yl)oxazole-4-carboxamide;
N-(5-(3-hydroxypyrrolidin-1-yl)-2-morpholinooxazolo[4,5-b]pyridin-6-yl)-2-(6-methoxypyridin-3-yl)oxazole-4-carboxamide;
(S)-N-(5-(3-hydroxypyrrolidin-1-yl)-2-morpholinooxazolo[4,5-b]pyridin-6-yl)-5-(2-methylpyridin-4-yl)furan-2-carboxamide;
(S)-N-(5-(3-hydroxypyrrolidin-1-yl)-2-morpholinooxazolo[4,5-b]pyridin-6-yl)-5-(2-methylpyridin-4-yl)thiophene-2-carboxamide;
N-(5-(azetidin-1-yl)-2-(piperidin-1-yl)oxazolo[4,5-b]pyridin-6-yl)-2-(2-methylpyridin-4-yl)oxazole-4-carboxamide;
2-(2-methylpyridin-4-yl)-N-(2-(piperidin-1-yl)-5-(pyrrolidin-1-yl)oxazolo[4,5-b]pyridin-6-yl)oxazole-4-carboxamide;
5-(2-methylpyridin-4-yl)-N-(2-morpholino-5-(piperidin-1-yl)oxazolo[4,5-b]pyridin-6-yl)furan-2-carboxamide;
N-(5-(azetidin-1-yl)-2-morpholinooxazolo[4,5-b]pyridin-6-yl)-2-(2-methylpyridin-4-yl)oxazole-4-carboxamide;
2-(2-methylpyridin-4-yl)-N-(2-morpholino-5-(pyrrolidin-1-yl)oxazolo[4,5-b]pyridin-6-yl)oxazole-4-carboxamide;
N-(5-(4-hydroxypiperidin-1-yl)-2-morpholinooxazolo[4,5-b]pyridin-6-yl)-5-(2-methylpyridin-4-yl)furan-2-carboxamide;
(R)-N-(5-(3-hydroxypiperidin-1-yl)-2-morpholinooxazolo[4,5-b]pyridin-6-yl)-5-(2-methylpyridin-4-yl)furan-2-carboxamide;
N-(5-(furan-3-yl)-2-morpholinooxazolo[4,5-b]pyridin-6-yl)-2-(2-methylpyridin-4-yl)oxazole-4-carboxamide;
N-(5-(3-fluoropiperidin-1-yl)-2-morpholinooxazolo[4,5-b]pyridin-6-yl)-2-(2-methylpyridin-4-yl)oxazole-4-carboxamide;
N-(5-(4-hydroxypiperidin-1-yl)-2-morpholinooxazolo[4,5-b]pyridin-6-yl)-2-(2-methylpyridin-4-yl)oxazole-4-carboxamide;
N-(5-(4-fluoropiperidin-1-yl)-2-morpholinooxazolo[4,5-b]pyridin-6-yl)-2-(2-methylpyridin-4-yl)oxazole-4-carboxamide;
(S)-N-(5-(3-aminopiperidin-1-yl)-2-morpholinothiazolo[4,5-b]pyridin-6-yl)-2-(2-methylpyridin-4-yl)oxazole-4-carboxamide;
2-(2-methylpyridin-4-yl)-N-(2-morpholino-5-(1H-pyrazol-4-yl)thiazolo[4,5-b]pyridin-6-yl)oxazole-4-carboxamide;
N-(5-(6-fluoropyridin-3-yl)-2-morpholinothiazolo[4,5-b]pyridin-6-yl)-2-(2-methylpyridin-4-yl)oxazole-4-carboxamide;
N-(5-(3-hydroxy-8-azabicyclo[3.2.1]octan-8-yl)-2-morpholinothiazolo[4,5-b]pyridin-6-yl)-2-(2-methylpyridin-4-yl)oxazole-4-carboxamide;
N-(2-(3-hydroxypiperidin-1-yl)-5-(piperidin-1-yl)thiazolo[4,5-b]pyridin-6-yl)-2-(2-methylpyridin-4-yl)oxazole-4-carboxamide;
2-(2-acetamidopyridin-4-yl)-N-(5-(4-hydroxypiperidin-1-yl)-2-morpholinothiazolo[4,5-b]pyridin-6-yl)oxazole-4-carboxamide;
N-(2-(3-hydroxypiperidin-1-yl)-5-(4-hydroxypiperidin-1-yl)thiazolo[4,5-b]pyridin-6-yl)-2-(2-methylpyridin-4-yl)oxazole-4-carboxamide;
2-(2-acetamidopyridin-4-yl)-N-(5-(3-hydroxypiperidin-1-yl)-2-morpholinothiazolo[4,5-b]pyridin-6-yl)oxazole-4-carboxamide;
2-(2-aminopyridin-4-yl)-N-(5-(3-hydroxypiperidin-1-yl)-2-morpholinothiazolo[4,5-b]pyridin-6-yl)oxazole-4-carboxamide hydrochloride;
5-(2-aminopyridin-4-yl)-N-(5-(4-hydroxypiperidin-1-yl)-2-morpholinothiazolo[4,5-b]pyridin-6-yl)furan-3-carboxamide hydrochloride;
2-(2-aminopyridin-4-yl)-N-(5-(4-hydroxypiperidin-1-yl)-2-morpholinothiazolo[4,5-b]pyridin-6-yl)oxazole-4-carboxamide hydrochloride;
2-(2-aminopyridin-4-yl)-N-(5-(4-fluoropiperidin-1-yl)-2-morpholinothiazolo[4,5-b]pyridin-6-yl)oxazole-4-carboxamide hydrochloride;
N-(5-(2-fluoropyridin-4-yl)-2-morpholinothiazolo[4,5-b]pyridin-6-yl)-2-(2-methylpyridin-4-yl)oxazole-4-carboxamide;
N-(5-(4-fluoropiperidin-1-yl)-2-(3-hydroxypiperidin-1-yl)thiazolo[4,5-b]pyridin-6-yl)-2-(2-methylpyridin-4-yl)oxazole-4-carboxamide;
N-(5-(4-aminopiperidin-1-yl)-2-(3-hydroxypiperidin-1-yl)thiazolo[4,5-b]pyridin-6-yl)-2-(2-methylpyridin-4-yl)oxazole-4-carboxamide hydrochloride; and -continued

| |
|---|
| N-(5-(2-hydroxypyridin-4-yl)-2-morpholinothiazolo[4,5-b]pyridin-6-yl)-2-(2-methylpyridin-4-yl)oxazole-4-carboxamide hydrochloride; |

or a pharmaceutically acceptable salt thereof.

37. The method of claim 1, wherein the compound of formula (II) is selected from:

6'-amino-N-(2-morpholinooxazolo[5,4-b]pyridin-5-yl)-[2,3'-bipyridine]-6-carboxamide;

N-(5-(4-hydroxypiperidin-1-yl)-2-morpholinooxazolo[4,5-b]pyridin-6-yl)-5-(2-methylpyridin-4-yl)furan-2-carboxamide;

N-(2,5-di(piperidin-1-yl)oxazolo[4,5-b]pyridin-6-yl)-6-(1H-pyrazol-4-yl)picolinamide hydrochloride; and (R)—N-(5-(3-hydroxypyrrolidin-1-yl)-2-morpholinooxazolo[4,5-b]pyridin-6-yl)-2-(2-methylpyridin-4-yl)oxazole-4-carboxamide;

or a pharmaceutically acceptable salt thereof.

38. The method of claim 1, wherein the compound of formula (II) is selected from:

N-(5-(3-fluoropiperidin-1-yl)-2-morpholinothiazolo[4,5-b]pyridin-6-yl)-5-(2-methylpyridin-4-yl)furan-2-carboxamide;

N-(5-(azepan-1-yl)-2-morpholinothiazolo[4,5-b]pyridin-6-yl)-2-(2-methylpyridin-4-yl)oxazole-4-carboxamide;

(R)—N-(5-(3-hydroxypyrrolidin-1-yl)-2-morpholinooxazolo[4,5-b]pyridin-6-yl)-2-(2-methylpyridin-4-yl)oxazole-4-carboxamide; and N-(2,5-di(piperidin-1-yl)thiazolo[4,5-b]pyridin-6-yl)-6-(1H-pyrazol-4-yl)picolinamide;

or a pharmaceutically acceptable salt thereof.

39. The method of claim 1, wherein the compound represented by formula (II) is

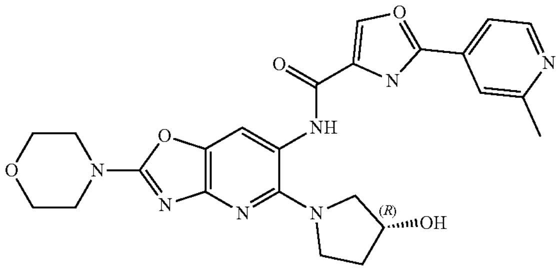

or a pharmaceutically acceptable salt thereof.

40. The method of claim 1, wherein the compound represented by formula (II) is

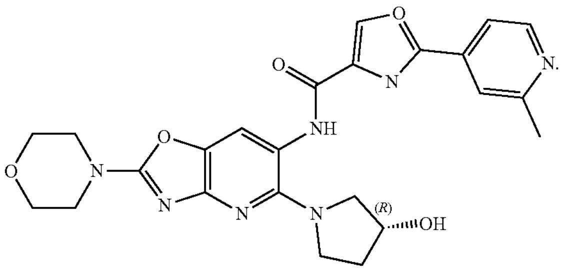

41. The method of claim 1, wherein the compound represented by formula (II) is

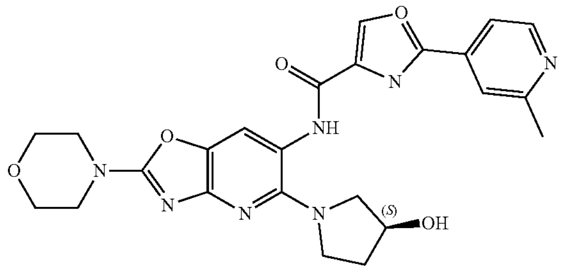

or a pharmaceutically acceptable salt thereof.

42. The method of claim 1, wherein the compound represented by formula (II) is

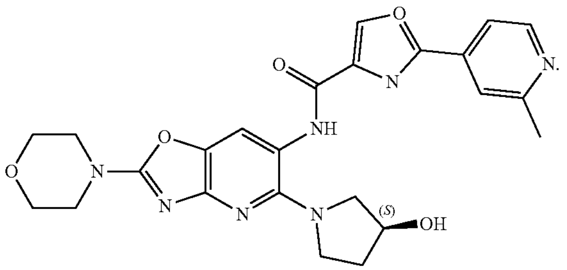

43. The method of claim 1, wherein the compound represented by formula (II) is

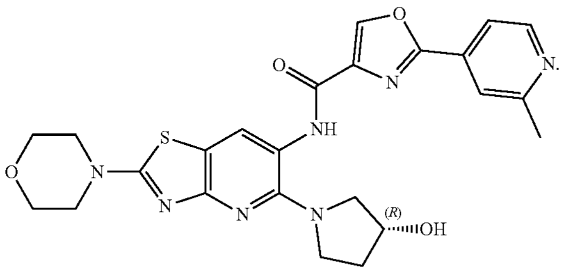

or a pharmaceutically acceptable salt thereof.

44. The method of claim 1, wherein the compound represented by formula (II) is

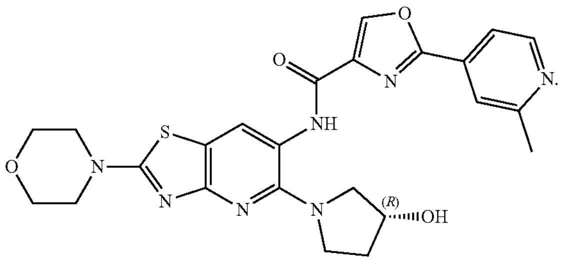

45. The method of claim 1, wherein the compound represented by formula (II) is

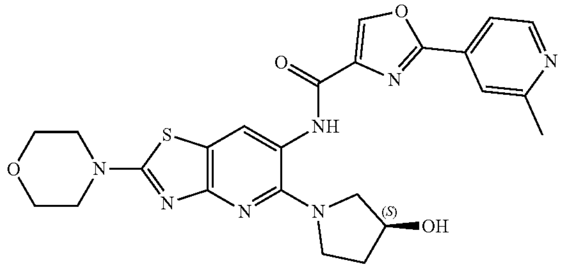

or a pharmaceutically acceptable salt thereof.

46. The method of claim 1, wherein the compound represented by formula (II) is

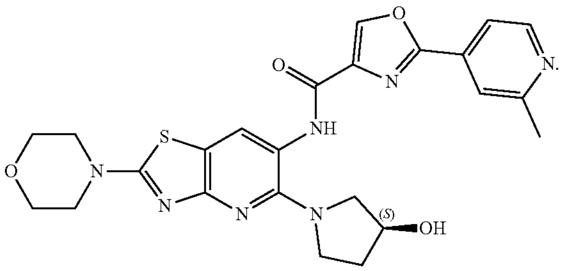

47. The method of claim 1, wherein the compound represented by formula (II) is

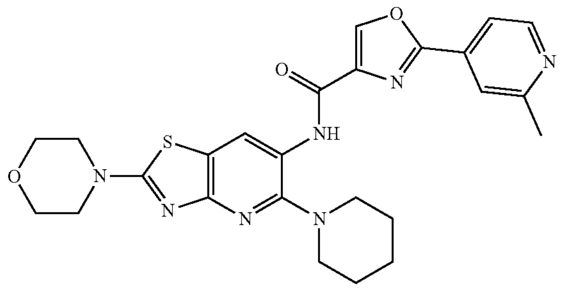 [SMILES: Cc1cc(-c2nc(C(=O)Nc3cc4sc(N5CCOCC5)nc4nc3N3CCCCC3)co2)ccn1]

or a pharmaceutically acceptable salt thereof.

48. The method of claim 1, wherein the compound represented by formula (II) is

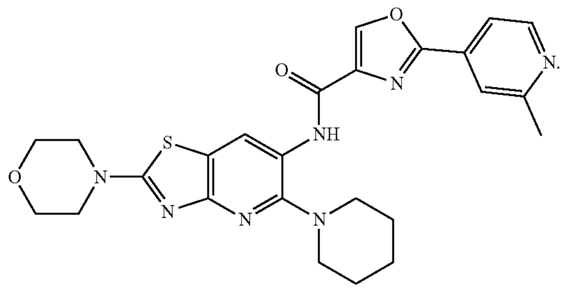 [SMILES: Cc1cc(-c2nc(C(=O)Nc3cc4sc(N5CCOCC5)nc4nc3N3CCCCC3)co2)ccn1]

49. The method of claim 1, wherein the compound represented by formula (II) is

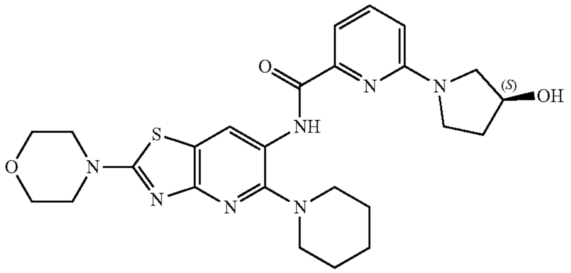

or a pharmaceutically acceptable salt thereof.

50. The method of claim 1, wherein the compound represented by formula (II) is

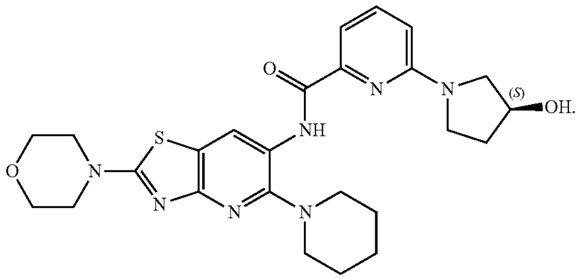

51. The method of claim 1, wherein the subject has a mutation in FLT-3 kinase.

52. The method of claim 51, wherein the mutation is an internal tandem duplication (ITD).

53. The method of claim 51, wherein the mutation is selected from D835H, D835V, D835Y, K663Q, N841I, ITD, and F691L.

54. The method of claim 1, wherein the MDS is resistant to an FLT-3 inhibitor.

* * * * *